US009260431B2

(12) United States Patent
Chong

(10) Patent No.: US 9,260,431 B2
(45) Date of Patent: Feb. 16, 2016

(54) COMPOUNDS AND COMPOSITIONS FOR TREATING CHEMICAL WARFARE AGENT-INDUCED INJURIES

(71) Applicant: Jayhong A. Chong, Brookline, MA (US)

(72) Inventor: Jayhong A. Chong, Brookline, MA (US)

(73) Assignee: HYDRA BIOSCIENCES, INC., Cambridge, MA (US)

( * ) Notice: Subject to any disclaimer, the term of this patent is extended or adjusted under 35 U.S.C. 154(b) by 0 days.

(21) Appl. No.: 14/198,050

(22) Filed: Mar. 5, 2014

(65) Prior Publication Data

US 2014/0303192 A1 Oct. 9, 2014

Related U.S. Application Data

(63) Continuation of application No. 13/655,316, filed on Oct. 18, 2012, now Pat. No. 8,710,052, which is a continuation of application No. 12/466,187, filed on May 14, 2009, now Pat. No. 8,318,728.

(60) Provisional application No. 61/127,665, filed on May 14, 2008, provisional application No. 61/127,723, filed on May 14, 2008, provisional application No. 61/127,787, filed on May 14, 2008, provisional application No. 61/127,790, filed on May 14, 2008, provisional application No. 61/127,682, filed on May 14, 2008, provisional application No. 61/127,666, filed on May 14, 2008, provisional application No. 61/127,664, filed on May 14, 2008.

(51) Int. Cl.

| | |
|---|---|
| ***C07D 473/30*** | (2006.01) |
| ***C07D 487/04*** | (2006.01) |
| ***A61K 31/4188*** | (2006.01) |
| ***A61K 31/519*** | (2006.01) |
| ***A61K 9/00*** | (2006.01) |
| ***C07D 471/04*** | (2006.01) |

(52) U.S. Cl.

CPC ............ *C07D 473/30* (2013.01); *A61K 9/0014* (2013.01); *A61K 9/0019* (2013.01); *A61K 9/0048* (2013.01); *A61K 9/0053* (2013.01); *A61K 31/4188* (2013.01); *A61K 31/519* (2013.01); *C07D 471/04* (2013.01); *C07D 487/04* (2013.01)

(58) Field of Classification Search

CPC ............ A61K 31/519; A61K 31/4188; A61K 9/0014; A61K 9/0019; A61K 9/0048; A61K 9/0053; C07D 471/04; C07D 473/30

USPC ............. 514/263.2, 262.1, 263.3, 303, 227.8, 514/367, 371, 375, 393

See application file for complete search history.

(56) References Cited

U.S. PATENT DOCUMENTS

| | | | |
|---|---|---|---|
| 4,297,494 | A | 10/1981 | Groman et al. |
| 4,548,939 | A | 10/1985 | Kennis et al. |
| 4,871,742 | A | 10/1989 | Bonne et al. |
| 4,960,773 | A | 10/1990 | Korbonits et al. |
| 5,068,236 | A | 11/1991 | Suzuki et al. |
| 6,545,002 | B1 | 4/2003 | Linden et al. |
| 6,608,069 | B1 | 8/2003 | Daluge et al. |
| 7,135,475 | B2 | 11/2006 | Dunten et al. |
| 7,671,061 | B2 | 3/2010 | Moran et al. |
| 8,163,761 | B2 | 4/2012 | Ng et al. |
| 2003/0199693 | A1 | 10/2003 | Chen |
| 2003/0203847 | A1 | 10/2003 | Rosenfeld et al. |
| 2004/0053973 | A1 | 3/2004 | Ohkawa et al. |
| 2005/0209243 | A1 | 9/2005 | Chen |
| 2006/0142309 | A1 | 6/2006 | Baraldi et al. |
| 2006/0247226 | A1 | 11/2006 | Himmelsbach et al. |
| 2007/0072851 | A1 | 3/2007 | Buchanan et al. |
| 2007/0219222 | A1 | 9/2007 | Moran et al. |
| 2009/0143377 | A1 | 6/2009 | Ng et al. |
| 2011/0144137 | A1 | 6/2011 | Jordt et al. |

FOREIGN PATENT DOCUMENTS

| | | | |
|---|---|---|---|
| WO | 2005000309 | A2 | 1/2005 |
| WO | 2007073505 | A2 | 6/2007 |
| WO | 2009140517 | A1 | 11/2009 |
| WO | 2009140519 | A1 | 11/2009 |
| WO | 2010075353 | A1 | 7/2010 |

OTHER PUBLICATIONS

Bessac et al, Physiology Published Dec. 1, 2008 vol. 23 No. 6, 360-370.*

Cassillas et al, J. Appl. Toxicol. 20, S145-S151 (2000).*

Bautista et al.: "TRPA1 Mediates the Inflammatory Action of Envriomental Irritants amd Proalgeaic Agents"; 2006; Cell; 124: 1269-1282.

Casillas et al. "Therapeutic Approaches to Dermatotoxicity by Sulfer Mustard I. Modulation of Sulfur Mustard-induced Cutaneous Injury in the Mouse Ear Vesicant Model", Journal of Applied Toxicology 20, S145-S151 (2000).

European Agency for the Evaluation of Medicinal Products. EMEA/CPMP Guidance Document on the Use of Medicinal Products for the Treatment of Patients Exposed to Terrorist Attacks with Chemical Agents. 2003, pp. 2-17, < www.ema.europa.eu/pdfs/human/chemicalterrorism/125503en.pdf>.

Geoghegan, Con Ed in Anaesthesia, vol. 6, No. 6, 2006.

International Preliminary Report and Written Opinion for International Application No. PCT/US10/35005 dated Jun. 25, 2010.

International Search Report and Written Opinion for International Application No. PCT/US09/43971 dated Jun. 2, 2010.

International Search Report for International Application No. PCT/US09/43985 dated Jun. 16, 2009.

International Search Report for International Application No. PCT/US09/43987, dated Jun. 24, 2009.

International Search Report for International Application No. PCT/US10/35005 dated Jul. 14, 2010.

* cited by examiner

*Primary Examiner* — Wu-Cheng Winston Shen
*Assistant Examiner* — Jean Cornet
(74) *Attorney, Agent, or Firm* — Lando & Anastasi, LLP

(57) ABSTRACT

Compounds and compositions for treating injuries caused by exposure to chemical warfare agents are described herein.

18 Claims, No Drawings

COMPOUNDS AND COMPOSITIONS FOR TREATING CHEMICAL WARFARE AGENT-INDUCED INJURIES

CLAIM OF PRIORITY

This application is a continuation of U.S. application Ser. No. 13/655,316, filed May 14, 2009, now U.S. Pat. No. 8,710,052, which is a continuation of U.S. application Ser. No. 12/466,187, filed May 14, 2009, now U.S. Pat. No. 8,318,728, which claims priority from U.S. Ser. No. 61/127,666, U.S. Ser. No. 61/127,664, U.S. Ser. No. 61/127,665, U.S. Ser. No. 61/127,723, U.S. Ser. No. 61/127,787, U.S. Ser. No. 61/127,790, U.S. Ser. No. 61/127,682, all filed May 14, 2008 and all of which are incorporated herein by reference in their entirety.

BACKGROUND

The invention relates to compounds and compositions useful for treating injuries caused by chemical warfare and similar agents.

A variety of ion channel proteins exist to mediate ion flux across cellular membranes. The proper expression and function of ion channel proteins is essential for the maintenance of cell function and intracellular communication. Numerous diseases and disorders are the result of misregulation of membrane potential or aberrant calcium handling. Given the central importance of ion channels in modulating membrane potential and ion flux in cells, identification of agents that can promote or inhibit particular ion channels are of great interest, both as research tools and as therapeutic agents.

SUMMARY OF THE INVENTION

The present invention provides compounds and compositions for treating or preventing injuries resulting from chemical warfare agents by modulating the activity of the TRPA1 channel.

In one aspect, the invention features a method of treating an injury resulting from exposure to a chemical warfare agent in a subject, such as a human, the method comprising administering to the subject a compound of Formula (II) or a salt thereof Formula (II)

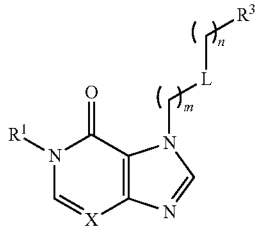

wherein, $R^1$ is $C_1$-$C_6$ alkyl, $C_2$-$C_6$ alkenyl, or $C_2$-$C_6$ alkynyl, each of which is optionally substituted with 1-4 $R^5$;

X is N or $CR^2$ $R^2$ is H, $C_1$-$C_6$ alkyl, $C_2$-$C_6$ alkenyl, or $C_2$-$C_6$ alkynyl, each of which is optionally substituted with 1-4 $R^{5'}$;

L is $NR^6SO_2$, $SO_2NR^6$, $OC(O)NR^6$, $NR^6C(O)O$, $NR^6C(O)NR^6$, $NR^6C(O)$, $C(O)NR^6$, C(O), O, S, S(O), $S(O)_2$, $NR_6$, $CH_2$, cyclyl, aryl, heterocyclyl, or heteroaryl;

$R^3$ is cyclyl, heterocyclyl, aryl, heteroaryl, each of which is optionally substituted with 1-4 $R^7$;

each $R^5$ is independently halo, hydroxyl, alkoxy, amino, alkylamino, dialkylamino, cyano, nitro, amido, alkylamido, dialkylamido, thioyl, sulfonyl, cyclyl, heterocyclyl, aryl, or heteroaryl;

each $R^6$ is independently H, $C_1$-$C_6$ alkyl, arylalkyl, S(O)alkyl, acetyl, amidyl, or S(O)H;

each $R^7$ is independently $C_1$-$C_6$ alkyl, $C_2$-$C_6$ alkenyl, $C_2$-$C_6$ alkynyl, cyclyl, heterocyclyl, aryl, heteroaryl, halo, hydroxyl, alkoxy, aryloxy, arylalkoxy, amino, akylamino, dialkylamino, thioyl, alkylthioyl, sulfonyl, sulfonamidyl, amido, urea, sulfonylurea, hydroxyl alkoxyl, alkoxy alkoxyl, acyl, nitro, cyano, each of which is independently substituted with 1-3 $R^8$;

each $R^8$ is independently $C_1$-$C_6$ alkyl, $C_2$-$C_6$ alkenyl, or $C_2$-$C_6$ alkynyl, halo, hydroxyl, alkoxy, aryloxy, amino, akylamino, dialkylamino, thioyl, sulfonyl, sulfonamidyl, amido, urea, sulfonylurea acyl, nitro, cyano, cyclyl, heterocyclyl, aryl, or heteroaryl;

each m and n are independently 0, 1, 2, 3, 4, 5, or 6, wherein m is at least 2 when L is connected to the methylene carbon via a heteroatom, each $R^9$ is independently H, $C_1$-$C_6$ alkyl, $C_2$-$C_6$ alkenyl, or $C_2$-$C_6$ alkynyl, halo, hydroxyl, alkoxy, aryloxy, arylalkoxy, amino, akylamino, dialkylamino, thioyl, alkylthioyl, sulfonyl, sulfonamidyl, amido, urea, sulfonylurea, acyl, nitro, cyano, each of which is independently substituted with 1-3 $R^8$.

In another aspect, the invention features a method of treating an injury resulting from exposure to a chemical warfare agent in a subject, such as a human, the method comprising administering to the subject a compound of Formula (III) or a salt thereof Formula (III)

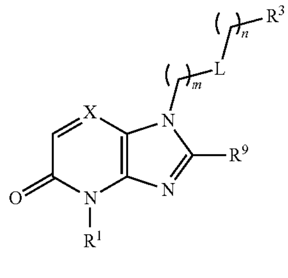

wherein, $R^1$ is $C_1$-$C_6$ alkyl, $C_2$-$C_6$ alkenyl, or $C_2$-$C_6$ alkynyl, each of which is optionally substituted with 1-4 $R^5$;

X is N or $CR^2$ $R^2$ is H, $C_1$-$C_6$ alkyl, $C_2$-$C_6$ alkenyl, or $C_2$-$C_6$ alkynyl, each of which is optionally substituted with 1-4 $R^{5'}$;

L is $NR^6SO_2$, $SO_2NR^6$, $OC(O)NR^6$, $NR^6C(O)O$, $NR^6C(O)NR^6$, $NR^6C(O)$, $C(O)NR^6$, O, C(O), S, S(O), $S(O)_2$, $NR_6$, $CH_2$, cyclyl, aryl, heterocyclyl, or heteroaryl;

$R^3$ is cyclyl, heterocyclyl, aryl, heteroaryl, each of which is optionally substituted with 1-4 $R^7$;

each $R^5$ is independently halo, hydroxyl, alkoxy, amino, alkylamino, dialkylamino, cyano, nitro, amido, alkylamido, dialkylamido, thioyl, sulfonyl, cyclyl, heterocyclyl, aryl, or heteroaryl;

each $R^6$ is independently H, $C_1$-$C_6$ alkyl, arylalkyl, S(O)alkyl, acetyl, amidyl, or S(O)H;

each $R^7$ is independently $C_1$-$C_6$ alkyl, $C_2$-$C_6$ alkenyl, or $C_2$-$C_6$ alkynyl, halo, hydroxyl, alkoxy, aryl, heteroaryl, cyclyl, aryloxy, arylalkoxy, amino, akylamino, dialkylamino, thioyl, alkylthioyl, sulfonyl, sulfonamidyl, amido, hydroxyl alkoxyl, alkoxy alkoxyl, urea, sulfonylurea, acyl, nitro, cyano, each of which is independently substituted with 1-3 $R^8$;

each $R^8$ is independently $C_1$-$C_6$ alkyl, $C_2$-$C_6$ alkenyl, or $C_2$-$C_6$ alkynyl, halo, hydroxyl, alkoxy, aryloxy, amino, akylamino, dialkylamino, thioyl, sulfonyl, sulfonamidyl, amido, urea, sulfonylurea acyl, nitro, cyano, cyclyl, heterocyclyl, aryl, or heteroaryl;

each $R^9$ is independently H, $C_1$-$C_6$ alkyl, $C_2$-$C_6$ alkenyl, or $C_2$-$C_6$ alkynyl, halo, hydroxyl, alkoxy, aryloxy, arylalkoxy, amino, akylamino, dialkylamino, thioyl, alkylthioyl, sulfonyl, sulfonamidyl, amido, urea, sulfonylurea, acyl, nitro, cyano, each of which is independently substituted with 1-3 $R^8$;

each m and n are independently 0, 1, 2, 3, 4, 5, or 6.

In another aspect, the invention features a method of treating an injury resulting from exposure to a chemical warfare agent in a subject, such as a human, the method comprising administering to the subject a compound of Formula (IV) or a salt thereof Formula (IV)

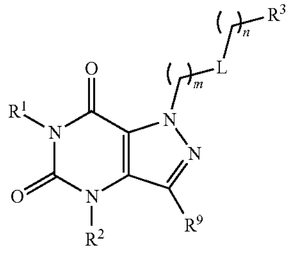

wherein, $R^1$ and $R^2$ are each independently $C_1$-$C_6$ alkyl, $C_2$-$C_6$ alkenyl, or $C_2$-$C_6$ alkynyl, each of which is optionally substituted with 1-4 $R^5$;

L is $NR^6SO_2$, $SO_2NR^6$, $OC(O)NR^6$, $NR^6C(O)O$, $NR^6C(O)NR^6$, $NR^6C(O)$, $C(O)NR^6$, O, C(O), S, S(O), $S(O)_2$, $NR_6$, $CH_2$, cyclyl, aryl, heterocyclyl, or heteroaryl;

$R^3$ is cyclyl, heterocyclyl, aryl, heteroaryl, each of which is optionally substituted with 1-4 $R^7$;

each $R^5$ is independently halo, hydroxyl, alkoxy, amino, alkylamino, dialkylamino, cyano, nitro, amido, alkylamido, dialkylamido, thioyl, sulfonyl, cyclyl, heterocyclyl, aryl, or heteroaryl;

each $R^6$ is independently H, $C_1$-$C_6$ alkyl, arylalkyl, S(O)alkyl, acetyl, amidyl, or S(O)H;

each $R^7$ is independently $C_1$-$C_6$ alkyl, $C_2$-$C_6$ alkenyl, $C_2$-$C_6$ alkynyl, cyclyl, heterocyclyl, aryl, heteroaryl, halo, hydroxyl, alkoxy, aryloxy, arylalkoxy, amino, akylamino, dialkylamino, thioyl, alkylthioyl, sulfonyl, sulfonamidyl, amido, urea, sulfonylurea, hydroxyl alkoxyl, alkoxy alkoxyl, acyl, nitro, cyano, each of which is independently substituted with 1-3 $R^8$;

each $R^8$ is independently $C_1$-$C_6$ alkyl, $C_2$-$C_6$ alkenyl, or $C_2$-$C_6$ alkynyl, halo, hydroxyl, alkoxy, aryloxy, amino, akylamino, dialkylamino, thioyl, sulfonyl, sulfonamidyl, amido, urea, sulfonylurea acyl, nitro, cyano, cyclyl, heterocyclyl, aryl, or heteroaryl;

each m and n are independently 0, 1, 2, 3, 4, 5, or 6;

each $R^9$ is independently H, $C_1$-$C_6$ alkyl, $C_2$-$C_6$ alkenyl, or $C_2$-$C_6$ alkynyl, halo, hydroxyl, alkoxy, aryloxy, arylalkoxy, amino, akylamino, dialkylamino, thioyl, alkylthioyl, sulfonyl, sulfonamidyl, amido, urea, sulfonylurea, acyl, nitro, cyano, each of which is independently substituted with 1-3 $R^8$.

In another aspect, the invention features a method of treating an injury resulting from exposure to a chemical warfare agent in a subject, such as a human, the method comprising administering to the subject a compound of Formula (V) or a salt thereof Formula (V)

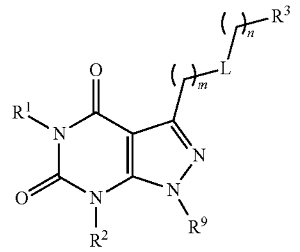

wherein, $R^1$ and $R^2$ are each independently $C_1$-$C_6$ alkyl, $C_2$-$C_6$ alkenyl, or $C_2$-$C_6$ alkynyl, each of which is optionally substituted with 1-4 $R^5$;

L is is $NR^6SO_2$, $SO_2NR^6$, $OC(O)NR^6$, $NR^6C(O)O$, $NR^6C(O)NR^6$, $NR^6C(O)$, $C(O)NR^6$, O, C(O), S, S(O), $S(O)_2$, $NR_6$, $CH_2$, cyclyl, aryl, heterocyclyl, or heteroaryl;

$R^3$ is cyclyl, heterocyclyl, aryl, heteroaryl, each of which is optionally substituted with 1-4 $R^7$;

each $R^5$ is independently halo, hydroxyl, alkoxy, amino, alkylamino, dialkylamino, cyano, nitro, amido, alkylamido, dialkylamido, thioyl, sulfonyl, cyclyl, heterocyclyl, aryl, or heteroaryl;

each $R^6$ is independently H, C1-C¬ 6 alkyl, arylalkyl, S(O)alkyl, acetyl, amidyl, or S(O)H;

each $R^7$ is independently $C_1$-$C_6$ alkyl, $C_2$-$C_6$ alkenyl, $C_2$-$C_6$ alkynyl, cyclyl, heterocyclyl, aryl, heteroaryl, halo, hydroxyl, alkoxy, aryloxy, arylalkoxy, amino, akylamino, dialkylamino, thioyl, alkylthioyl, sulfonyl, sulfonamidyl, amido, urea, sulfonylurea, hydroxyl alkoxyl, alkoxy alkoxyl, acyl, nitro, cyano, each of which is independently substituted with 1-3 $R^8$;

each $R^8$ is independently $C_1$-$C_6$ alkyl, $C_2$-$C_6$ alkenyl, or $C_2$-$C_6$ alkynyl, halo, hydroxyl, alkoxy, aryloxy, amino, akylamino, dialkylamino, thioyl, sulfonyl, sulfonamidyl, amido, urea, sulfonylurea acyl, nitro, cyano, cyclyl, heterocyclyl, aryl, or heteroaryl;

$R^9$ is H, $C_1$-$C_6$ alkyl, or arylalkyl;

each m and n are independently 0, 1, 2, 3, 4, 5, or 6.

In another aspect, the invention features a method of treating an injury resulting from exposure to a chemical warfare agent in a subject, such as a human, the method comprising administering to the subject a compound of Formula (VI) or a salt thereof Formula (VI)

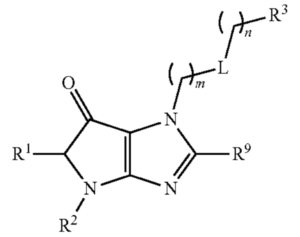

wherein, $R^1$ is $C_1$-$C_6$ alkyl, $C_2$-$C_6$ alkenyl, $C_2$-$C_6$ alkynyl, each of which is optionally substituted with 1-4 $R^5$;

$R^2$ is $C_1$-$C_6$ alkyl, $C_2$-$C_6$ alkenyl, $C_2$-$C_6$ alkynyl, or cycyl, each of which is optionally substituted with 1-4 $R^5$;

L is $NR^6SO_2$, $SO_2NR^6$, $OC(O)NR^6$, $NR^6C(O)O$, $NR^6C(O)NR^6$, $NR^6C(O)$, $C(O)NR^6$, 0, C(O), S, S(O), $S(O)_2$, $NR_6$, $CH_2$, cyclyl, aryl, heterocyclyl, or heteroaryl;

$R^3$ is cyclyl, heterocyclyl, aryl, heteroaryl, each of which is optionally substituted with 1-4 $R^7$;

each $R^5$ is independently halo, hydroxyl, alkoxy, amino, alkylamino, dialkylamino, cyano, nitro, amido, alkylamido, dialkylamido, thioyl, sulfonyl, cyclyl, heterocyclyl, aryl, or heteroaryl;

each $R^6$ is independently H, C1-C¬ 6 alkyl, arylalkyl, S(O)alkyl, acetyl, amidyl, or S(O)H;

each $R^7$ is independently $C_1$-$C_6$ alkyl, $C_2$-$C_6$ alkenyl, $C_2$-$C_6$ alkynyl, cyclyl, heterocyclyl, aryl, heteroaryl, halo, hydroxyl, alkoxy, aryloxy, arylalkoxy, amino, akylamino, dialkylamino, thioyl, alkylthioyl, sulfonyl, sulfonamidyl, amido, urea, sulfonylurea, hydroxyl alkoxyl, alkoxy alkoxyl, acyl, nitro, cyano, each of which is independently substituted with 1-3 $R^8$;

each $R^8$ is independently $C_1$-$C_6$ alkyl, $C_2$-$C_6$ alkenyl, or $C_2$-$C_6$ alkynyl, halo, hydroxyl, alkoxy, aryloxy, amino, akylamino, dialkylamino, thioyl, sulfonyl, sulfonamidyl, amido, urea, sulfonylurea acyl, nitro, cyano, cyclyl, heterocyclyl, aryl, or heteroaryl;

each $R^9$ is independently H, $C_1$-$C_6$ alkyl, $C_2$-$C_6$ alkenyl, or $C_2$-$C_6$ alkynyl, halo, hydroxyl, alkoxy, aryloxy, arylalkoxy, amino, akylamino, dialkylamino, thioyl, alkylthioyl, sulfonyl, sulfonamidyl, amido, urea, sulfonylurea, acyl, nitro, cyano, each of which is independently substituted with 1-3 $R^8$;

each m and n are independently 0, 1, 2, 3, 4, 5, or 6.

In another aspect, the invention features a method of treating an injury resulting from exposure to a chemical warfare agent in a subject, such as a human, the method comprising administering to the subject a compound of Formula (VII) or a salt thereof Formula (VII)

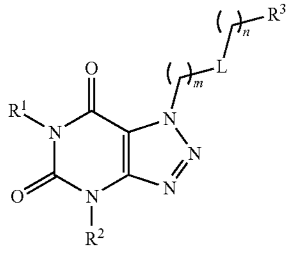

wherein, $R^1$ and $R^2$ are each independently $C_1$-$C_6$ alkyl, $C_2$-$C_6$ alkenyl, or $C_2$-$C_6$ alkynyl, each of which is optionally substituted with 1-4 $R^5$;

L is $NR^6SO_2$, $SO_2NR^6$, $OC(O)NR^6$, $NR^6C(O)O$, $NR^6C(O)NR^6$, $NR^6C(O)$, $C(O)NR^6$, O, C(O), S, S(O), $S(O)_2$, $NR_6$, $CH_2$, cyclyl, aryl, heterocyclyl, or heteroaryl;

$R^3$ is cyclyl, heterocyclyl, aryl, heteroaryl, each of which is optionally substituted with 1-4 $R^7$;

each $R^5$ is independently halo, hydroxyl, alkoxy, amino, alkylamino, dialkylamino, cyano, nitro, amido, alkylamido, dialkylamido, thioyl, sulfonyl, cyclyl, heterocyclyl, aryl, or heteroaryl;

each $R^6$ is independently H, $C_1$-$C_6$ alkyl, arylalkyl, S(O)alkyl, acetyl, amidyl, or S(O)H;

each $R^7$ is independently $C_1$-$C_6$ alkyl, $C_2$-$C_6$ alkenyl, or $C_2$-$C_6$ alkynyl, halo, hydroxyl, alkoxy, aryl, heteroaryl, cyclyl, aryloxy, arylalkoxy, amino, akylamino, dialkylamino, thioyl, alkylthioyl, sulfonyl, sulfonamidyl, amido, hydroxyl alkoxyl, alkoxy alkoxyl, urea, sulfonylurea, acyl, nitro, cyano, each of which is independently substituted with 1-3 $R^8$;

each $R^8$ is independently $C_1$-$C_6$ alkyl, $C_2$-$C_6$ alkenyl, or $C_2$-$C_6$ alkynyl, halo, hydroxyl, alkoxy, aryloxy, amino, akylamino, dialkylamino, thioyl, sulfonyl, sulfonamidyl, amido, urea, sulfonylurea acyl, nitro, cyano, cyclyl, heterocyclyl, aryl, or heteroaryl;

each m and n are independently 0, 1, 2, 3, 4, 5, or 6.

In another aspect, the invention features a method of treating an injury resulting from exposure to a chemical warfare agent in a subject, such as a human, the method comprising administering to the subject a compound of Formula (IX) or a salt thereof Formula (IX)

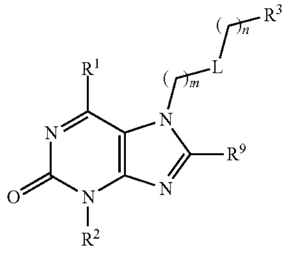

wherein, $R^1$ and $R^2$ are each independently H, $C_1$-$C_6$ alkyl, $C_2$-$C_6$ alkenyl, or $C_2$-$C_6$ alkynyl, each of which is optionally substituted with 1-4 $R^5$;

L is $NR^6SO_2$, $SO_2NR^6$, $OC(O)NR^6$, $NR^6C(O)O$, $NR^6C(O)NR^6$, $NR^6C(O)$, $C(O)NR^6$, O, S, S(O), $S(O)_2$, $NR_6$, or $CH_2$, $R^3$ is cyclyl, heterocyclyl, aryl, heteroaryl, each of which is optionally substituted with 1-4 $R^7$;

each $R^5$ is independently halo, hydroxyl, alkoxy, amino, alkylamino, dialkylamino, cyano, nitro, amido, alkylamido, dialkylamido, thioyl, sulfonyl, cyclyl, heterocyclyl, aryl, or heteroaryl;

each $R^6$ is independently H, $C_1$-$C_6$ alkyl, arylalkyl, S(O)alkyl, acetyl, amidyl, or S(O)H;

each $R^7$ is independently $C_1$-$C_6$ alkyl, $C_2$-$C_6$ alkenyl, $C_2$-$C_6$ alkynyl, cyclyl, heterocyclyl, aryl, heteroaryl, halo, hydroxyl, alkoxy, aryloxy, arylalkoxy, amino, akylamino, dialkylamino, thioyl, alkylthioyl, sulfonyl, sulfonamidyl, amido, urea, sulfonylurea, hydroxyl alkoxyl, alkoxy alkoxyl, acyl, nitro, cyano, each of which is independently substituted with 1-3 $R^8$;

each $R^8$ is independently $C_1$-$C_6$ alkyl, $C_2$-$C_6$ alkenyl, or $C_2$-$C_6$ alkynyl, halo, hydroxyl, alkoxy, aryloxy, amino, akylamino, dialkylamino, thioyl, sulfonyl, sulfonamidyl, amido, urea, sulfonylurea acyl, nitro, cyano, cyclyl, heterocyclyl, aryl, or heteroaryl;

each $R^9$ is independently H, $C_1$-$C_6$ alkyl, $C_2$-$C_6$ alkenyl, or $C_2$-$C_6$ alkynyl, halo, hydroxyl, alkoxy, aryloxy, arylalkoxy, amino, akylamino, dialkylamino, thioyl, alkylthioyl, sulfonyl, sulfonamidyl, amido, urea, sulfonylurea, acyl, nitro, cyano, each of which is independently substituted with 1-3 $R^8$;

m is 1, 2, 3, 4, 5, or 6.

In another aspect, the invention features a method of treating an injury resulting from exposure to a chemical warfare agent in a subject, such as a human, the method comprising administering to the subject a compound of Formula (X) or a salt thereof Formula (X)

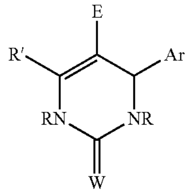

wherein

W represents O or S;

R, independently for each occurrence, represents H or lower alkyl;

R' represents substituted or unsubstituted alkyl or substituted or unsubstituted aryl;

E represents carboxylic acid ($CO_2H$), ester or amide; and

Ar represents a substituted or unsubstituted aryl ring.

Exemplary compounds of Formula X are described in WO 2007/073505.

In one aspect, the invention features a method of treating a subject who has been exposed to a chemical warfare agent, the method comprising administering to a subject an effective amount of a compound of Formula (II), (III), (IV), (V), (VI), (VII), (IX) or (X), or a salt thereof. In some embodiments the treatment reduces the severity of injury resulting from the exposure to the chemical warfare agent.

In some embodiments, the compound is administered orally, via intramuscular injection, by topical ocular administration, topically, or by inhalation. In some embodiments, the subject being treated is a human.

DETAILED DESCRIPTION OF THE INVENTION

Definitions

The term "acyl" refers to a group represented by the general formula hydrocarbylC(O)—, preferably alkylC(O)—.

The term "acylamino" refers to a moiety that can be represented by the general formula:

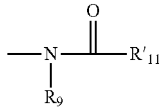

wherein $R_9$ is as defined below, and R'11 represents a hydrogen, an alkyl, an alkenyl or —(CH2)m-R8, where m and R8 are as defined herein.

The term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkenyl," as used herein, refers to an aliphatic group containing at least one double bond.

The terms "alkoxyl" or "alkoxy" as used herein refers to an alkyl group, as defined below, having an oxygen radical attached thereto. Representative alkoxyl groups include methoxy, ethoxy, propyloxy, tert-butoxy and the like. An "ether" is two hydrocarbons covalently linked by an oxygen.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., C1-C30 for straight chains, C3-C30 for branched chains), and more preferably 20 or fewer, and most preferably 10 or fewer. Likewise, preferred cycloalkyls have from 3-10 carbon atoms in their ring structure, and more preferably have 5, 6 or 7 carbons in the ring structure.

The term "alkynyl", as used herein, refers to an aliphatic group containing at least one triple bond.

The term "alkylthio" refers to a hydrocarbyl group having a sulfur radical attached thereto. In some embodiments, the "alkylthio" moiety is represented by one of —S-alkyl, —S—alkenyl, or —S-alkynyl. Representative alkylthio groups include methylthio, ethylthio, and the like.

The terms "amine" and "amino" refer to both unsubstituted and substituted amines, e.g., a moiety that can be represented by the general formula:

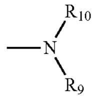

or

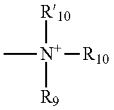

wherein $R_9$, $R_{10}$ and $R'_{10}$ each independently represent a hydrogen, an alkyl, an alkenyl, $—(CH_2)_m—R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, an alkoxy, a heterocycle or a polycycle; and m is zero or an integer in the range of 1 to 8.

The term "amido" refers to a moiety that can be represented by the general formula:

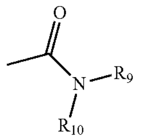

wherein $R_9$, $R_{10}$ are as defined above.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, polycyclyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle or cyclyl," as used herein, refers to an aromatic or non-aromatic ring in which each atom of the ring is carbon.

The term "carbonyl" refers to moieties represented by the general formula:

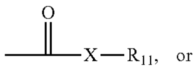 or 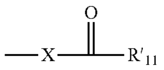

wherein X is a bond or represents an oxygen or a sulfur, and $R_{11}$ represents a hydrogen, an alkyl, an alkenyl, $-(CH_2)_m-R_8$ or a pharmaceutically acceptable counter-ion, $R'_{11}$ represents a hydrogen, an alkyl, an alkenyl or $-(CH_2)_m-R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "ester", as used herein, refers to a group $-C(O)OR^9$ wherein $R^9$ represents a hydrocarbyl group.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heterocyclyl" or "heterocyclic group" refer to 3- to 10-membered ring structures, more preferably 3- to 7-membered rings, whose ring structures include one to four heteroatoms. Heterocycles can also be polycycles. The term "heterocyclyl" or "heterocyclic group" includes "heteroaryl" and "saturated or partially saturated heterocyclyl" structures. The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). Any ring atom can be substituted (e.g., by one or more substituents). The term "saturated or partially saturated heterocyclyl" refers to a non-aromatic cylic structure that includes at least one heteroatom. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

As used herein, the term "nitro" means $-NO2$; the term "halogen" designates $-F$, $-Cl$, $-Br$ or $-I$; the term "sulfhydryl" means $-SH$; the term "hydroxyl" means $-OH$; and the term "sulfonyl" means $-SO2$-.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, $-CF3$, $-CN$, or the like.

Exemplary monocyclic rings include furan, thiophene, pyrrole, pyrroline, pyrrolodine, oxazole, thiazole, imidazole, imidazoline, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, and trithiane.

Exemplary bicyclic rings include indolizinyl, indolyl, isoindolyl, indolinyl, benzofuranyl, benzothiophenyl, indazolyl, benzimidazolyl, benthiazolyl, purinyl, quinolizinyl, quinolinyl, isoquinolinyl, cinnolinyl, phthalazinyl, quinazolinyl, quinoxalinyl, naphthyridinyl, pteridinyl, indenyl, naphthalenyl, azulenyl, imidazopyridazionyl, pyrazolopyrimidinedionyl, or pyrrolopyrimidinedionyl moieties.

Exemplary tricyclic rings include carbazole, acridine, phenazine, phenothiazine, phenoxazine, fluorine, and anthracene.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis,* $2^{nd}$ ed.; Wiley: New York, 1991).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), $-CF_3$, —CN and the like. Exemplary substituted alkyls are described below. Cycloalkyls can be further substituted with alkyls, alkenyls, alkoxys, alkylthios, aminoalkyls, carbonyl-substituted alkyls, $-CF_3$, —CN, and the like. Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "sulfate" refers to a moiety that can be represented by the general formula:

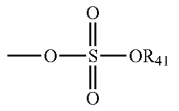

in which R41 is as defined herein.

The term "sulfonamido" refers to a moiety that can be represented by the general formula:

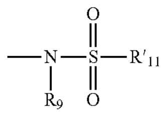

in which R9 and R'11 are as defined above.

The term "sulfonate" refers to a moiety that can be represented by the general formula:

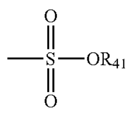

in which R41 is an electron pair, hydrogen, alkyl, cycloalkyl, or aryl.

The terms "sulfoxido" or "sulfinyl," as used herein, refers to a moiety that can be represented by the general formula —S(═O)—R44, in which R44 is selected from the group consisting of hydrogen, alkyl, alkenyl, alkynyl, cycloalkyl, heterocyclyl, aralkyl, or aryl.

The term "thioester," as used herein, refers to a group $-C(O)SR^9$ or $-SC(O)R^9$ wherein $R^9$ represents a hydrocarbyl.

As used herein, the definition of each expression, e.g., alkyl, m, n, etc., when it occurs more than once in any structure, is intended to be independent of its definition elsewhere in the same structure.

Exemplary monocyclic rings include furan, thiophene, pyrrole, pyrroline, pyrrolodine, oxazole, thiazole, imidazole, imidazoline, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, and trithiane.

Exemplary bicyclic rings include indolizinyl, indolyl, isoindolyl, indolinyl, benzofuranyl, benzothiophenyl, indazolyl, benzimidazolyl, benthiazolyl, purinyl, quinolizinyl, quinolinyl, isoquinolinyl, cinnolinyl, phthalazinyl, quinazolinyl, quinoxalinyl, naphthyridinyl, pteridinyl, indenyl, naphthalenyl, azulenyl, imidazopyridazionyl, pyrazolopyrimidinedionyl, or pyrrolopyrimidinedionyl moieties.

Exemplary tricyclic rings include carbazole, acridine, phenazine, phenothiazine, phenoxazine, fluorine, and anthracene.

The terms "antagonist" and "inhibitor" are used interchangeably to refer to an agent that decreases or suppresses a biological activity, such as to repress an activity of an ion channel, such as TRPA1. TRPA1 inhibitors include inhibitors having any combination of the structural and/or functional properties disclosed herein.

An "effective amount" of, e.g., a TRPA1 antagonist, with respect to the subject methods of treatment, refers to an amount of the antagonist in a preparation which, when applied as part of a desired dosage regimen brings about a desired clinical or functional result. Without being bound by theory, an effective amount of a TRPA1 antagonist for use in the methods of the present invention, includes an amount of a TRPA1 antagonist effective to decrease one or more in vitro or in vivo functions of a TRPA1 channel. Exemplary functions include, but are not limited to, membrane polarization (e.g., an antagonist may promote hyperpolarization of a cell), ion flux, ion concentration in a cell, outward current, and inward current. Compounds that antagonize TRPA1 function include compounds that antagonize an in vitro or in vivo functional activity of TRPA1. When a particular functional activity is only readily observable in an in vitro assay, the ability of a compound to inhibit TRPA1 function in that in vitro assay serves as a reasonable proxy for the activity of that compound. In certain embodiments, an effective amount is an amount sufficient to inhibit a TRPA1-mediated current and/or the amount sufficient to inhibit TRPA1 mediated ion flux.

The term "preventing," when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition or injury in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity in the host animal.

Exemplary compounds are provided in Table 1-7.

Compounds of Formula II include those shown in Table 1.

TABLE 1

| | |
|---|---|
| 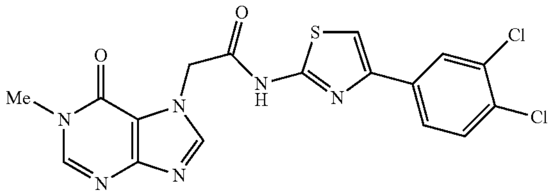 [SMILES: Cn1cnc2ncn(CC(=O)Nc3nc(-c4ccc(Cl)c(Cl)c4)cs3)c2c1=O] | N-(4-(3,4-dichlorophenyl)thiazol-2-yl)-2-(1-methyl-6-oxo-1H-purin-7(6H)-yl)acetamide |
| 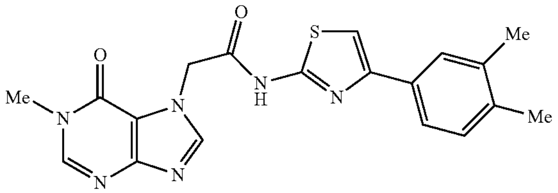 [SMILES: Cc1ccc(-c2csc(NC(=O)Cn3cnc4ncn(C)c(=O)c43)n2)cc1C] | N-(4-(3,4-dimethylphenyl)thiazol-2-yl)-2-(1-methyl-6-oxo-1H-purin-7(6H)-yl)acetamide |
| 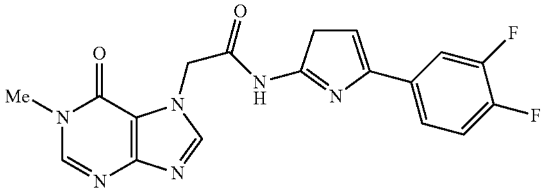 [SMILES: Cn1cnc2ncn(CC(=O)NC3=NC(c4ccc(F)c(F)c4)=CC3)c2c1=O] | N-(5-(3,4-difluorophenyl)-3H-pyrrol-2-yl)-2-(1-methyl-6-oxo-1H-purin-7(6H)-yl)acetamide |
| 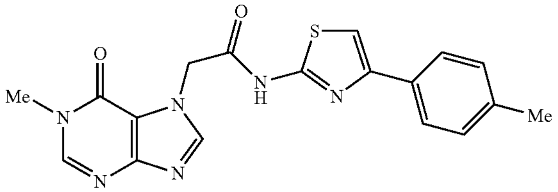 [SMILES: Cc1ccc(-c2csc(NC(=O)Cn3cnc4ncn(C)c(=O)c43)n2)cc1] | 2-(1-methyl-6-oxo-1H-purin-7(6H)-yl)-N-(4-p-tolylthiazol-2-yl)acetamide |
| 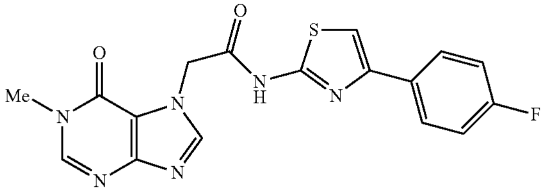 [SMILES: Cn1cnc2ncn(CC(=O)Nc3nc(-c4ccc(F)cc4)cs3)c2c1=O] | N-(4-(4-fluorophenyl)thiazol-2-yl)-2-(1-methyl-6-oxo-1H-purin-7(6H)-yl)acetamide |
| 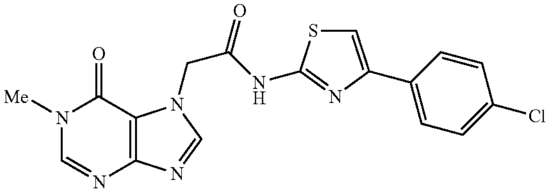 [SMILES: Cn1cnc2ncn(CC(=O)Nc3nc(-c4ccc(Cl)cc4)cs3)c2c1=O] | N-(4-(4-chlorophenyl)thiazol-2-yl)-2-(1-methyl-6-oxo-1H-purin-7(6H)-yl)acetamide |

TABLE 1-continued

| | |
|---|---|
| 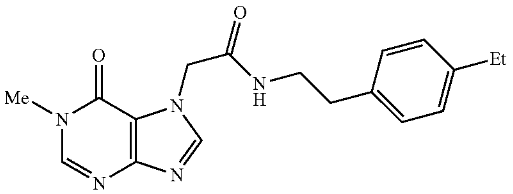 [SMILES: CCc1ccc(CCNC(=O)Cn2cnc3ncn(C)c(=O)c32)cc1] | N-(4-ethylphenethyl)-2-(1-methyl-6-oxo-1H-purin-7(6H)-yl)acetamide |
| 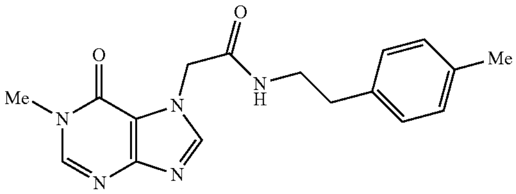 [SMILES: Cc1ccc(CCNC(=O)Cn2cnc3ncn(C)c(=O)c32)cc1] | 2-(1-methyl-6-oxo-1H-purin-7(6H)-yl)-N-(4-methylphenethyl)acetamide |
| 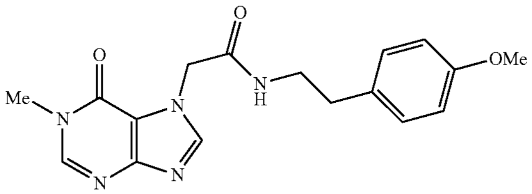 [SMILES: COc1ccc(CCNC(=O)Cn2cnc3ncn(C)c(=O)c32)cc1] | N-(4-methoxyphenethyl)-2-(1-methyl-6-oxo-1H-purin-7(6H)-yl)acetamide |
| 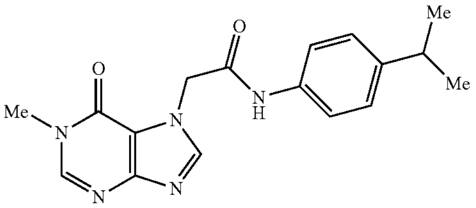 [SMILES: CC(C)c1ccc(NC(=O)Cn2cnc3ncn(C)c(=O)c32)cc1] | N-(4-isopropylphenyl)-2-(1-methyl-6-oxo-1H-purin-7(6H)-yl)acetamide |
| 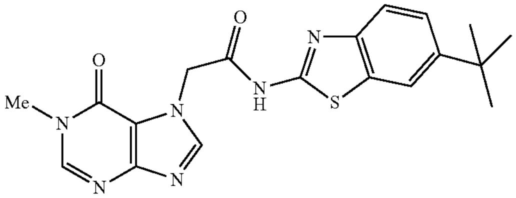 [SMILES: Cn1cnc2ncn(CC(=O)Nc3nc4ccc(C(C)(C)C)cc4s3)c2c1=O] | N-(6-tert-butylbenzo[d]thiazol-2-yl)-2-(1-methyl-6-oxo-1H-purin-7(6H)-yl)acetamide |
| 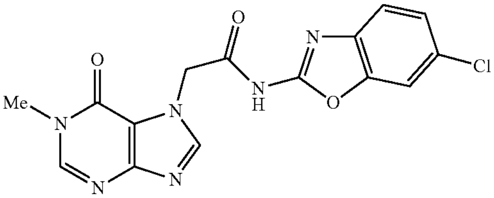 [SMILES: Cn1cnc2ncn(CC(=O)Nc3nc4ccc(Cl)cc4o3)c2c1=O] | N-(6-chlorobenzo[d]oxazol-2-yl)-2-(1-methyl-6-oxo-1H-purin-7(6H)-yl)acetamide |
| 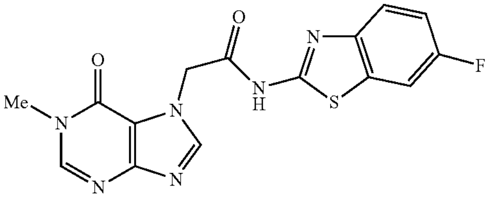 [SMILES: Cn1cnc2ncn(CC(=O)Nc3nc4ccc(F)cc4s3)c2c1=O] | N-(6-fluorobenzo[d]thiazol-2-yl)-2-(1-methyl-6-oxo-1H-purin-7(6H)-yl)acetamide |

TABLE 1-continued

| | |
|---|---|
| 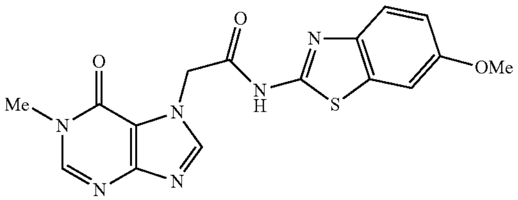 [SMILES: COc1ccc2nc(NC(=O)Cn3cnc4ncn(C)c(=O)c43)sc2c1] | N-(6-methoxybenzo[d]thiazol-2-yl)-2-(1-methyl-6-oxo-1H-purin-7(6H)-yl)acetamide |
| 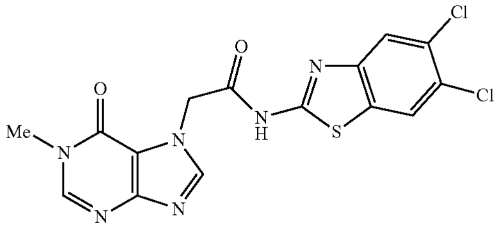 [SMILES: Cn1cnc2ncn(CC(=O)Nc3nc4cc(Cl)c(Cl)cc4s3)c2c1=O] | N-(5,6-dichlorobenzo[d]thiazol-2-yl)-2-(1-methyl-6-oxo-1H-purin-7(6H)-yl)acetamide |
| 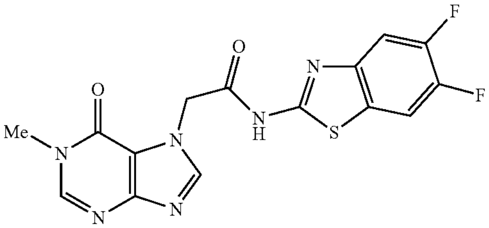 [SMILES: Cn1cnc2ncn(CC(=O)Nc3nc4cc(F)c(F)cc4s3)c2c1=O] | N-(5,6-difluorobenzo[d]thiazol-2-yl)-2-(1-methyl-6-oxo-1H-purin-7(6H)-yl)acetamide |
| 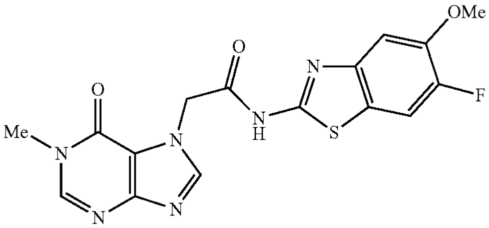 [SMILES: COc1cc2nc(NC(=O)Cn3cnc4ncn(C)c(=O)c43)sc2cc1F] | N-(6-fluoro-5-methoxybenzo[d]thiazol-2-yl)-2-(1-methyl-6-oxo-1H-purin-7(6H)-yl)acetamide |
| 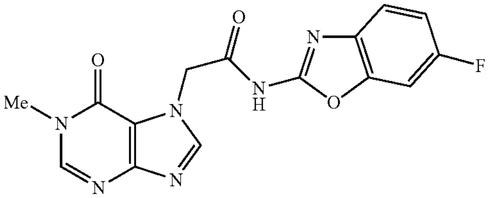 [SMILES: Cn1cnc2ncn(CC(=O)Nc3nc4ccc(F)cc4o3)c2c1=O] | N-(6-fluorobenzo[d]oxazol-2-yl)-2-(1-methyl-6-oxo-1H-purin-7(6H)-yl)acetamide |
| 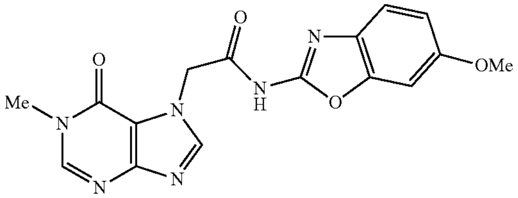 [SMILES: COc1ccc2nc(NC(=O)Cn3cnc4ncn(C)c(=O)c43)oc2c1] | N-(6-methoxybenzo[d]oxazol-2-yl)-2-(1-methyl-6-oxo-1H-purin-7(6H)-yl)acetamide |
| 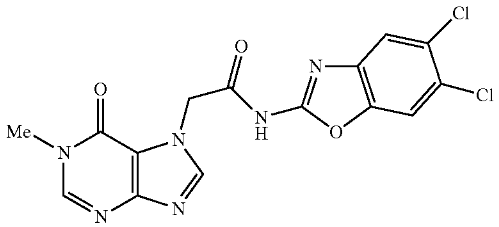 [SMILES: Cn1cnc2ncn(CC(=O)Nc3nc4cc(Cl)c(Cl)cc4o3)c2c1=O] | N-(5,6-dichlorobenzo[d]oxazol-2-yl)-2-(1-methyl-6-oxo-1H-purin-7(6H)-yl)acetamide |

TABLE 1-continued

| | |
|---|---|
| 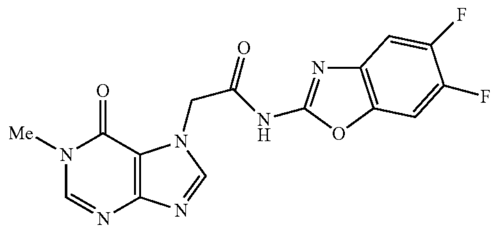 [SMILES: Cn1cnc2ncn(CC(=O)Nc3nc4cc(F)c(F)cc4o3)c2c1=O] | N-(5,6-difluorobenzo[d]oxazol-2-yl)-2-(1-methyl-6-oxo-1H-purin-7(6H)-yl)acetamide |
| 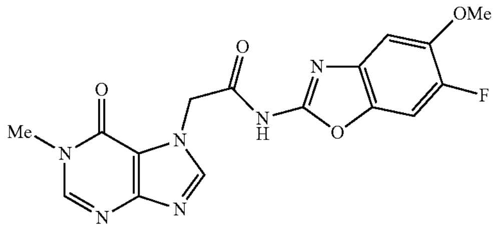 [SMILES: COc1cc2nc(NC(=O)Cn3cnc4ncn(C)c(=O)c43)oc2cc1F] | N-(6-fluoro-5-methoxybenzo[d]oxazol-2-yl)-2-(1-methyl-6-oxo-1H-purin-7(6H)-yl)acetamide |
| 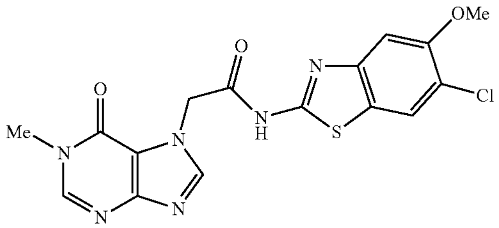 [SMILES: COc1cc2nc(NC(=O)Cn3cnc4ncn(C)c(=O)c43)sc2cc1Cl] | N-(6-chloro-5-methoxybenzo[d]thiazol-2-yl)-2-(1,3-dimethyl-2,6-dioxo-2,3-dihydro-1H-purin-7(6H)-yl)acetamide |
| 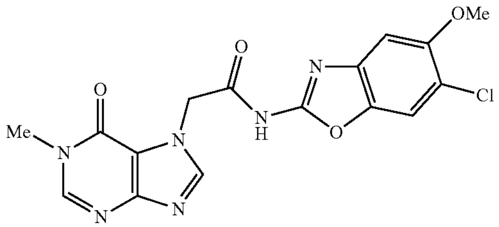 [SMILES: COc1cc2nc(NC(=O)Cn3cnc4ncn(C)c(=O)c43)oc2cc1Cl] | N-(6-chloro-5-methoxybenzo[d]oxazol-2-yl)-2-(1,3-dimethyl-2,6-dioxo-2,3-dihydro-1H-purin-7(6H)-yl)acetamide |
| 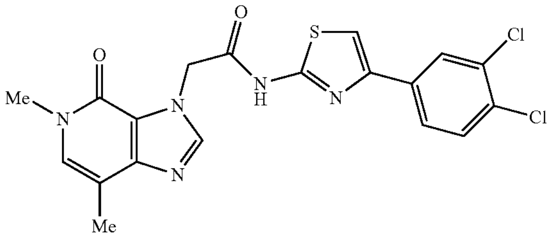 [SMILES: Cc1cn(C)c(=O)c2c1ncn2CC(=O)Nc1nc(-c2ccc(Cl)c(Cl)c2)cs1] | N-(4-(3,4-dichlorophenyl)thiazol-2-yl)-2-(5,7-dimethyl-4-oxo-4,5-dihydro-3H-imidazo[4,5-c]pyridin-3-yl)acetamide |
| 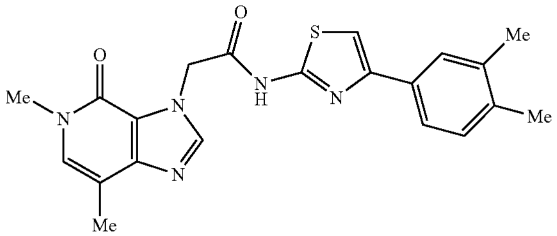 [SMILES: Cc1ccc(-c2csc(NC(=O)Cn3cnc4c(C)cn(C)c(=O)c43)n2)cc1C] | 2-(5,7-dimethyl-4-oxo-4,5-dihydro-3H-imidazo[4,5-c]pyridin-3-yl)-N-(4-(3,4-dimethylphenyl)thiazol-2-yl)acetamide |

TABLE 1-continued

| | |
|---|---|
| 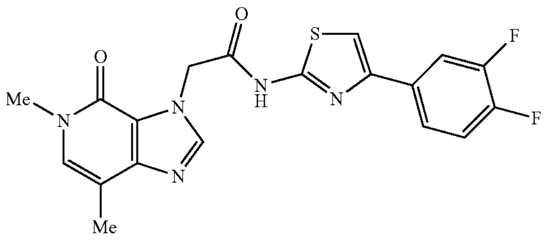 [SMILES: Cc1cn(C)c(=O)c2c1ncn2CC(=O)Nc1nc(-c2ccc(F)c(F)c2)cs1] | N-(4-(3,4-difluorophenyl)thiazol-2-yl)-2-(5,7-dimethyl-4-oxo-4,5-dihydro-3H-imidazo[4,5-c]pyridin-3-yl)acetamide |
| 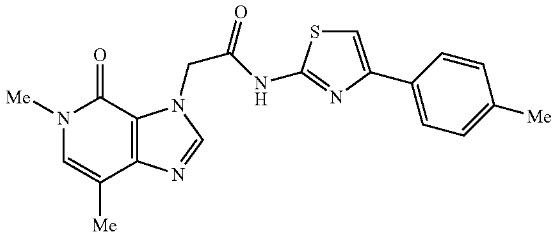 [SMILES: Cc1ccc(-c2csc(NC(=O)Cn3cnc4c(C)cn(C)c(=O)c43)n2)cc1] | 2-(5,7-dimethyl-4-oxo-4,5-dihydro-3H-imidazo[4,5-c]pyridin-3-yl)-N-(4-p-tolylthiazol-2-yl)acetamide |
| 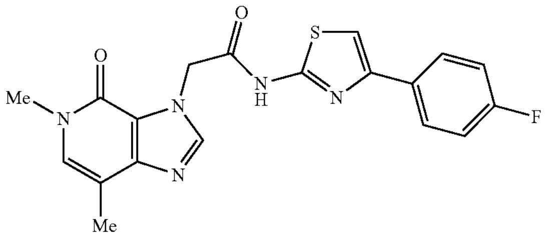 [SMILES: Cc1cn(C)c(=O)c2c1ncn2CC(=O)Nc1nc(-c2ccc(F)cc2)cs1] | 2-(5,7-dimethyl-4-oxo-4,5-dihydro-3H-imidazo[4,5-c]pyridin-3-yl)-N-(4-(4-fluorophenyl)thiazol-2-yl)acetamide |
| 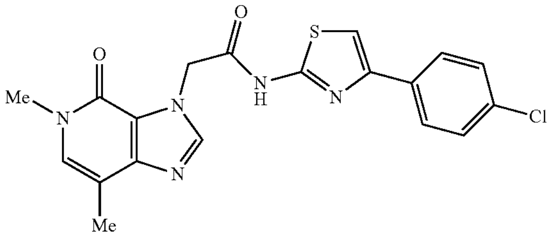 [SMILES: Cc1cn(C)c(=O)c2c1ncn2CC(=O)Nc1nc(-c2ccc(Cl)cc2)cs1] | N-(4-(4-chlorophenyl)thiazol-2-yl)-2-(5,7-dimethyl-4-oxo-4,5-dihydro-3H-imidazo[4,5-c]pyridin-3-yl)acetamide |
| 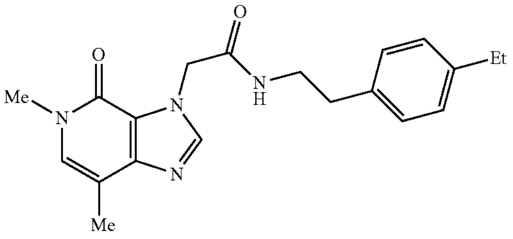 [SMILES: CCc1ccc(CCNC(=O)Cn2cnc3c(C)cn(C)c(=O)c32)cc1] | 2-(5,7-dimethyl-4-oxo-4,5-dihydro-3H-imidazo[4,5-c]pyridin-3-yl)-N-(4-ethylphenethyl)acetamide |
| 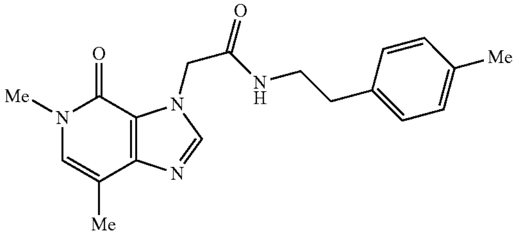 [SMILES: Cc1ccc(CCNC(=O)Cn2cnc3c(C)cn(C)c(=O)c32)cc1] | 2-(5,7-dimethyl-4-oxo-4,5-dihydro-3H-imidazo[4,5-c]pyridin-3-yl)-N-(4-methylphenethyl)acetamide |

TABLE 1-continued

| | |
|---|---|
| 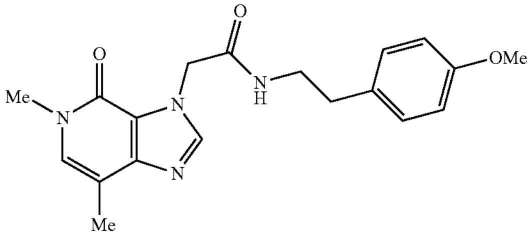 [SMILES: COc1ccc(CCNC(=O)Cn2cnc3c(C)cn(C)c(=O)c32)cc1] | 2-(5,7-dimethyl-4-oxo-4,5-dihydro-3H-imidazo[4,5-c]pyridin-3-yl)-N-(4-methoxyphenethyl)acetamide |
| 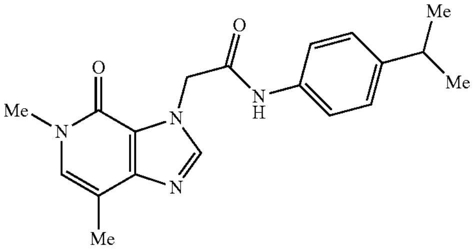 [SMILES: Cc1cn(C)c(=O)c2c1ncn2CC(=O)Nc1ccc(C(C)C)cc1] | 2-(5,7-dimethyl-4-oxo-4,5-dihydro-3H-imidazo[4,5-c]pyridin-3-yl)-N-(4-isopropylphenyl)acetamide |
| 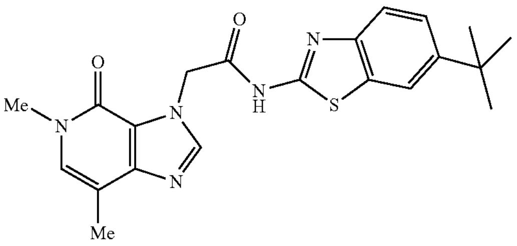 [SMILES: Cc1cn(C)c(=O)c2c1ncn2CC(=O)Nc1nc2ccc(C(C)(C)C)cc2s1] | N-(6-tert-butylbenzo[d]thiazol-2-yl)-2-(5,7-dimethyl-4-oxo-4,5-dihydro-3H-imidazo[4,5-c]pyridin-3-yl)acetamide |
| 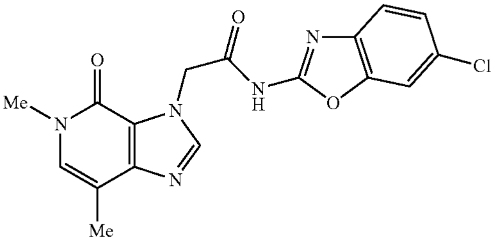 [SMILES: Cc1cn(C)c(=O)c2c1ncn2CC(=O)Nc1nc2ccc(Cl)cc2o1] | N-(6-chlorobenzo[d]oxazol-2-yl)-2-(5,7-dimethyl-4-oxo-4,5-dihydro-3H-imidazo[4,5-c]pyridin-3-yl)acetamide |
| 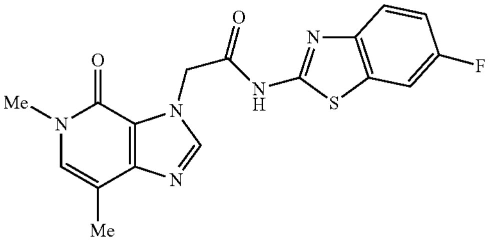 [SMILES: Cc1cn(C)c(=O)c2c1ncn2CC(=O)Nc1nc2ccc(F)cc2s1] | 2-(5,7-dimethyl-4-oxo-4,5-dihydro-3H-imidazo[4,5-c]pyridin-3-yl)-N-(6-fluorobenzo[d]thiazol-2-yl)acetamide |
| 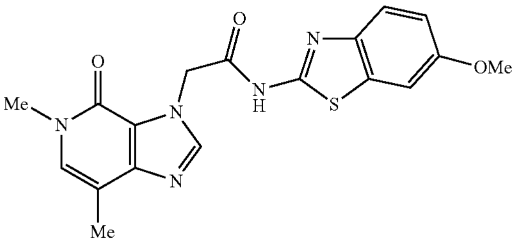 [SMILES: COc1ccc2nc(NC(=O)Cn3cnc4c(C)cn(C)c(=O)c43)sc2c1] | 2-(5,7-dimethyl-4-oxo-4,5-dihydro-3H-imidazo[4,5-c]pyridin-3-yl)-N-(6-methoxybenzo[d]thiazol-2-yl)acetamide |

TABLE 1-continued

| | |
|---|---|
| 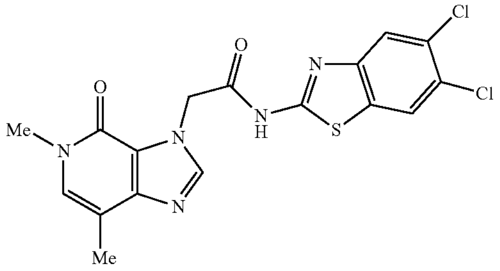 [SMILES: Cc1cn(C)c(=O)c2c1ncn2CC(=O)Nc1nc2cc(Cl)c(Cl)cc2s1] | N-(5,6-dichlorobenzo[d]thiazol-2-yl)-2-(5,7-dimethyl-4-oxo-4,5-dihydro-3H-imidazo[4,5-c]pyridin-3-yl)acetamide |
| 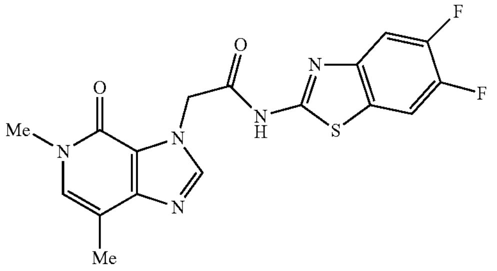 [SMILES: Cc1cn(C)c(=O)c2c1ncn2CC(=O)Nc1nc2cc(F)c(F)cc2s1] | N-(5,6-difluorobenzo[d]thiazol-2-yl)-2-(5,7-dimethyl-4-oxo-4,5-dihydro-3H-imidazo[4,5-c]pyridin-3-yl)acetamide |
| 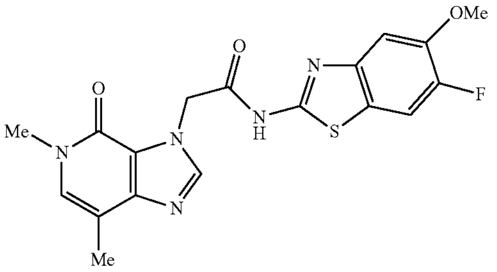 [SMILES: COc1cc2nc(NC(=O)Cn3cnc4c(C)cn(C)c(=O)c43)sc2cc1F] | 2-(5,7-dimethyl-4-oxo-4,5-dihydro-3H-imidazo[4,5-c]pyridin-3-yl)-N-(6-fluoro-5-methoxybenzo[d]thiazol-2-yl)acetamide |
| 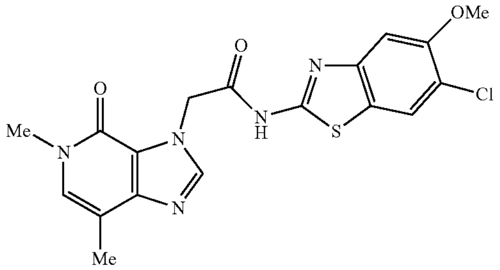 [SMILES: COc1cc2nc(NC(=O)Cn3cnc4c(C)cn(C)c(=O)c43)sc2cc1Cl] | N-(6-chloro-5-methoxybenzo[d]thiazol-2-yl)-2-(5,7-dimethyl-4-oxo-4,5-dihydro-3H-imidazo[4,5-c]pyridin-3-yl)acetamide |
| 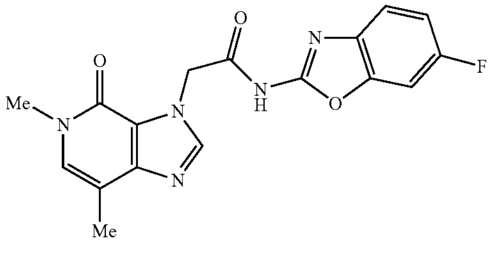 [SMILES: Cc1cn(C)c(=O)c2c1ncn2CC(=O)Nc1nc2ccc(F)cc2o1] | 2-(5,7-dimethyl-4-oxo-4,5-dihydro-3H-imidazo[4,5-c]pyridin-3-yl)-N-(6-fluorobenzo[d]oxazol-2-yl)acetamide |
| 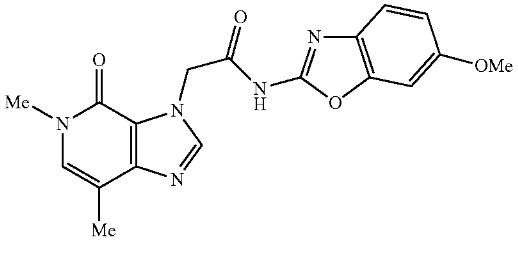 [SMILES: COc1ccc2nc(NC(=O)Cn3cnc4c(C)cn(C)c(=O)c43)oc2c1] | 2-(5,7-dimethyl-4-oxo-4,5-dihydro-3H-imidazo[4,5-c]pyridin-3-yl)-N-(6-methoxybenzo[d]oxazol-2-yl)acetamide |

TABLE 1-continued

| | |
|---|---|
| 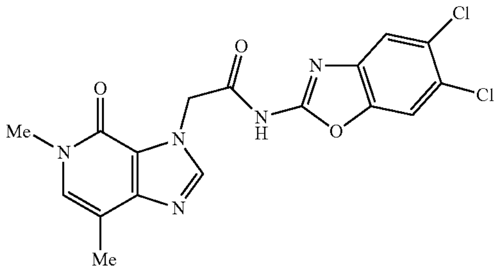 [SMILES: Cc1cn(C)c(=O)c2c1ncn2CC(=O)Nc1nc2cc(Cl)c(Cl)cc2o1] | N-(5,6-dichlorobenzo[d]oxazol-2-yl)-2-(5,7-dimethyl-4-oxo-4,5-dihydro-3H-imidazo[4,5-c]pyridin-3-yl)acetamide |
| 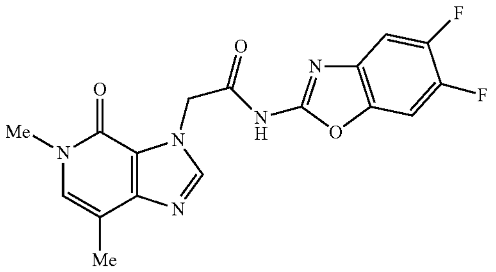 [SMILES: Cc1cn(C)c(=O)c2c1ncn2CC(=O)Nc1nc2cc(F)c(F)cc2o1] | N-(5,6-difluorobenzo[d]oxazol-2-yl)-2-(5,7-dimethyl-4-oxo-4,5-dihydro-3H-imidazo[4,5-c]pyridin-3-yl)acetamide |
| 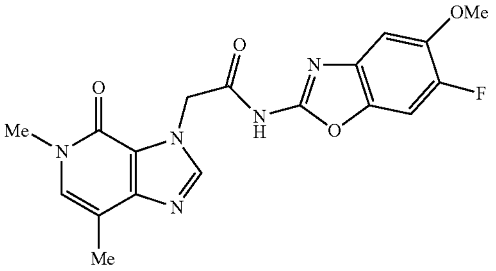 [SMILES: COc1cc2nc(NC(=O)Cn3cnc4c(C)cn(C)c(=O)c43)oc2cc1F] | 2-(5,7-dimethyl-4-oxo-4,5-dihydro-3H-imidazo[4,5-c]pyridin-3-yl)-N-(6-fluoro-5-methoxybenzo[d]oxazol-2-yl)acetamide |
| 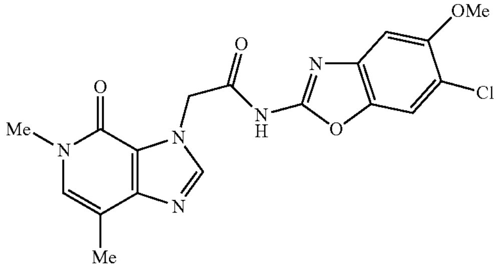 [SMILES: COc1cc2nc(NC(=O)Cn3cnc4c(C)cn(C)c(=O)c43)oc2cc1Cl] | N-(6-chloro-5-methoxybenzo[d]oxazol-2-yl)-2-(5,7-dimethyl-4-oxo-4,5-dihydro-3H-imidazo[4,5-c]pyridin-3-yl)acetamide |
| 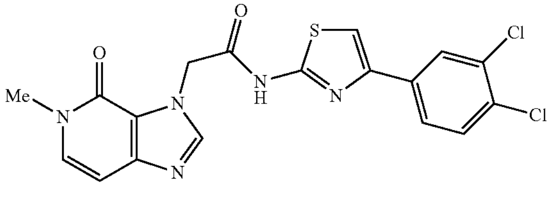 [SMILES: Cn1ccc2ncn(CC(=O)Nc3nc(-c4ccc(Cl)c(Cl)c4)cs3)c2c1=O] | N-(4-(3,4-dichlorophenyl)thiazol-2-yl)-2-(5-methyl-4-oxo-4,5-dihydro-3H-imidazo[4,5-c]pyridin-3-yl)acetamide |
| 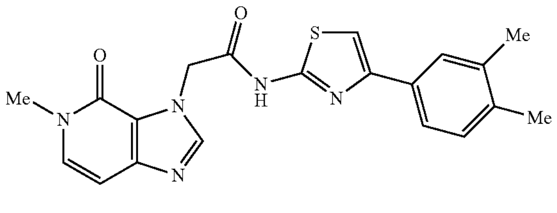 [SMILES: Cc1ccc(-c2csc(NC(=O)Cn3cnc4ccn(C)c(=O)c43)n2)cc1C] | N-(4-(3,4-dimethylphenyl)thiazol-2-yl)-2-(5-methyl-4-oxo-4,5-dihydro-3H-imidazo[4,5-c]pyridin-3-yl)acetamide |

TABLE 1-continued

| | |
|---|---|
| 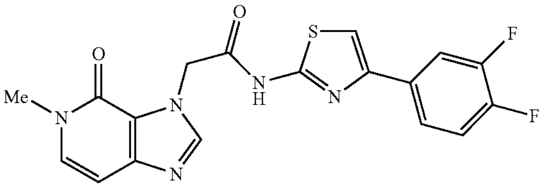 [SMILES: Cn1ccc2ncn(CC(=O)Nc3nc(-c4ccc(F)c(F)c4)cs3)c2c1=O] | N-(4-(3,4-difluorophenyl)thiazol-2-yl)-2-(5-methyl-4-oxo-4,5-dihydro-3H-imidazo[4,5-c]pyridin-3-yl)acetamide |
| 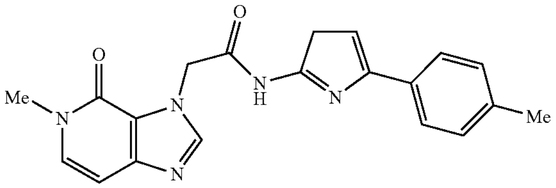 [SMILES: Cc1ccc(C2=CCC(NC(=O)Cn3cnc4ccn(C)c(=O)c43)=N2)cc1] | 2-(5-methyl-4-oxo-4,5-dihydro-3H-imidazo[4,5-c]pyridin-3-yl)-N-(5-p-tolyl-3H-pyrrol-2-yl)acetamide |
| 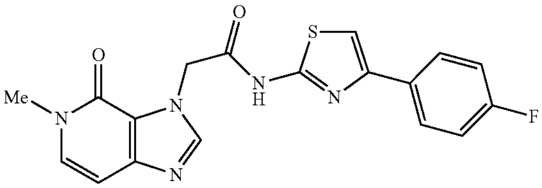 [SMILES: Cn1ccc2ncn(CC(=O)Nc3nc(-c4ccc(F)cc4)cs3)c2c1=O] | N-(4-(4-fluorophenyl)thiazol-2-yl)-2-(5-methyl-4-oxo-4,5-dihydro-3H-imidazo[4,5-c]pyridin-3-yl)acetamide |
| 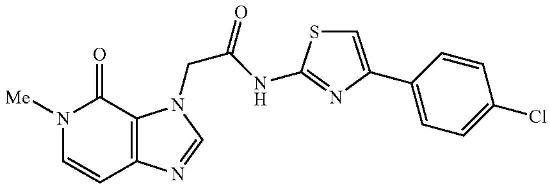 [SMILES: Cn1ccc2ncn(CC(=O)Nc3nc(-c4ccc(Cl)cc4)cs3)c2c1=O] | N-(4-(4-chlorophenyl)thiazol-2-yl)-2-(5-methyl-4-oxo-4,5-dihydro-3H-imidazo[4,5-c]pyridin-3-yl)acetamide |
| 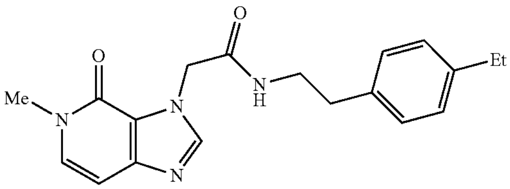 [SMILES: CCc1ccc(CCNC(=O)Cn2cnc3ccn(C)c(=O)c32)cc1] | N-(4-ethylphenethyl)-2-(5-methyl-4-oxo-4,5-dihydro-3H-imidazo[4,5-c]pyridin-3-yl)acetamide |
| 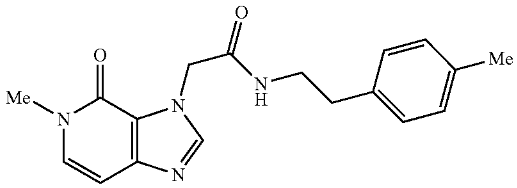 [SMILES: Cc1ccc(CCNC(=O)Cn2cnc3ccn(C)c(=O)c32)cc1] | 2-(5-methyl-4-oxo-4,5-dihydro-3H-imidazo[4,5-c]pyridin-3-yl)-N-(4-methylphenethyl)acetamide |
| 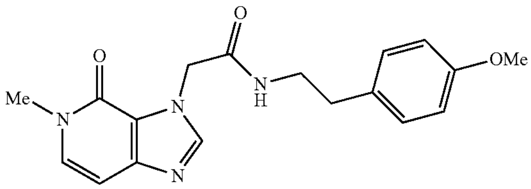 [SMILES: COc1ccc(CCNC(=O)Cn2cnc3ccn(C)c(=O)c32)cc1] | N-(4-methoxyphenethyl)-2-(5-methyl-4-oxo-4,5-dihydro-3H-imidazo[4,5-c]pyridin-3-yl)acetamide |
| 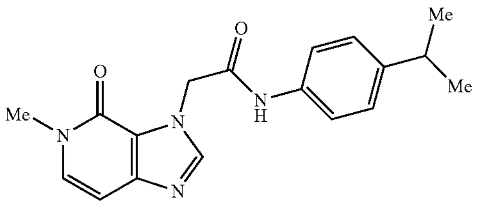 [SMILES: CC(C)c1ccc(NC(=O)Cn2cnc3ccn(C)c(=O)c32)cc1] | N-(4-isopropylphenyl)-2-(5-methyl-4-oxo-4,5-dihydro-3H-imidazo[4,5-c]pyridin-3-yl)acetamide |

TABLE 1-continued

| | |
|---|---|
| 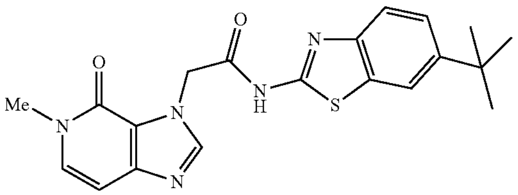 [SMILES: Cn1ccc2ncn(CC(=O)Nc3nc4ccc(C(C)(C)C)cc4s3)c2c1=O] | N-(6-tert-butylbenzo[d]thiazol-2-yl)-2-(5-methyl-4-oxo-4,5-dihydro-3H-imidazo[4,5-c]pyridin-3-yl)acetamide |
| 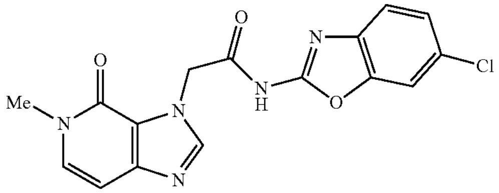 [SMILES: Cn1ccc2ncn(CC(=O)Nc3nc4ccc(Cl)cc4o3)c2c1=O] | N-(6-chlorobenzo[d]oxazol-2-yl)-2-(5-methyl-4-oxo-4,5-dihydro-3H-imidazo[4,5-c]pyridin-3-yl)acetamide |
| 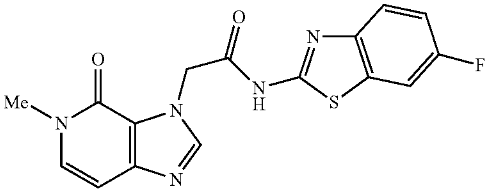 [SMILES: Cn1ccc2ncn(CC(=O)Nc3nc4ccc(F)cc4s3)c2c1=O] | N-(6-fluorobenzo[d]thiazol-2-yl)-2-(5-methyl-4-oxo-4,5-dihydro-3H-imidazo[4,5-c]pyridin-3-yl)acetamide |
| 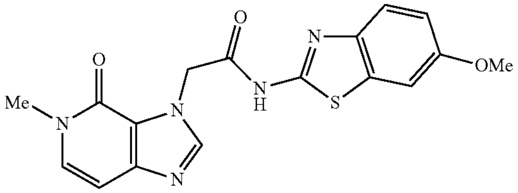 [SMILES: COc1ccc2nc(NC(=O)Cn3cnc4ccn(C)c(=O)c43)sc2c1] | N-(6-methoxybenzo[d]thiazol-2-yl)-2-(5-methyl-4-oxo-4,5-dihydro-3H-imidazo[4,5-c]pyridin-3-yl)acetamide |
| 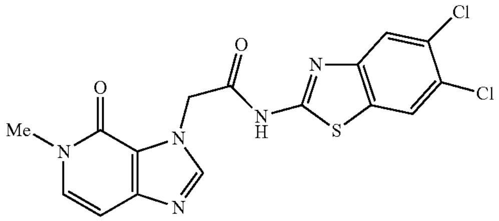 [SMILES: Cn1ccc2ncn(CC(=O)Nc3nc4cc(Cl)c(Cl)cc4s3)c2c1=O] | N-(5,6-dichlorobenzo[d]thiazol-2-yl)-2-(5-methyl-4-oxo-4,5-dihydro-3H-imidazo[4,5-c]pyridin-3-yl)acetamide |
| 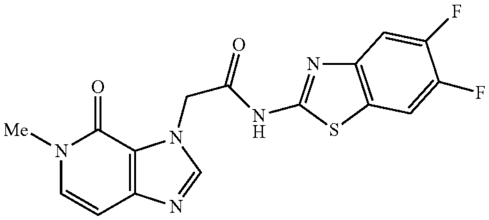 [SMILES: Cn1ccc2ncn(CC(=O)Nc3nc4cc(F)c(F)cc4s3)c2c1=O] | N-(5,6-difluorobenzo[d]thiazol-2-yl)-2-(5-methyl-4-oxo-4,5-dihydro-3H-imidazo[4,5-c]pyridin-3-yl)acetamide |
| 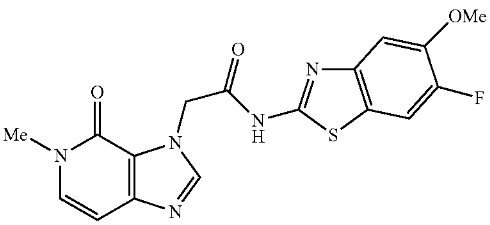 [SMILES: COc1cc2nc(NC(=O)Cn3cnc4ccn(C)c(=O)c43)sc2cc1F] | N-(6-fluoro-5-methoxybenzo[d]thiazol-2-yl)-2-(5-methyl-4-oxo-4,5-dihydro-3H-imidazo[4,5-c]pyridin-3-yl)acetamide |

TABLE 1-continued

| | |
|---|---|
| 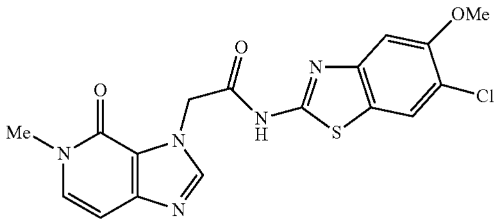 [SMILES: COc1cc2nc(NC(=O)Cn3cnc4ccn(C)c(=O)c43)sc2cc1Cl] | N-(6-chloro-5-methoxybenzo[d]thiazol-2-yl)-2-(5-methyl-4-oxo-4,5-dihydro-3H-imidazo[4,5-c]pyridin-3-yl)acetamide |
| 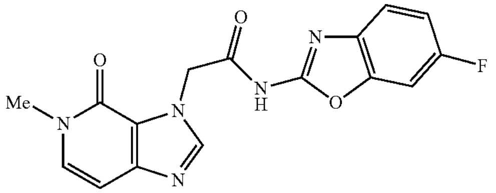 [SMILES: Cn1ccc2ncn(CC(=O)Nc3nc4ccc(F)cc4o3)c2c1=O] | N-(6-fluorobenzo[d]oxazol-2-yl)-2-(5-methyl-4-oxo-4,5-dihydro-3H-imidazo[4,5-c]pyridin-3-yl)acetamide |
| 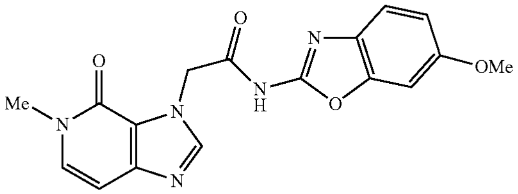 [SMILES: COc1ccc2nc(NC(=O)Cn3cnc4ccn(C)c(=O)c43)oc2c1] | N-(6-methoxybenzo[d]oxazol-2-yl)-2-(5-methyl-4-oxo-4,5-dihydro-3H-imidazo[4,5-c]pyridin-3-yl)acetamide |
| 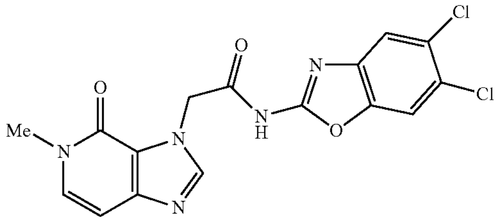 [SMILES: Cn1ccc2ncn(CC(=O)Nc3nc4cc(Cl)c(Cl)cc4o3)c2c1=O] | N-(5,6-dichlorobenzo[d]oxazol-2-yl)-2-(5-methyl-4-oxo-4,5-dihydro-3H-imidazo[4,5-c]pyridin-3-yl)acetamide |
| 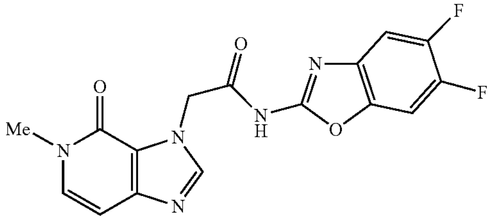 [SMILES: Cn1ccc2ncn(CC(=O)Nc3nc4cc(F)c(F)cc4o3)c2c1=O] | N-(5,6-difluorobenzo[d]oxazol-2-yl)-2-(5-methyl-4-oxo-4,5-dihydro-3H-imidazo[4,5-c]pyridin-3-yl)acetamide |
| 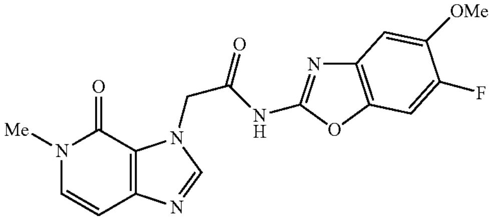 | N-(6-fluoro-5-methoxybenzo[d]oxazol-2-yl)-2-(5-methyl-4-oxo-4,5-dihydro-3H-imidazo[4,5-c]pyridin-3-yl)acetamide |
| 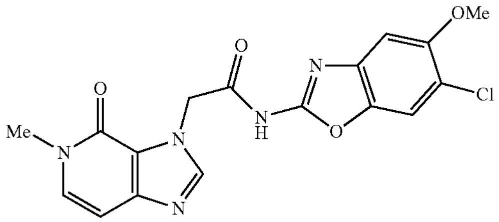 | N-(6-chloro-5-methoxybenzo[d]oxazol-2-yl)-2-(5-methyl-4-oxo-4,5-dihydro-3H-imidazo[4,5-c]pyridin-3-yl)acetamide |

Compounds of Formula III include those shown in Table 2.

TABLE 2

| | |
|---|---|
| 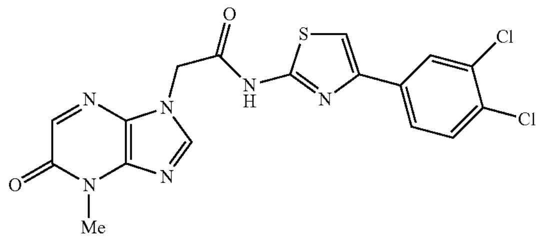 [SMILES: Cn1c(=O)cnc2c1ncn2CC(=O)Nc1nc(-c2ccc(Cl)c(Cl)c2)cs1] | N-(4-(3,4-dichlorophenyl)thiazol-2-yl)-2-(4-methyl-5-oxo-4,5-dihydro-1H-imidazo[4,5-b]pyrazin-1-yl)acetamide |
| 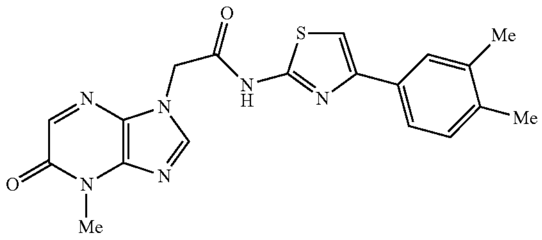 [SMILES: Cc1ccc(-c2csc(NC(=O)Cn3cnc4c3ncc(=O)n4C)n2)cc1C] | N-(4-(3,4-dimethylphenyl)thiazol-2-yl)-2-(4-methyl-5-oxo-4,5-dihydro-1H-imidazo[4,5-b]pyrazin-1-yl)acetamide |
| 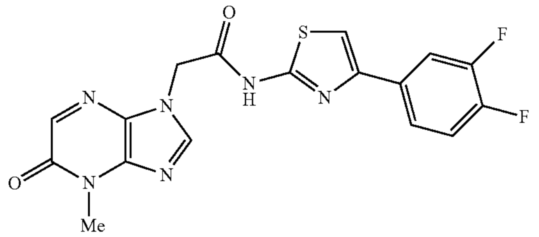 | N-(4-(3,4-difluorophenyl)thiazol-2-yl)-2-(4-methyl-5-oxo-4,5-dihydro-1H-imidazo[4,5-b]pyrazin-1-yl)acetamide |
| 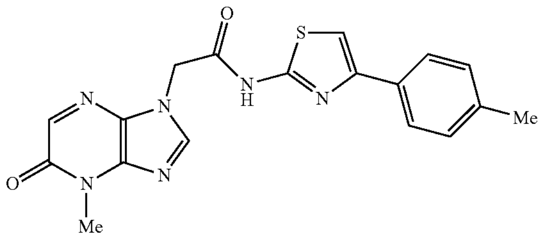 [SMILES: Cc1ccc(-c2csc(NC(=O)Cn3cnc4c3ncc(=O)n4C)n2)cc1] | 2-(4-methyl-5-oxo-4,5-dihydro-1H-imidazo[4,5-b]pyrazin-1-yl)-N-(4-p-tolylthiazol-2-yl)acetamide |
| 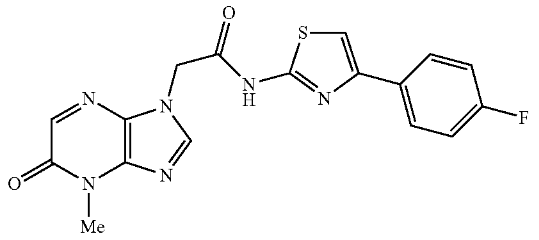 [SMILES: Cn1c(=O)cnc2c1ncn2CC(=O)Nc1nc(-c2ccc(F)cc2)cs1] | N-(4-(4-fluorophenyl)thiazol-2-yl)-2-(4-methyl-5-oxo-4,5-dihydro-1H-imidazo[4,5-b]pyrazin-1-yl)acetamide |
| 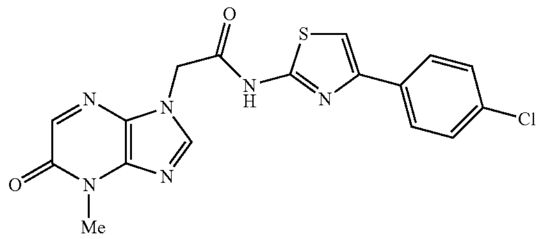 [SMILES: Cn1c(=O)cnc2c1ncn2CC(=O)Nc1nc(-c2ccc(Cl)cc2)cs1] | N-(4-(4-chlorophenyl)thiazol-2-yl)-2-(4-methyl-5-oxo-4,5-dihydro-1H-imidazo[4,5-b]pyrazin-1-yl)acetamide |

TABLE 2-continued

| | |
|---|---|
| 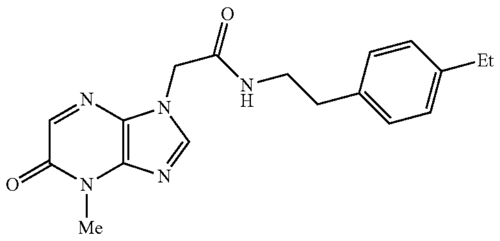 [SMILES: CCc1ccc(CCNC(=O)Cn2cnc3c2ncc(=O)n3C)cc1] | N-(4-ethylphenethyl)-2-(4-methyl-5-oxo-4,5-dihydro-1H-imidazo[4,5-b]pyrazin-1-yl)acetamide |
| 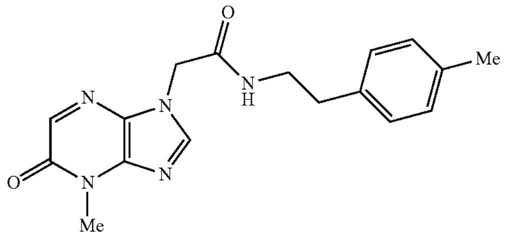 [SMILES: Cc1ccc(CCNC(=O)Cn2cnc3c2ncc(=O)n3C)cc1] | 2-(4-methyl-5-oxo-4,5-dihydro-1H-imidazo[4,5-b]pyrazin-1-yl)-N-(4-methylphenethyl)acetamide |
| 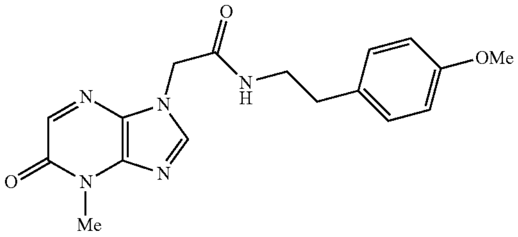 [SMILES: COc1ccc(CCNC(=O)Cn2cnc3c2ncc(=O)n3C)cc1] | N-(4-methoxyphenethyl)-2-(4-methyl-5-oxo-4,5-dihydro-1H-imidazo[4,5-b]pyrazin-1-yl)acetamide |
| 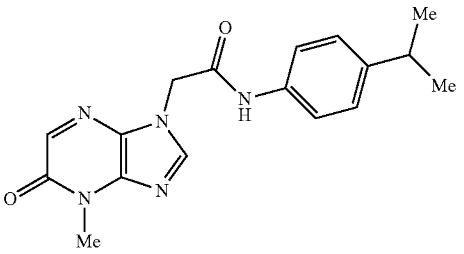 [SMILES: CC(C)c1ccc(NC(=O)Cn2cnc3c2ncc(=O)n3C)cc1] | N-(4-isopropylphenyl)-2-(4-methyl-5-oxo-4,5-dihydro-1H-imidazo[4,5-b]pyrazin-1-yl)acetamide |
| 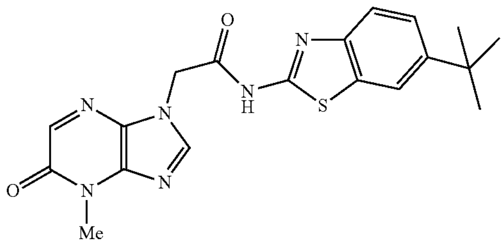 [SMILES: Cn1c(=O)cnc2c1ncn2CC(=O)Nc1nc2ccc(C(C)(C)C)cc2s1] | N-(6-tert-butylbenzo[d]thiazol-2-yl)-2-(4-methyl-5-oxo-4,5-dihydro-1H-imidazo[4,5-b]pyrazin-1-yl)acetamide |
| 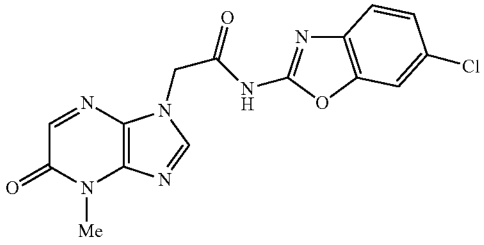 [SMILES: Cn1c(=O)cnc2c1ncn2CC(=O)Nc1nc2ccc(Cl)cc2o1] | N-(6-chlorobenzo[d]oxazol-2-yl)-2-(4-methyl-5-oxo-4,5-dihydro-1H-imidazo[4,5-b]pyrazin-1-yl)acetamide |

TABLE 2-continued

| | |
|---|---|
| 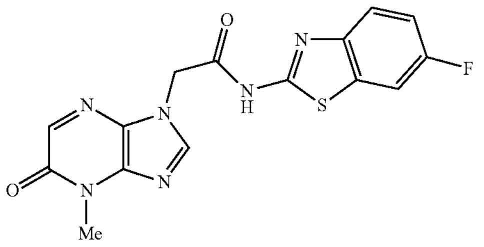 | N-(6-fluorobenzo[d]thiazol-2-yl)-2-(4-methyl-5-oxo-4,5-dihydro-1H-imidazo[4,5-b]pyridin-1-yl)acetamide |
| 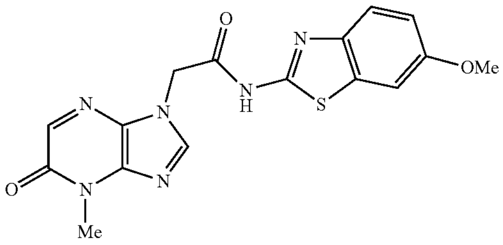 [SMILES: COc1ccc2nc(NC(=O)Cn3cnc4c3ncc(=O)n4C)sc2c1] | N-(6-methoxybenzo[d]thiazol-2-yl)-2-(4-methyl-5-oxo-4,5-dihydro-1H-imidazo[4,5-b]pyridin-1-yl)acetamide |
| 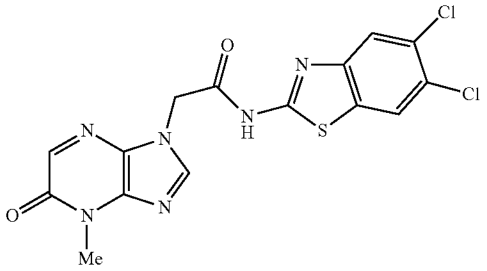 [SMILES: Cn1c(=O)cnc2c1ncn2CC(=O)Nc1nc2cc(Cl)c(Cl)cc2s1] | N-(5,6-dichlorobenzo[d]thiazol-2-yl)-2-(4-methyl-5-oxo-4,5-dihydro-1H-imidazo[4,5-b]pyridin-1-yl)acetamide |
| 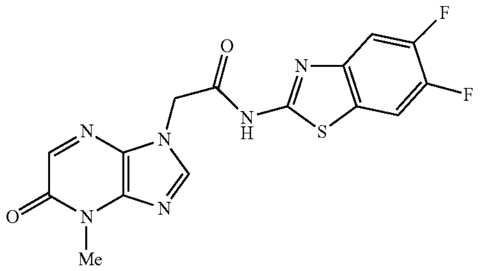 [SMILES: Cn1c(=O)cnc2c1ncn2CC(=O)Nc1nc2cc(F)c(F)cc2s1] | N-(5,6-difluorobenzo[d]thiazol-2-yl)-2-(4-methyl-5-oxo-4,5-dihydro-1H-imidazo[4,5-b]pyridin-1-yl)acetamide |
| 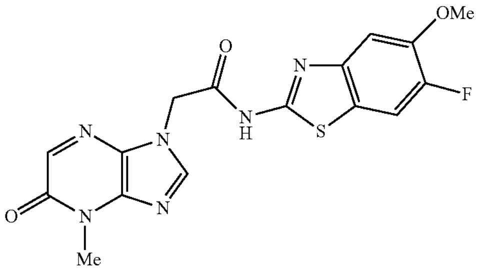 | N-(6-fluoro-5-methoxybenzo[d]thiazol-2-yl)-2-(4-methyl-5-oxo-4,5-dihydro-1H-imidazo[4,5-b]pyridin-1-yl)acetamide |
| 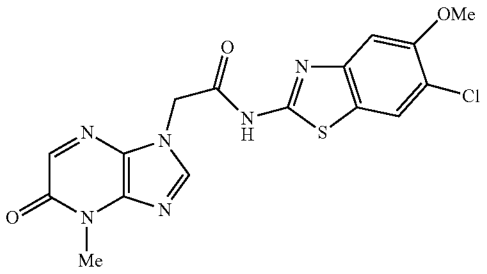 | N-(6-chloro-5-methoxybenzo[d]thiazol-2-yl)-2-(4-methyl-5-oxo-4,5-dihydro-1H-imidazo[4,5-b]pyridin-1-yl)acetamide |

TABLE 2-continued

| | |
|---|---|
| 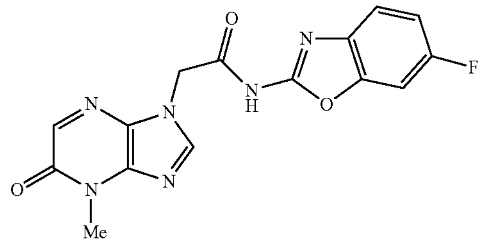 [SMILES: Cn1c(=O)cnc2c1ncn2CC(=O)Nc1nc2ccc(F)cc2o1] | N-(6-fluorobenzo[d]oxazol-2-yl)-2-(4-methyl-5-oxo-4,5-dihydro-1H-imidazo[4,5-b]pyridin-1-yl)acetamide |
| 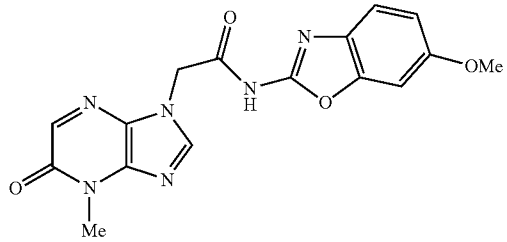 | N-(6-methoxybenzo[d]oxazol-2-yl)-2-(4-methyl-5-oxo-4,5-dihydro-1H-imidazo[4,5-b]pyridin-1-yl)acetamide |
| 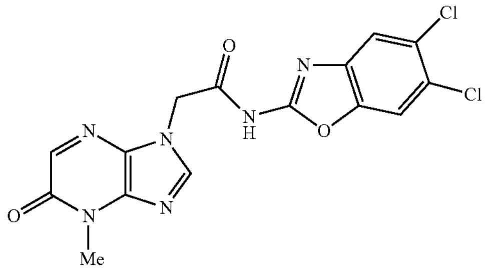 | N-(5,6-dichlorobenzo[d]oxazol-2-yl)-2-(4-methyl-5-oxo-4,5-dihydro-1H-imidazo[4,5-b]pyridin-1-yl)acetamide |
| 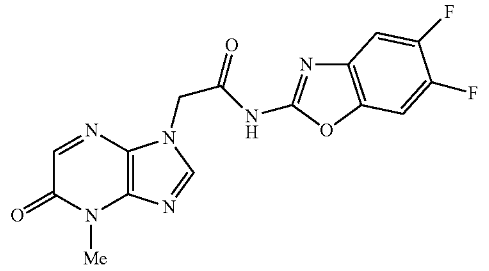 [SMILES: Cn1c(=O)cnc2c1ncn2CC(=O)Nc1nc2cc(F)c(F)cc2o1] | N-(5,6-difluorobenzo[d]oxazol-2-yl)-2-(4-methyl-5-oxo-4,5-dihydro-1H-imidazo[4,5-b]pyridin-1-yl)acetamide |
| 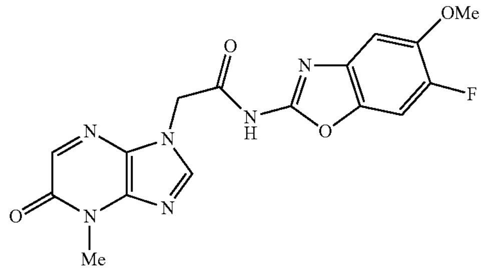 | N-(6-fluoro-5-methoxybenzo[d]oxazol-2-yl)-2-(4-methyl-5-oxo-4,5-dihydro-1H-imidazo[4,5-b]pyridin-1-yl)acetamide |
| 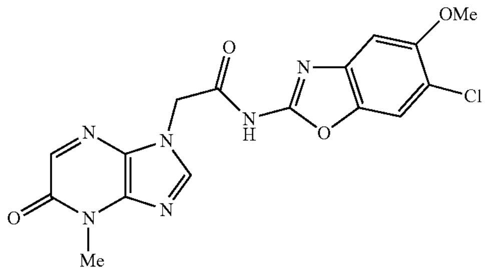 | N-(6-chloro-5-methoxybenzo[d]oxazol-2-yl)-2-(4-methyl-5-oxo-4,5-dihydro-1H-imidazo[4,5-b]pyridin-1-yl)acetamide |

TABLE 2-continued

| | |
|---|---|
| 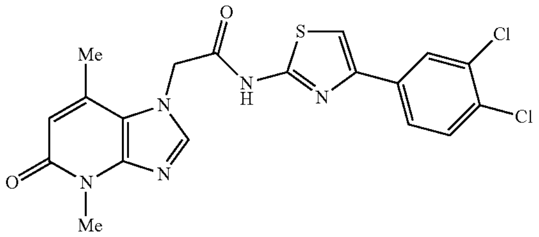 [SMILES: Cc1cc(=O)n(C)c2ncn(CC(=O)Nc3nc(-c4ccc(Cl)c(Cl)c4)cs3)c12] | N-(4-(3,4-dichlorophenyl)thiazol-2-yl)-2-(4,7-dimethyl-5-oxo-4,5-dihydro-1H-imidazo[4,5-b]pyridin-1-yl)acetamide |
| 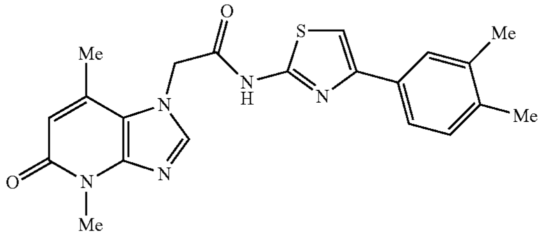 [SMILES: Cc1ccc(-c2csc(NC(=O)Cn3cnc4c3c(C)cc(=O)n4C)n2)cc1C] | 2-(4,7-dimethyl-5-oxo-4,5-dihydro-1H-imidazo[4,5-b]pyridin-1-yl)-N-(4-(3,4-dimethylphenyl)thiazol-2-yl)acetamide |
| 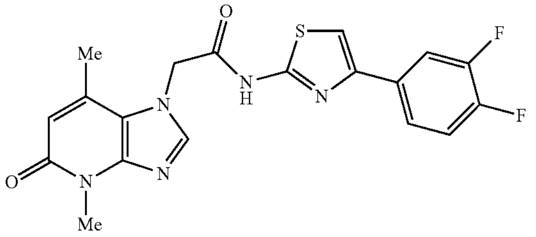 [SMILES: Cc1cc(=O)n(C)c2ncn(CC(=O)Nc3nc(-c4ccc(F)c(F)c4)cs3)c12] | N-(4-(3,4-difluorophenyl)thiazol-2-yl)-2-(4,7-dimethyl-5-oxo-4,5-dihydro-1H-imidazo[4,5-b]pyridin-1-yl)acetamide |
| 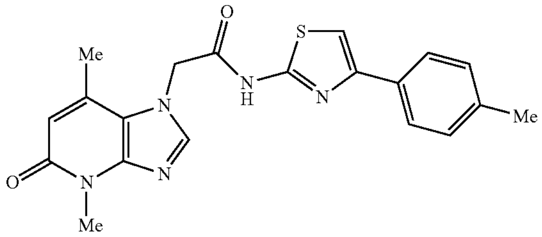 [SMILES: Cc1ccc(-c2csc(NC(=O)Cn3cnc4c3c(C)cc(=O)n4C)n2)cc1] | 2-(4,7-dimethyl-5-oxo-4,5-dihydro-1H-imidazo[4,5-b]pyridin-1-yl)-N-(4-p-tolylthiazol-2-yl)acetamide |
| 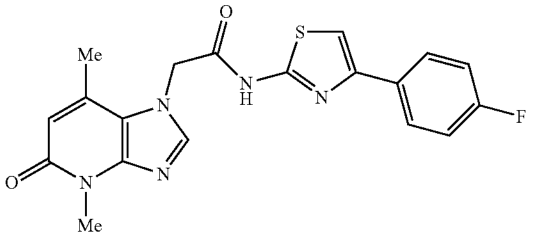 [SMILES: Cc1cc(=O)n(C)c2ncn(CC(=O)Nc3nc(-c4ccc(F)cc4)cs3)c12] | 2-(4,7-dimethyl-5-oxo-4,5-dihydro-1H-imidazo[4,5-b]pyridin-1-yl)-N-(4-(4-fluorophenyl)thiazol-2-yl)acetamide |
| 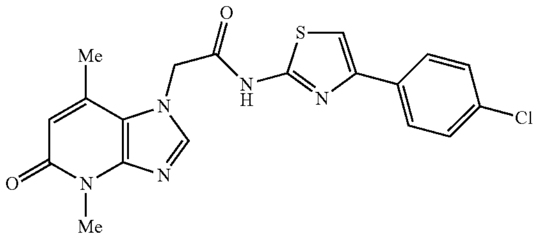 [SMILES: Cc1cc(=O)n(C)c2ncn(CC(=O)Nc3nc(-c4ccc(Cl)cc4)cs3)c12] | N-(4-(4-chlorophenyl)thiazol-2-yl)-2-(4,7-dimethyl-5-oxo-4,5-dihydro-1H-imidazo[4,5-b]pyridin-1-yl)acetamide |

TABLE 2-continued

| | |
|---|---|
| 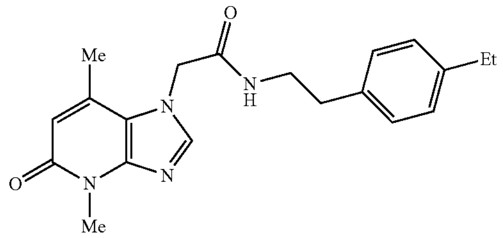 [SMILES: CCc1ccc(CCNC(=O)Cn2cnc3c2c(C)cc(=O)n3C)cc1] | 2-(4,7-dimethyl-5-oxo-4,5-dihydro-1H-imidazo[4,5-b]pyridin-1-yl)-N-(4-ethylphenethyl)acetamide |
| 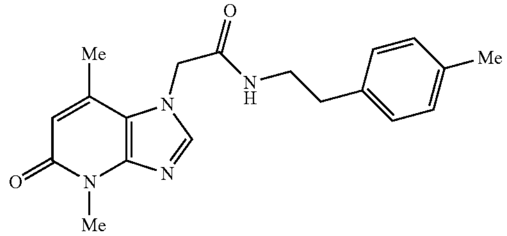 [SMILES: Cc1ccc(CCNC(=O)Cn2cnc3c2c(C)cc(=O)n3C)cc1] | 2-(4,7-dimethyl-5-oxo-4,5-dihydro-1H-imidazo[4,5-b]pyridin-1-yl)-N-(4-methylphenethyl)acetamide |
| 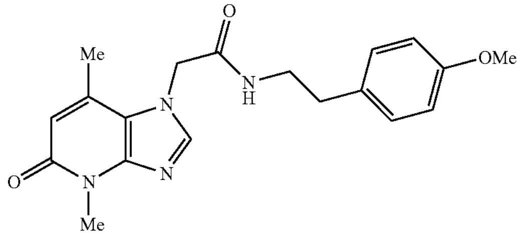 [SMILES: COc1ccc(CCNC(=O)Cn2cnc3c2c(C)cc(=O)n3C)cc1] | 2-(4,7-dimethyl-5-oxo-4,5-dihydro-1H-imidazo[4,5-b]pyridin-1-yl)-N-(4-methoxyphenethyl)acetamide |
| 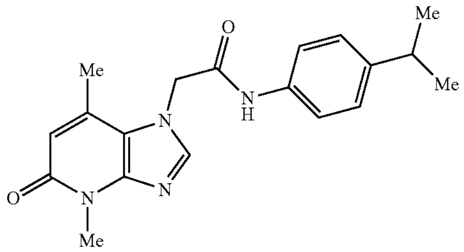 [SMILES: Cc1cc(=O)n(C)c2ncn(CC(=O)Nc3ccc(C(C)C)cc3)c12] | 2-(4,7-dimethyl-5-oxo-4,5-dihydro-1H-imidazo[4,5-b]pyridin-1-yl)-N-(4-isopropylphenyl)acetamide |
| 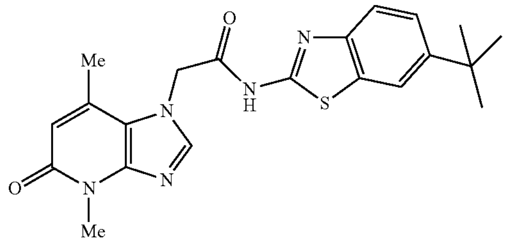 [SMILES: Cc1cc(=O)n(C)c2ncn(CC(=O)Nc3nc4ccc(C(C)(C)C)cc4s3)c12] | N-(6-tert-butylbenzo[d]thiazol-2-yl)-2-(4,7-dimethyl-5-oxo-4,5-dihydro-1H-imidazo[4,5-b]pyridin-1-yl)acetamide |
| 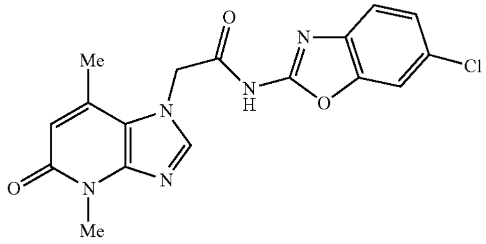 [SMILES: Cc1cc(=O)n(C)c2ncn(CC(=O)Nc3nc4ccc(Cl)cc4o3)c12] | N-(6-chlorobenzo[d]oxazol-2-yl)-2-(4,7-dimethyl-5-oxo-4,5-dihydro-1H-imidazo[4,5-b]pyridin-1-yl)acetamide |

TABLE 2-continued

| | |
|---|---|
| 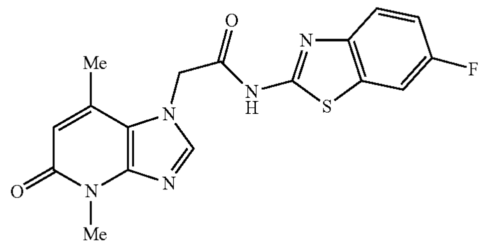 [SMILES: Cc1cc(=O)n(C)c2ncn(CC(=O)Nc3nc4ccc(F)cc4s3)c12] | 2-(4,7-dimethyl-5-oxo-4,5-dihydro-1H-imidazo[4,5-b]pyridin-1-yl)-N-(6-fluorobenzo[d]thiazol-2-yl)acetamide |
| 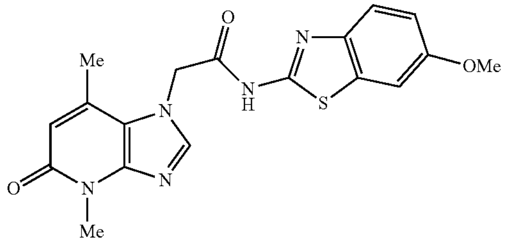 | 2-(4,7-dimethyl-5-oxo-4,5-dihydro-1H-imidazo[4,5-b]pyridin-1-yl)-N-(6-methoxybenzo[d]thiazol-2-yl)acetamide |
| 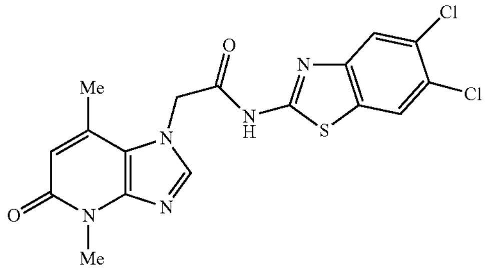 | N-(5,6-dichlorobenzo[d]thiazol-2-yl)-2-(4,7-dimethyl-5-oxo-4,5-dihydro-1H-imidazo[4,5-b]pyridin-1-yl)acetamide |
| 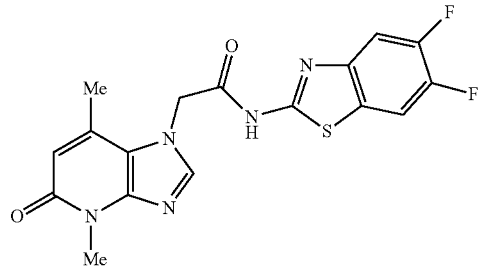 | N-(5,6-difluorobenzo[d]thiazol-2-yl)-2-(4,7-dimethyl-5-oxo-4,5-dihydro-1H-imidazo[4,5-b]pyridin-1-yl)acetamide |
| 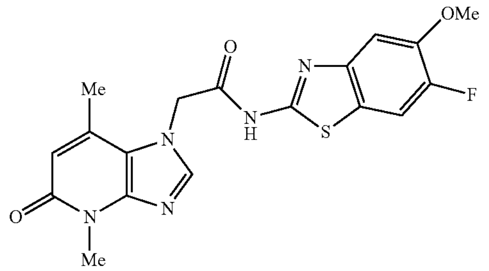 [SMILES: COc1cc2nc(NC(=O)Cn3cnc4c3c(C)cc(=O)n4C)sc2cc1F] | 2-(4,7-dimethyl-5-oxo-4,5-dihydro-1H-imidazo[4,5-b]pyridin-1-yl)-N-(6-fluoro-5-methoxybenzo[d]thiazol-2-yl)acetamide |
| 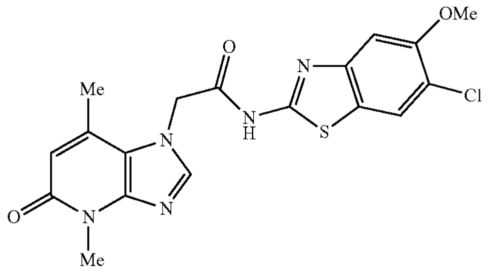 | N-(6-chloro-5-methoxybenzo[d]thiazol-2-yl)-2-(4,7-dimethyl-5-oxo-4,5-dihydro-1H-imidazo[4,5-b]pyridin-1-yl)acetamide |

TABLE 2-continued

| | |
|---|---|
| 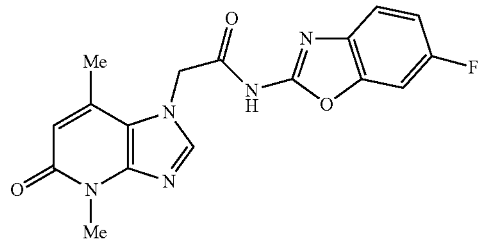 [SMILES: Cc1cc(=O)n(C)c2ncn(CC(=O)Nc3nc4ccc(F)cc4o3)c12] | 2-(4,7-dimethyl-5-oxo-4,5-dihydro-1H-imidazo[4,5-b]pyridin-1-yl)-N-(6-fluorobenzo[d]oxazol-2-yl)acetamide |
| 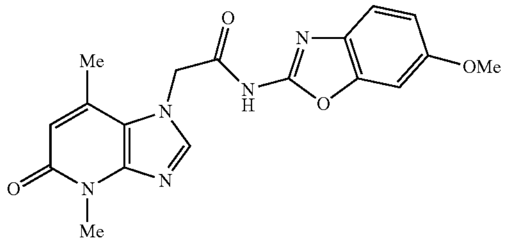 [SMILES: COc1ccc2nc(NC(=O)Cn3cnc4c3c(C)cc(=O)n4C)oc2c1] | 2-(4,7-dimethyl-5-oxo-4,5-dihydro-1H-imidazo[4,5-b]pyridin-1-yl)-N-(6-methoxybenzo[d]oxazol-2-yl)acetamide |
| 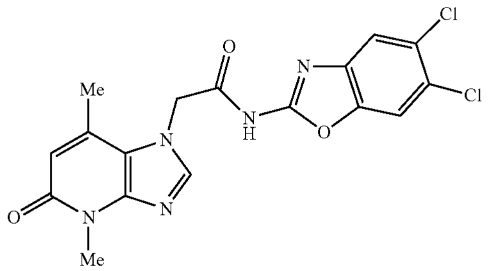 [SMILES: Cc1cc(=O)n(C)c2ncn(CC(=O)Nc3nc4cc(Cl)c(Cl)cc4o3)c12] | N-(5,6-dichlorobenzo[d]oxazol-2-yl)-2-(4,7-dimethyl-5-oxo-4,5-dihydro-1H-imidazo[4,5-b]pyridin-1-yl)acetamide |
| 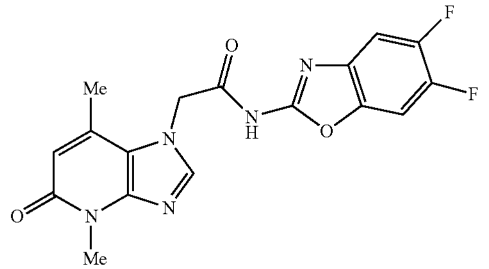 [SMILES: Cc1cc(=O)n(C)c2ncn(CC(=O)Nc3nc4cc(F)c(F)cc4o3)c12] | N-(5,6-difluorobenzo[d]oxazol-2-yl)-2-(4,7-dimethyl-5-oxo-4,5-dihydro-1H-imidazo[4,5-b]pyridin-1-yl)acetamide |
| 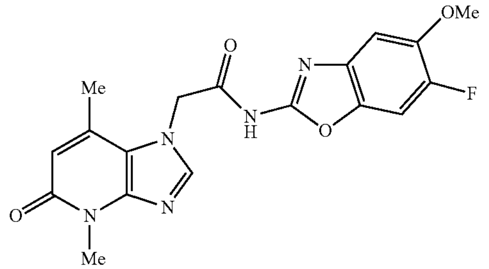 | 2-(4,7-dimethyl-5-oxo-4,5-dihydro-1H-imidazo[4,5-b]pyridin-1-yl)-N-(6-fluoro-5-methoxybenzo[d]oxazol-2-yl)acetamide |
| 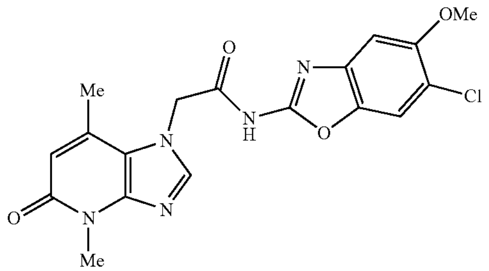 [SMILES: COc1cc2nc(NC(=O)Cn3cnc4c3c(C)cc(=O)n4C)oc2cc1Cl] | N-(6-chloro-5-methoxybenzo[d]oxazol-2-yl)-2-(4,7-dimethyl-5-oxo-4,5-dihydro-1H-imidazo[4,5-b]pyridin-1-yl)acetamide |

TABLE 2-continued

| | |
|---|---|
| 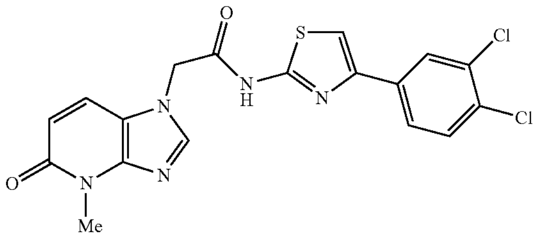 | N-(4-(3,4-dichlorophenyl)thiazol-2-yl)-2-(4-methyl-5-oxo-4,5-dihydro-1H-imidazo[4,5-b]pyridin-1-yl)acetamide |
| 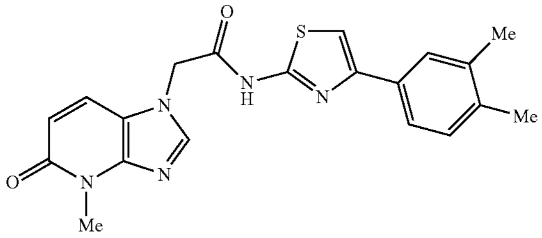 [SMILES: Cc1ccc(-c2csc(NC(=O)Cn3cnc4c3ccc(=O)n4C)n2)cc1C] | N-(4-(3,4-dimethylphenyl)thiazol-2-yl)-2-(4-methyl-5-oxo-4,5-dihydro-1H-imidazo[4,5-b]pyridin-1-yl)acetamide |
| 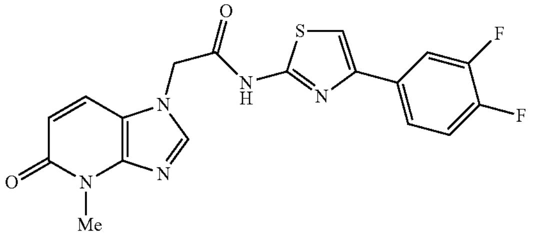 [SMILES: Cn1c(=O)ccc2c1ncn2CC(=O)Nc1nc(-c2ccc(F)c(F)c2)cs1] | N-(4-(3,4-difluorophenyl)thiazol-2-yl)-2-(4-methyl-5-oxo-4,5-dihydro-1H-imidazo[4,5-b]pyridin-1-yl)acetamide |
| 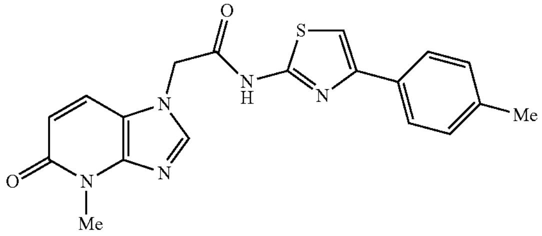 [SMILES: Cc1ccc(-c2csc(NC(=O)Cn3cnc4c3ccc(=O)n4C)n2)cc1] | 2-(4-methyl-5-oxo-4,5-dihydro-1H-imidazo[4,5-b]pyridin-1-yl)-N-(4-p-tolylthiazol-2-yl)acetamide |
| 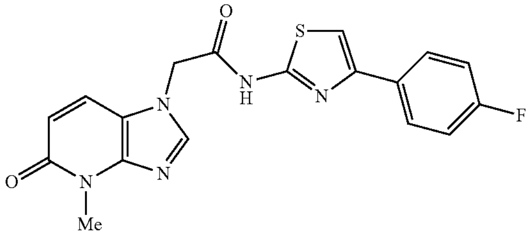 [SMILES: Cn1c(=O)ccc2c1ncn2CC(=O)Nc1nc(-c2ccc(F)cc2)cs1] | N-(4-(4-fluorophenyl)thiazol-2-yl)-2-(4-methyl-5-oxo-4,5-dihydro-1H-imidazo[4,5-b]pyridin-1-yl)acetamide |
| 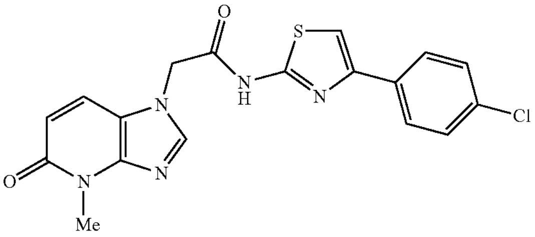 [SMILES: Cn1c(=O)ccc2c1ncn2CC(=O)Nc1nc(-c2ccc(Cl)cc2)cs1] | N-(4-(4-chlorophenyl)thiazol-2-yl)-2-(4-methyl-5-oxo-4,5-dihydro-1H-imidazo[4,5-b]pyridin-1-yl)acetamide |

TABLE 2-continued

| | |
|---|---|
| 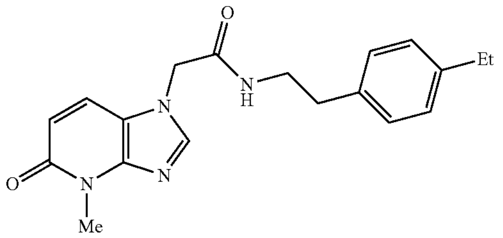 [SMILES: CCc1ccc(CCNC(=O)Cn2cnc3c2ccc(=O)n3C)cc1] | N-(4-ethylphenethyl)-2-(4-methyl-5-oxo-4,5-dihydro-1H-imidazo[4,5-b]pyridin-1-yl)acetamide |
| 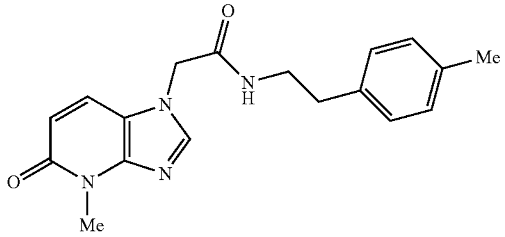 | 2-(4-methyl-5-oxo-4,5-dihydro-1H-imidazo[4,5-b]pyridin-1-yl)-N-(4-methylphenethyl)acetamide |
| 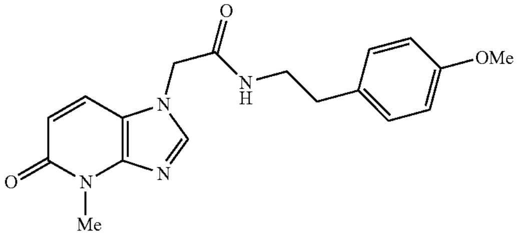 | N-(4-methoxyphenethyl)-2-(4-methyl-5-oxo-4,5-dihydro-1H-imidazo[4,5-b]pyridin-1-yl)acetamide |
| 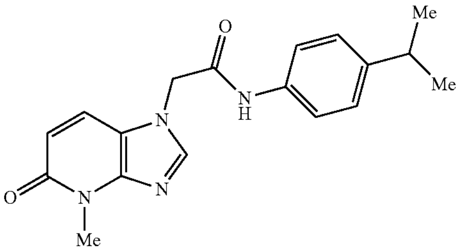 [SMILES: CC(C)c1ccc(NC(=O)Cn2cnc3c2ccc(=O)n3C)cc1] | N-(4-isopropylphenyl)-2-(4-methyl-5-oxo-4,5-dihydro-1H-imidazo[4,5-b]pyridin-1-yl)acetamide |
| 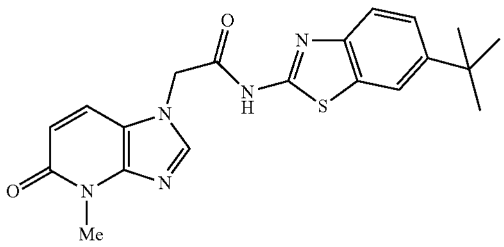 | N-(6-tert-butylbenzo[d]thiazol-2-yl)-2-(4-methyl-5-oxo-4,5-dihydro-1H-imidazo[4,5-b]pyridin-1-yl)acetamide |
| 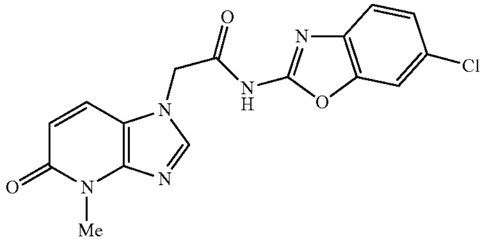 [SMILES: Cn1c(=O)ccc2c1ncn2CC(=O)Nc1nc2ccc(Cl)cc2o1] | N-(6-chlorobenzo[d]oxazol-2-yl)-2-(4-methyl-5-oxo-4,5-dihydro-1H-imidazo[4,5-b]pyridin-1-yl)acetamide |

TABLE 2-continued

| | |
|---|---|
| 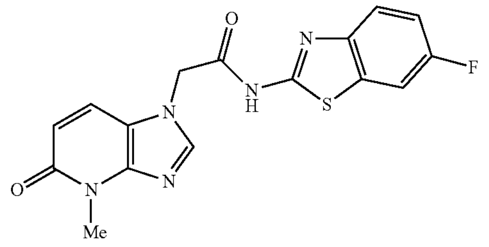 | N-(6-fluorobenzo[d]thiazol-2-yl)-2-(4-methyl-5-oxo-4,5-dihydro-1H-imidazo[4,5-b]pyridin-1-yl)acetamide |
| 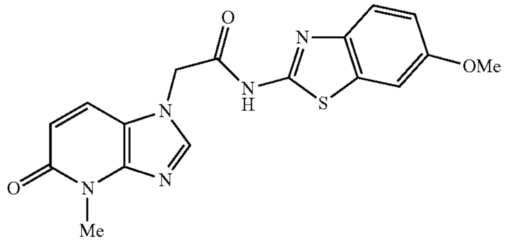 [SMILES: COc1ccc2nc(NC(=O)Cn3cnc4c3ccc(=O)n4C)sc2c1] | N-(6-methoxybenzo[d]thiazol-2-yl)-2-(4-methyl-5-oxo-4,5-dihydro-1H-imidazo[4,5-b]pyridin-1-yl)acetamide |
| 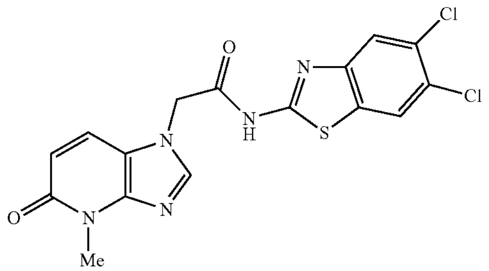 | N-(5,6-dichlorobenzo[d]thiazol-2-yl)-2-(4-methyl-5-oxo-4,5-dihydro-1H-imidazo[4,5-b]pyridin-1-yl)acetamide |
| 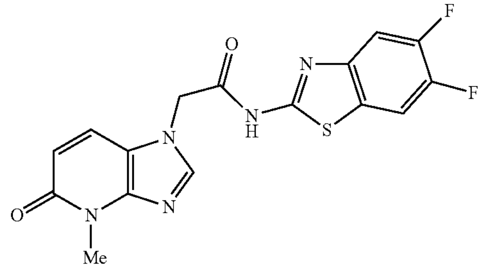 | N-(5,6-difluorobenzo[d]thiazol-2-yl)-2-(4-methyl-5-oxo-4,5-dihydro-1H-imidazo[4,5-b]pyridin-1-yl)acetamide |
| 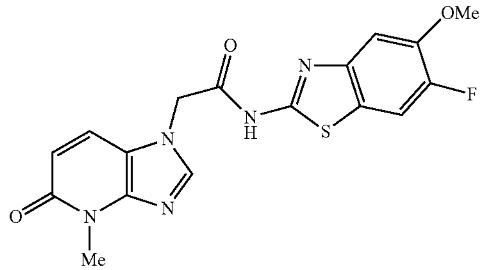 | N-(6-fluoro-5-methoxybenzo[d]thiazol-2-yl)-2-(4-methyl-5-oxo-4,5-dihydro-1H-imidazo[4,5-b]pyridin-1-yl)acetamide |
| 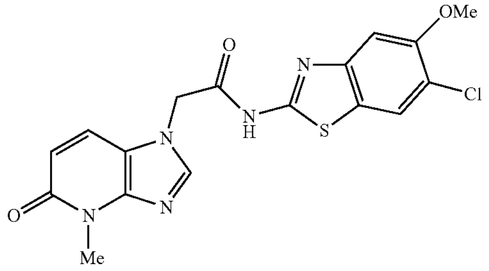 | N-(6-chloro-5-methoxybenzo[d]thiazol-2-yl)-2-(4-methyl-5-oxo-4,5-dihydro-1H-imidazo[4,5-b]pyridin-1-yl)acetamide |

TABLE 2-continued

| | |
|---|---|
| 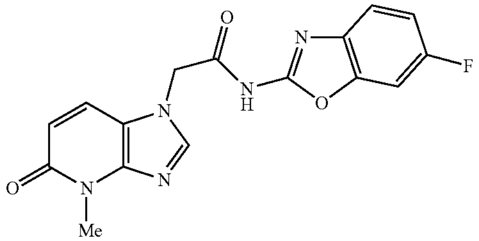 [SMILES: Cn1c(=O)ccc2c1ncn2CC(=O)Nc1nc2ccc(F)cc2o1] | N-(6-fluorobenzo[d]oxazol-2-yl)-2-(4-methyl-5-oxo-4,5-dihydro-1H-imidazo[4,5-b]pyridin-1-yl)acetamide |
| 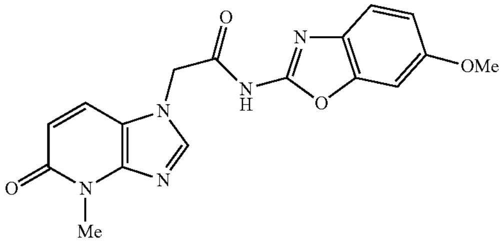 | N-(6-methoxybenzo[d]oxazol-2-yl)-2-(4-methyl-5-oxo-4,5-dihydro-1H-imidazo[4,5-b]pyridin-1-yl)acetamide |
| 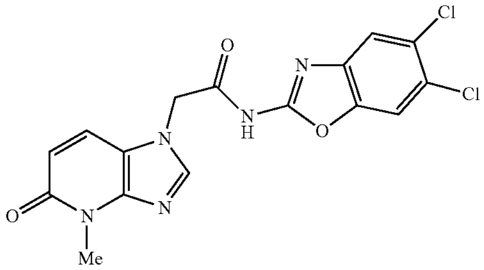 [SMILES: Cn1c(=O)ccc2c1ncn2CC(=O)Nc1nc2cc(Cl)c(Cl)cc2o1] | N-(5,6-dichlorobenzo[d]oxazol-2-yl)-2-(4-methyl-5-oxo-4,5-dihydro-1H-imidazo[4,5-b]pyridin-1-yl)acetamide |
| 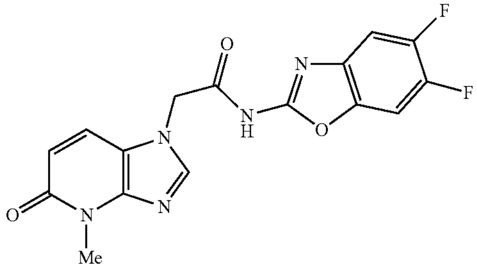 [SMILES: Cn1c(=O)ccc2c1ncn2CC(=O)Nc1nc2cc(F)c(F)cc2o1] | N-(5,6-difluorobenzo[d]oxazol-2-yl)-2-(4-methyl-5-oxo-4,5-dihydro-1H-imidazo[4,5-b]pyridin-1-yl)acetamide |
| 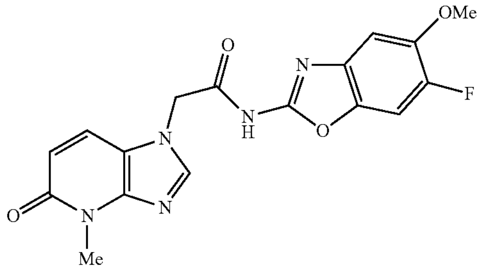 | N-(6-fluoro-5-methoxybenzo[d]oxazol-2-yl)-2-(4-methyl-5-oxo-4,5-dihydro-1H-imidazo[4,5-b]pyridin-1-yl)acetamide |
| 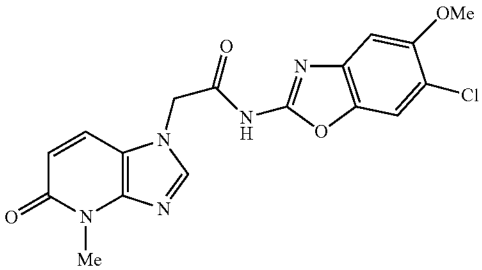 | N-(6-chloro-5-methoxybenzo[d]oxazol-2-yl)-2-(4-methyl-5-oxo-4,5-dihydro-1H-imidazo[4,5-b]pyridin-1-yl)acetamide |

Compounds of Formula IV include those shown in Table 3.

TABLE 3

| | |
|---|---|
| 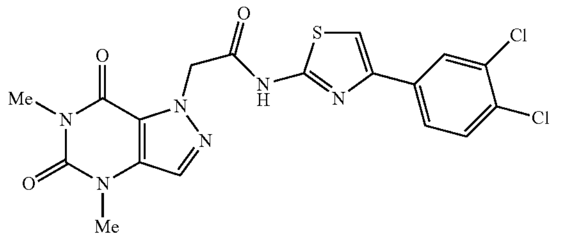 [SMILES: Cn1c(=O)c2c(cnn2CC(=O)Nc2nc(-c3ccc(Cl)c(Cl)c3)cs2)n(C)c1=O] | N-(4-(3,4-dichlorophenyl)thiazol-2-yl)-2-(4,6-dimethyl-5,7-dioxo-4,5,6,7-tetrahydro-1H-pyrazolo[4,3-d]pyrimidin-1-yl)acetamide |
| 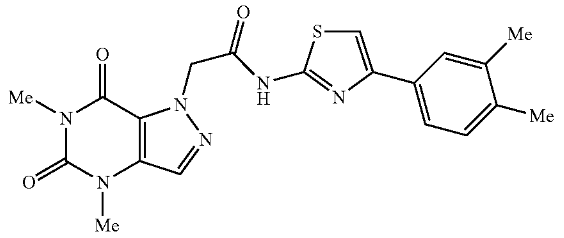 [SMILES: Cc1ccc(-c2csc(NC(=O)Cn3ncc4c3c(=O)n(C)c(=O)n4C)n2)cc1C] | 2-(4,6-dimethyl-5,7-dioxo-4,5,6,7-tetrahydro-1H-pyrazolo[4,3-d]pyrimidin-1-yl)-N-(4-(3,4-dimethylphenyl)thiazol-2-yl)acetamide |
| 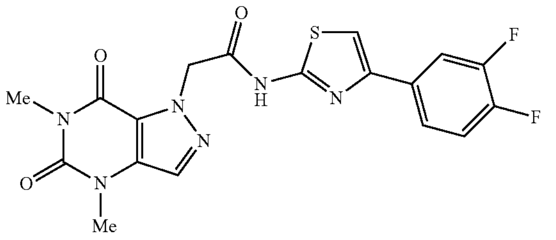 [SMILES: Cn1c(=O)c2c(cnn2CC(=O)Nc2nc(-c3ccc(F)c(F)c3)cs2)n(C)c1=O] | N-(4-(3,4-difluorophenyl)thiazol-2-yl)-2-(4,6-dimethyl-5,7-dioxo-4,5,6,7-tetrahydro-1H-pyrazolo[4,3-d]pyrimidin-1-yl)acetamide |
| 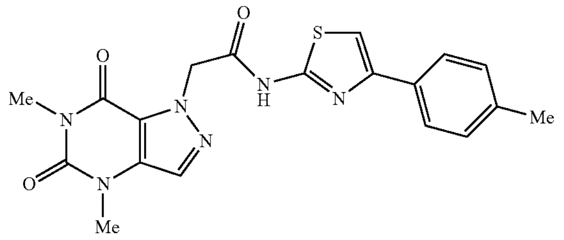 [SMILES: Cc1ccc(-c2csc(NC(=O)Cn3ncc4c3c(=O)n(C)c(=O)n4C)n2)cc1] | 2-(4,6-dimethyl-5,7-dioxo-4,5,6,7-tetrahydro-1H-pyrazolo[4,3-d]pyrimidin-1-yl)-N-(4-p-tolylthiazol-2-yl)acetamide |
| 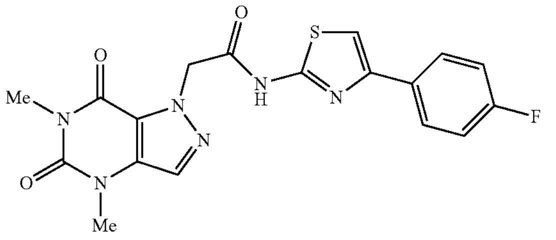 [SMILES: Cn1c(=O)c2c(cnn2CC(=O)Nc2nc(-c3ccc(F)cc3)cs2)n(C)c1=O] | 2-(4,6-dimethyl-5,7-dioxo-4,5,6,7-tetrahydro-1H-pyrazolo[4,3-d]pyrimidin-1-yl)-N-(4-(4-fluorophenyl)thiazol-2-yl)acetamide |
| 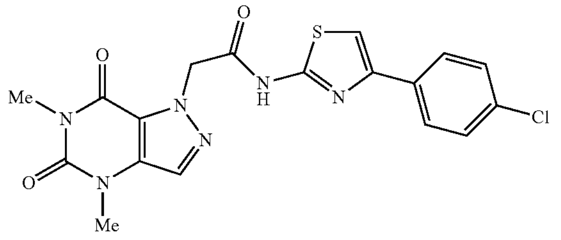 [SMILES: Cn1c(=O)c2c(cnn2CC(=O)Nc2nc(-c3ccc(Cl)cc3)cs2)n(C)c1=O] | N-(4-(4-chlorophenyl)thiazol-2-yl)-2-(4,6-dimethyl-5,7-dioxo-4,5,6,7-tetrahydro-1H-pyrazolo[4,3-d]pyrimidin-1-yl)acetamide |

TABLE 3-continued

| | |
|---|---|
| 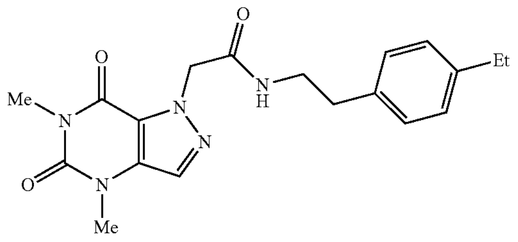 [SMILES: CCc1ccc(CCNC(=O)Cn2ncc3c2c(=O)n(C)c(=O)n3C)cc1] | 2-(4,6-dimethyl-5,7-dioxo-4,5,6,7-tetrahydro-1H-pyrazolo[4,3-d]pyrimidin-1-yl)-N-(4-ethylphenethyl)acetamide |
| 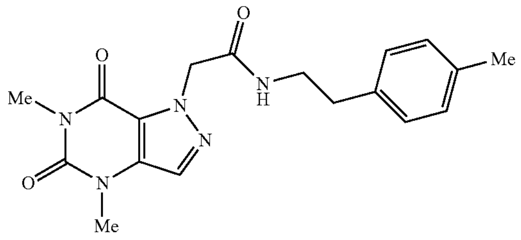 [SMILES: Cc1ccc(CCNC(=O)Cn2ncc3c2c(=O)n(C)c(=O)n3C)cc1] | 2-(4,6-dimethyl-5,7-dioxo-4,5,6,7-tetrahydro-1H-pyrazolo[4,3-d]pyrimidin-1-yl)-N-(4-methylphenethyl)acetamide |
| 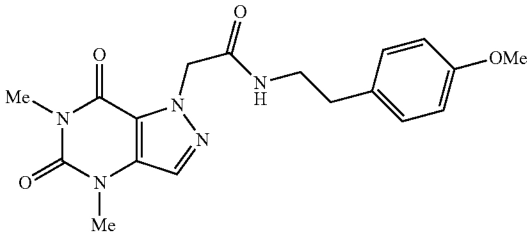 [SMILES: COc1ccc(CCNC(=O)Cn2ncc3c2c(=O)n(C)c(=O)n3C)cc1] | 2-(4,6-dimethyl-5,7-dioxo-4,5,6,7-tetrahydro-1H-pyrazolo[4,3-d]pyrimidin-1-yl)-N-(4-methoxyphenethyl)acetamide |
| 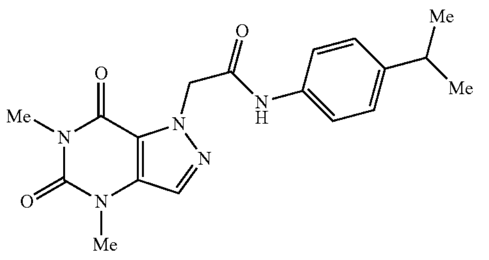 [SMILES: CC(C)c1ccc(NC(=O)Cn2ncc3c2c(=O)n(C)c(=O)n3C)cc1] | 2-(4,6-dimethyl-5,7-dioxo-4,5,6,7-tetrahydro-1H-pyrazolo[4,3-d]pyrimidin-1-yl)-N-(4-isopropylphenyl)acetamide |
| 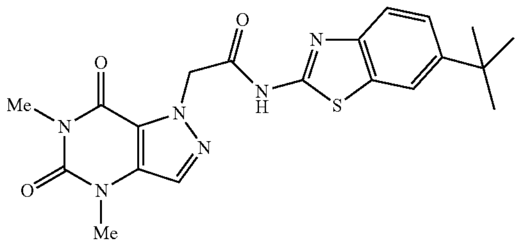 | N-(6-tert-butylbenzo[d]thiazol-2-yl)-2-(4,6-dimethyl-5,7-dioxo-4,5,6,7-tetrahydro-1H-pyrazolo[4,3-d]pyrimidin-1-yl)acetamide |
| 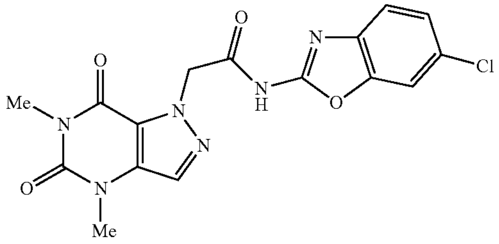 [SMILES: Cn1c(=O)c2c(cnn2CC(=O)Nc2nc3ccc(Cl)cc3o2)n(C)c1=O] | N-(6-chlorobenzo[d]oxazol-2-yl)-2-(4,6-dimethyl-5,7-dioxo-4,5,6,7-tetrahydro-1H-pyrazolo[4,3-d]pyrimidin-1-yl)acetamide |

TABLE 3-continued

| | |
|---|---|
| 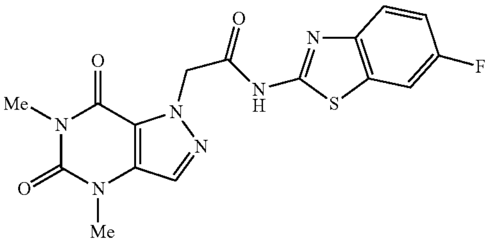 [SMILES: Cn1c(=O)c2c(cnn2CC(=O)Nc2nc3ccc(F)cc3s2)n(C)c1=O] | 2-(4,6-dimethyl-5,7-dioxo-4,5,6,7-tetrahydro-1H-pyrazolo[4,3-d]pyrimidin-1-yl)-N-(6-fluorobenzo[d]thiazol-2-yl)acetamide |
| 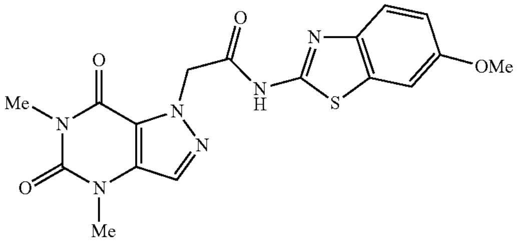 [SMILES: COc1ccc2nc(NC(=O)Cn3ncc4c3c(=O)n(C)c(=O)n4C)sc2c1] | 2-(4,6-dimethyl-5,7-dioxo-4,5,6,7-tetrahydro-1H-pyrazolo[4,3-d]pyrimidin-1-yl)-N-(6-methoxybenzo[d]thiazol-2-yl)acetamide |
| 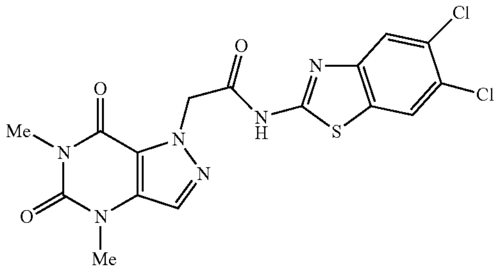 | N-(5,6-dichlorobenzo[d]thiazol-2-yl)-2-(4,6-dimethyl-5,7-dioxo-4,5,6,7-tetrahydro-1H-pyrazolo[4,3-d]pyrimidin-1-yl)acetamide |
| 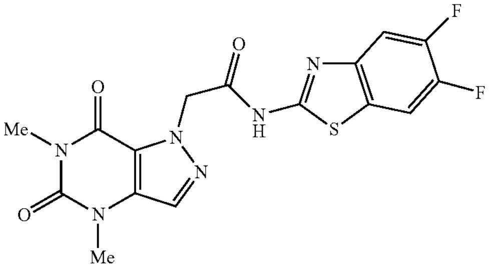 [SMILES: Cn1c(=O)c2c(cnn2CC(=O)Nc2nc3cc(F)c(F)cc3s2)n(C)c1=O] | N-(5,6-difluorobenzo[d]thiazol-2-yl)-2-(4,6-dimethyl-5,7-dioxo-4,5,6,7-tetrahydro-1H-pyrazolo[4,3-d]pyrimidin-1-yl)acetamide |
| 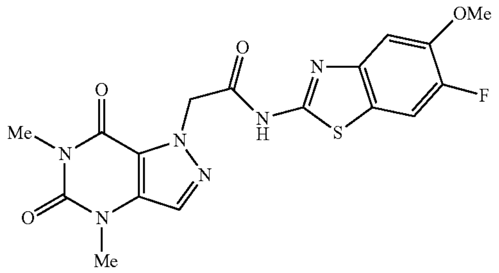 [SMILES: COc1cc2nc(NC(=O)Cn3ncc4c3c(=O)n(C)c(=O)n4C)sc2cc1F] | 2-(4,6-dimethyl-5,7-dioxo-4,5,6,7-tetrahydro-1H-pyrazolo[4,3-d]pyrimidin-1-yl)-N-(6-fluoro-5-methoxybenzo[d]thiazol-2-yl)acetamide |
| 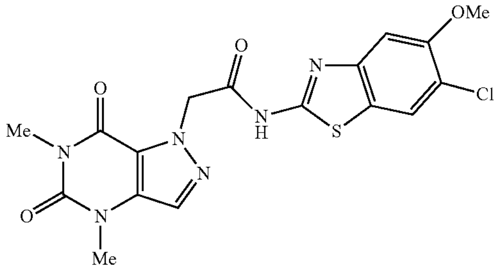 [SMILES: COc1cc2nc(NC(=O)Cn3ncc4c3c(=O)n(C)c(=O)n4C)sc2cc1Cl] | N-(6-chloro-5-methoxybenzo[d]thiazol-2-yl)-2-(4,6-dimethyl-5,7-dioxo-4,5,6,7-tetrahydro-1H-pyrazolo[4,3-d]pyrimidin-1-yl)acetamide |

TABLE 3-continued

| | |
|---|---|
| 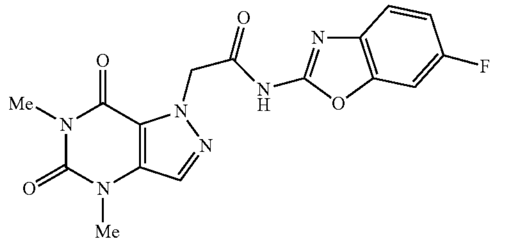 [SMILES: Cn1c(=O)c2c(cnn2CC(=O)Nc2nc3ccc(F)cc3o2)n(C)c1=O] | 2-(4,6-dimethyl-5,7-dioxo-4,5,6,7-tetrahydro-1H-pyrazolo[4,3-d]pyrimidin-1-yl)-N-(6-fluorobenzo[d]oxazol-2-yl)acetamide |
| 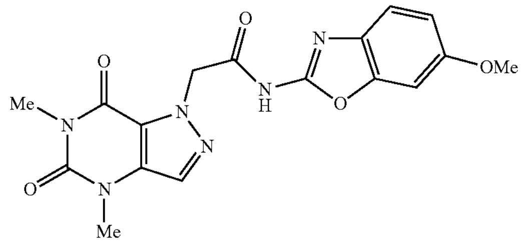 [SMILES: COc1ccc2nc(NC(=O)Cn3ncc4c3c(=O)n(C)c(=O)n4C)oc2c1] | 2-(4,6-dimethyl-5,7-dioxo-4,5,6,7-tetrahydro-1H-pyrazolo[4,3-d]pyrimidin-1-yl)-N-(6-methoxybenzo[d]oxazol-2-yl)acetamide |
| 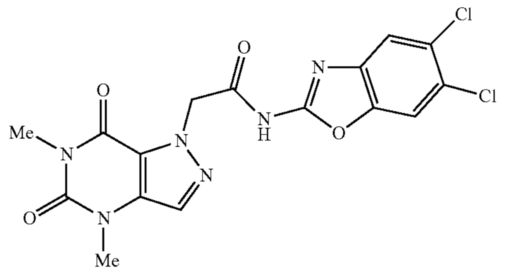 [SMILES: Cn1c(=O)c2c(cnn2CC(=O)Nc2nc3cc(Cl)c(Cl)cc3o2)n(C)c1=O] | N-(5,6-dichlorobenzo[d]oxazol-2-yl)-2-(4,6-dimethyl-5,7-dioxo-4,5,6,7-tetrahydro-1H-pyrazolo[4,3-d]pyrimidin-1-yl)acetamide |
| 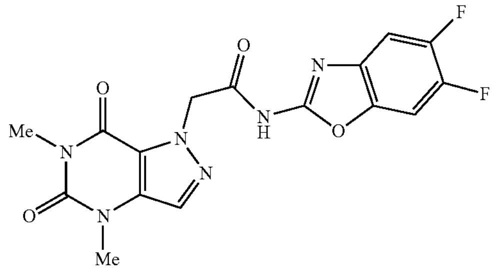 [SMILES: Cn1c(=O)c2c(cnn2CC(=O)Nc2nc3cc(F)c(F)cc3o2)n(C)c1=O] | N-(5,6-difluorobenzo[d]oxazol-2-yl)-2-(4,6-dimethyl-5,7-dioxo-4,5,6,7-tetrahydro-1H-pyrazolo[4,3-d]pyrimidin-1-yl)acetamide |
| 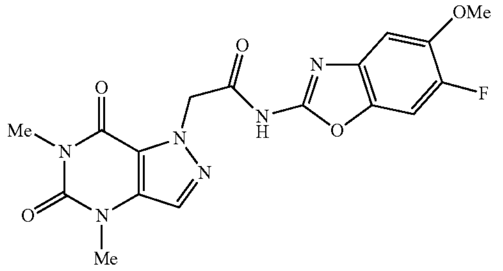 [SMILES: COc1cc2nc(NC(=O)Cn3ncc4c3c(=O)n(C)c(=O)n4C)oc2cc1F] | 2-(4,6-dimethyl-5,7-dioxo-4,5,6,7-tetrahydro-1H-pyrazolo[4,3-d]pyrimidin-1-yl)-N-(6-fluoro-5-methoxybenzo[d]oxazol-2-yl)acetamide |
| 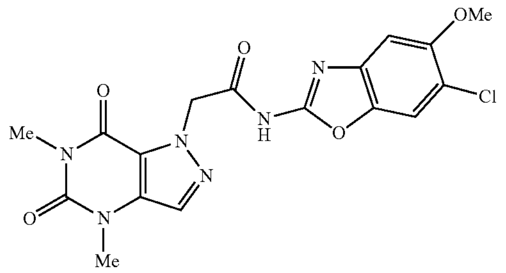 [SMILES: COc1cc2nc(NC(=O)Cn3ncc4c3c(=O)n(C)c(=O)n4C)oc2cc1Cl] | N-(6-chloro-5-methoxybenzo[d]oxazol-2-yl)-2-(4,6-dimethyl-5,7-dioxo-4,5,6,7-tetrahydro-1H-pyrazolo[4,3-d]pyrimidin-1-yl)acetamide |

Compounds of Formula V include those shown in Table 4.

TABLE 4

| | |
|---|---|
| 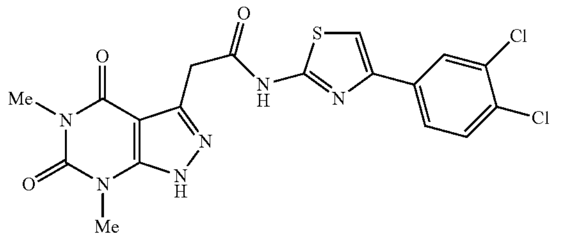 [SMILES: Cn1c(=O)c2c(CC(=O)Nc3nc(-c4ccc(Cl)c(Cl)c4)cs3)n[nH]c2n(C)c1=O] | N-(4-(3,4-dichlorophenyl)thiazol-2-yl)-2-(5,7-dimethyl-4,6-dioxo-4,5,6,7-tetrahydro-1H-pyrazolo[3,4-d]pyrimidin-3-yl)acetamide |
| 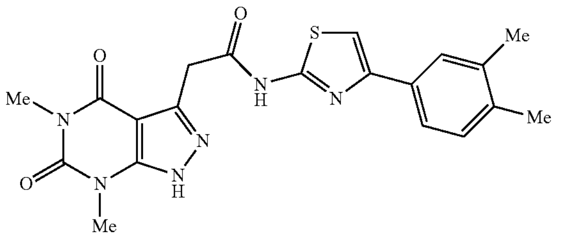 [SMILES: Cc1ccc(-c2csc(NC(=O)Cc3n[nH]c4c3c(=O)n(C)c(=O)n4C)n2)cc1C] | 2-(5,7-dimethyl-4,6-dioxo-4,5,6,7-tetrahydro-1H-pyrazolo[3,4-d]pyrimidin-3-yl)-N-(4-(3,4-dimethylphenyl)thiazol-2-yl)acetamide |
| 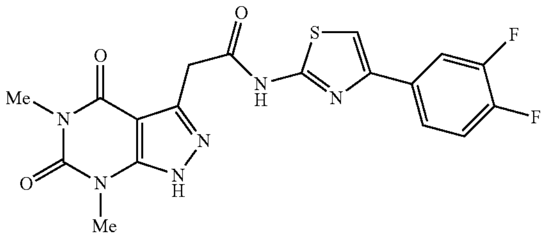 [SMILES: Cn1c(=O)c2c(CC(=O)Nc3nc(-c4ccc(F)c(F)c4)cs3)n[nH]c2n(C)c1=O] | N-(4-(3,4-difluorophenyl)thiazol-2-yl)-2-(5,7-dimethyl-4,6-dioxo-4,5,6,7-tetrahydro-1H-pyrazolo[3,4-d]pyrimidin-3-yl)acetamide |
| 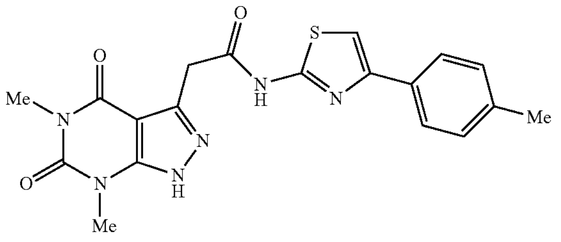 [SMILES: Cc1ccc(-c2csc(NC(=O)Cc3n[nH]c4c3c(=O)n(C)c(=O)n4C)n2)cc1] | 2-(5,7-dimethyl-4,6-dioxo-4,5,6,7-tetrahydro-1H-pyrazolo[3,4-d]pyrimidin-3-yl)-N-(4-p-tolylthiazol-2-yl)acetamide |
| 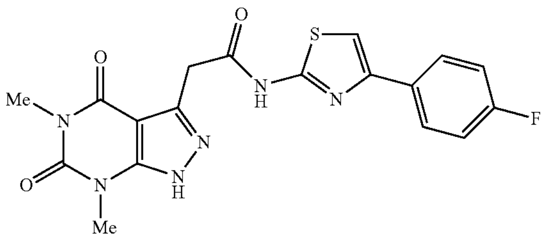 [SMILES: Cn1c(=O)c2c(CC(=O)Nc3nc(-c4ccc(F)cc4)cs3)n[nH]c2n(C)c1=O] | 2-(5,7-dimethyl-4,6-dioxo-4,5,6,7-tetrahydro-1H-pyrazolo[3,4-d]pyrimidin-3-yl)-N-(4-(4-fluorophenyl)thiazol-2-yl)acetamide |
| 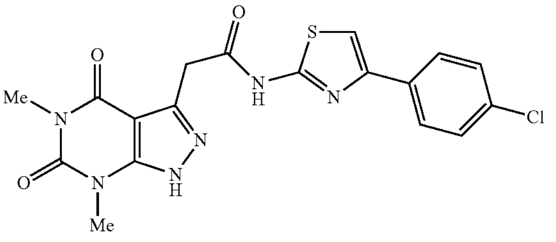 [SMILES: Cn1c(=O)c2c(CC(=O)Nc3nc(-c4ccc(Cl)cc4)cs3)n[nH]c2n(C)c1=O] | N-(4-(4-chlorophenyl)thiazol-2-yl)-2-(5,7-dimethyl-4,6-dioxo-4,5,6,7-tetrahydro-1H-pyrazolo[3,4-d]pyrimidin-3-yl)acetamide |

TABLE 4-continued

| | |
|---|---|
| 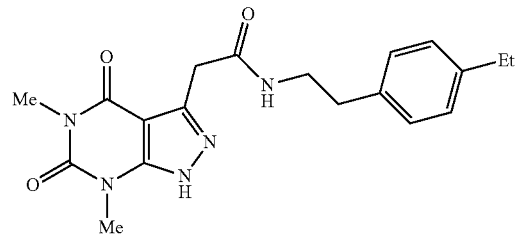 [SMILES: CCc1ccc(CCNC(=O)Cc2n[nH]c3c2c(=O)n(C)c(=O)n3C)cc1] | 2-(5,7-dimethyl-4,6-dioxo-4,5,6,7-tetrahydro-1H-pyrazolo[3,4-d]pyrimidin-3-yl)-N-(4-ethylphenethyl)acetamide |
| 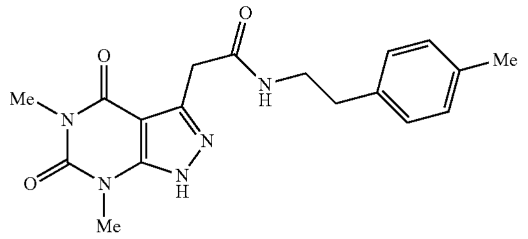 [SMILES: Cc1ccc(CCNC(=O)Cc2n[nH]c3c2c(=O)n(C)c(=O)n3C)cc1] | 2-(5,7-dimethyl-4,6-dioxo-4,5,6,7-tetrahydro-1H-pyrazolo[3,4-d]pyrimidin-3-yl)-N-(4-methylphenethyl)acetamide |
| 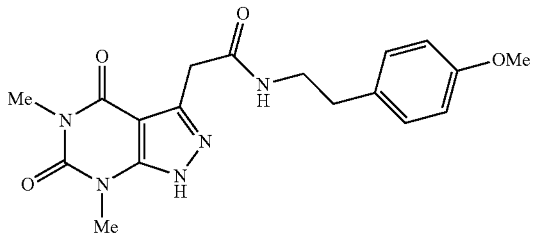 [SMILES: COc1ccc(CCNC(=O)Cc2n[nH]c3c2c(=O)n(C)c(=O)n3C)cc1] | 2-(5,7-dimethyl-4,6-dioxo-4,5,6,7-tetrahydro-1H-pyrazolo[3,4-d]pyrimidin-3-yl)-N-(4-methoxyphenethyl)acetamide |
| 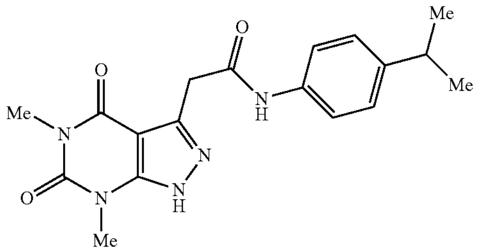 [SMILES: CC(C)c1ccc(NC(=O)Cc2n[nH]c3c2c(=O)n(C)c(=O)n3C)cc1] | 2-(5,7-dimethyl-4,6-dioxo-4,5,6,7-tetrahydro-1H-pyrazolo[3,4-d]pyrimidin-3-yl)-N-(4-isopropylphenyl)acetamide |
| 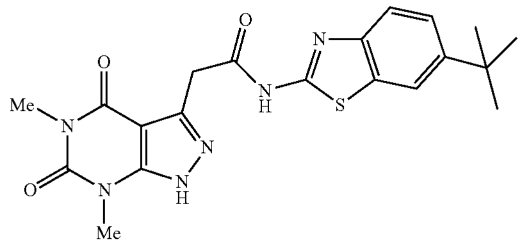 [SMILES: Cn1c(=O)c2c(CC(=O)Nc3nc4ccc(C(C)(C)C)cc4s3)n[nH]c2n(C)c1=O] | N-(6-tert-butylbenzo[d]thiazol-2-yl)-2-(5,7-dimethyl-4,6-dioxo-4,5,6,7-tetrahydro-1H-pyrazolo[3,4-d]pyrimidin-3-yl)acetamide |
| 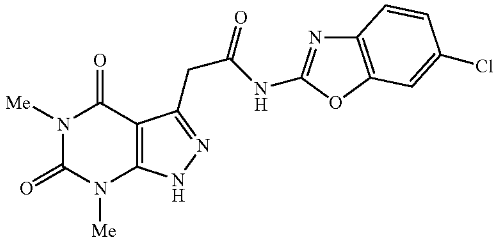 [SMILES: Cn1c(=O)c2c(CC(=O)Nc3nc4ccc(Cl)cc4o3)n[nH]c2n(C)c1=O] | N-(6-chlorobenzo[d]oxazol-2-yl)-2-(5,7-dimethyl-4,6-dioxo-4,5,6,7-tetrahydro-1H-pyrazolo[3,4-d]pyrimidin-3-yl)acetamide |

TABLE 4-continued

| | |
|---|---|
| 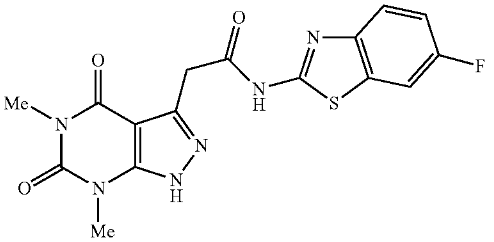 [SMILES: Cn1c(=O)c2c(CC(=O)Nc3nc4ccc(F)cc4s3)n[nH]c2n(C)c1=O] | 2-(5,7-dimethyl-4,6-dioxo-4,5,6,7-tetrahydro-1H-pyrazolo[3,4-d]pyrimidin-3-yl)-N-(6-fluorobenzo[d]thiazol-2-yl)acetamide |
| 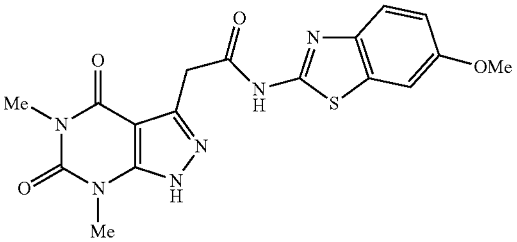 | 2-(5,7-dimethyl-4,6-dioxo-4,5,6,7-tetrahydro-1H-pyrazolo[3,4-d]pyrimidin-3-yl)-N-(6-methoxybenzo[d]thiazol-2-yl)acetamide |
| 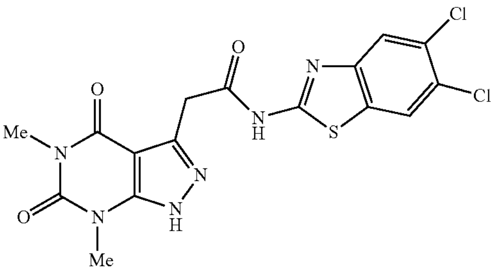 | N-(5,6-dichlorobenzo[d]thiazol-2-yl)-2-(5,7-dimethyl-4,6-dioxo-4,5,6,7-tetrahydro-1H-pyrazolo[3,4-d]pyrimidin-3-yl)acetamide |
| 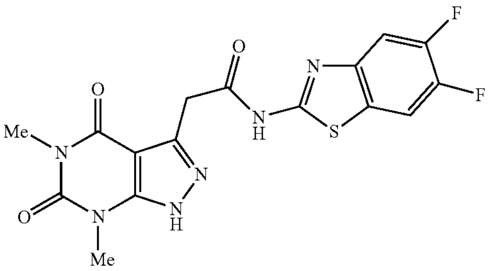 [SMILES: Cn1c(=O)c2c(CC(=O)Nc3nc4cc(F)c(F)cc4s3)n[nH]c2n(C)c1=O] | N-(5,6-difluorobenzo[d]thiazol-2-yl)-2-(5,7-dimethyl-4,6-dioxo-4,5,6,7-tetrahydro-1H-pyrazolo[3,4-d]pyrimidin-3-yl)acetamide |
| 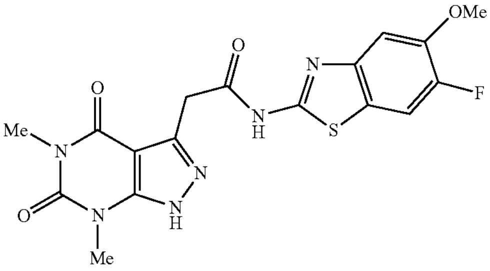 | 2-(5,7-dimethyl-4,6-dioxo-4,5,6,7-tetrahydro-1H-pyrazolo[3,4-d]pyrimidin-3-yl)-N-(6-fluoro-5-methoxybenzo[d]thiazol-2-yl)acetamide |
| 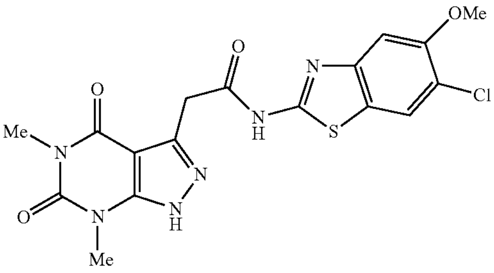 | N-(6-chloro-5-methoxybenzo[d]thiazol-2-yl)-2-(5,7-dimethyl-4,6-dioxo-4,5,6,7-tetrahydro-1H-pyrazolo[3,4-d]pyrimidin-3-yl)acetamide |

TABLE 4-continued

| | |
|---|---|
| 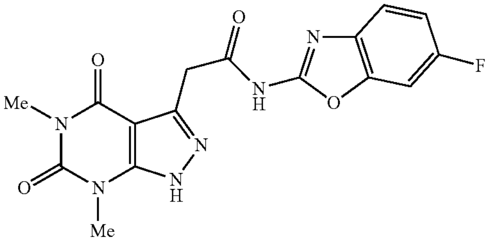 [SMILES: Cn1c(=O)c2c(CC(=O)Nc3nc4ccc(F)cc4o3)n[nH]c2n(C)c1=O] | 2-(5,7-dimethyl-4,6-dioxo-4,5,6,7-tetrahydro-1H-pyrazolo[3,4-d]pyrimidin-3-yl)-N-(6-fluorobenzo[d]oxazol-2-yl)acetamide |
| 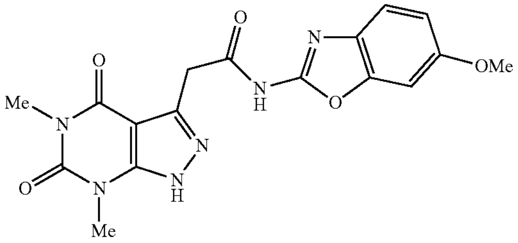 [SMILES: COc1ccc2nc(NC(=O)Cc3n[nH]c4c3c(=O)n(C)c(=O)n4C)oc2c1] | 2-(5,7-dimethyl-4,6-dioxo-4,5,6,7-tetrahydro-1H-pyrazolo[3,4-d]pyrimidin-3-yl)-N-(6-methoxybenzo[d]oxazol-2-yl)acetamide |
| 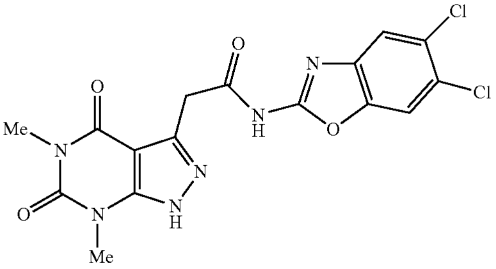 [SMILES: Cn1c(=O)c2c(CC(=O)Nc3nc4cc(Cl)c(Cl)cc4o3)n[nH]c2n(C)c1=O] | N-(5,6-dichlorobenzo[d]oxazol-2-yl)-2-(5,7-dimethyl-4,6-dioxo-4,5,6,7-tetrahydro-1H-pyrazolo[3,4-d]pyrimidin-3-yl)acetamide |
| 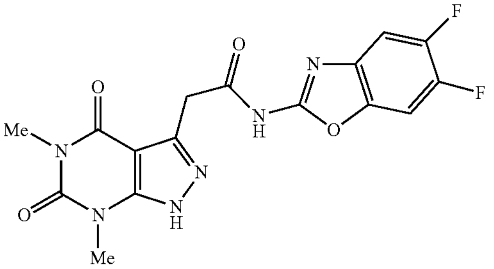 [SMILES: Cn1c(=O)c2c(CC(=O)Nc3nc4cc(F)c(F)cc4o3)n[nH]c2n(C)c1=O] | N-(5,6-difluorobenzo[d]oxazol-2-yl)-2-(5,7-dimethyl-4,6-dioxo-4,5,6,7-tetrahydro-1H-pyrazolo[3,4-d]pyrimidin-3-yl)acetamide |
| 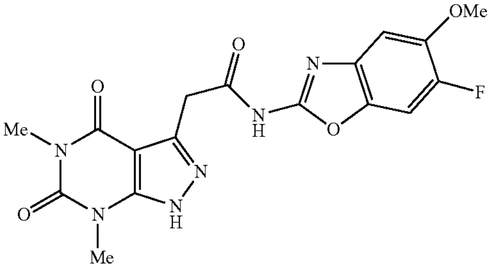 | 2-(5,7-dimethyl-4,6-dioxo-4,5,6,7-tetrahydro-1H-pyrazolo[3,4-d]pyrimidin-3-yl)-N-(6-fluoro-5-methoxybenzo[d]oxazol-2-yl)acetamide |
| 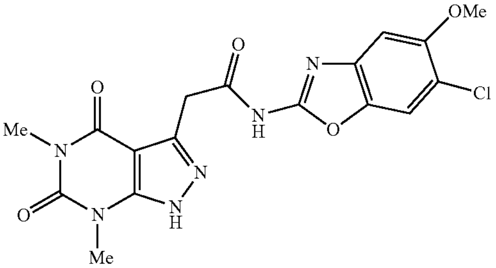 | N-(6-chloro-5-methoxybenzo[d]oxazol-2-yl)-2-(5,7-dimethyl-4,6-dioxo-4,5,6,7-tetrahydro-1H-pyrazolo[3,4-d]pyrimidin-3-yl)acetamide |

Compounds of Formula VI include those shown in Table 5.

TABLE 5

| | |
|---|---|
| 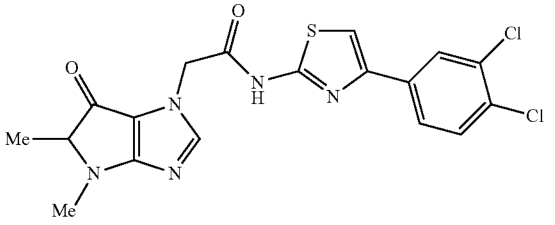 [SMILES: CC1C(=O)c2c(ncn2CC(=O)Nc2nc(-c3ccc(Cl)c(Cl)c3)cs2)N1C] | N-(4-(3,4-dichlorophenyl)thiazol-2-yl)-2-(4,5-dimethyl-6-oxo-5,6-dihydropyrrolo[3,2-d]imidazol-1(4H)-yl)acetamide |
| 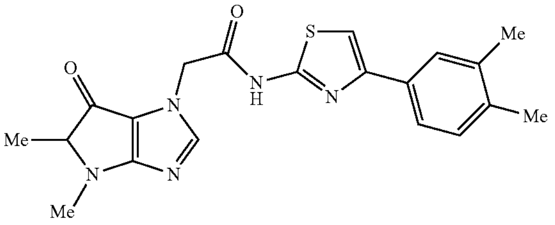 [SMILES: Cc1ccc(-c2csc(NC(=O)Cn3cnc4c3C(=O)C(C)N4C)n2)cc1C] | 2-(4,5-dimethyl-6-oxo-5,6-dihydropyrrolo[3,2-d]imidazol-1(4H)-yl)-N-(4-(3,4-dimethylphenyl)thiazol-2-yl)acetamide |
| 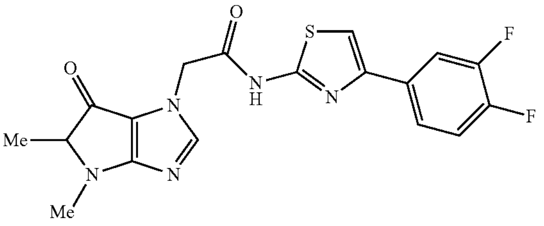 [SMILES: CC1C(=O)c2c(ncn2CC(=O)Nc2nc(-c3ccc(F)c(F)c3)cs2)N1C] | N-(4-(3,4-difluorophenyl)thiazol-2-yl)-2-(4,5-dimethyl-6-oxo-5,6-dihydropyrrolo[3,2-d]imidazol-1(4H)-yl)acetamide |
| 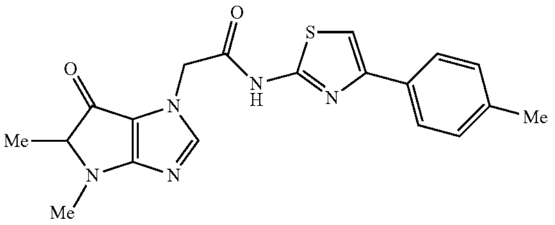 [SMILES: Cc1ccc(-c2csc(NC(=O)Cn3cnc4c3C(=O)C(C)N4C)n2)cc1] | 2-(4,5-dimethyl-6-oxo-5,6-dihydropyrrolo[3,2-d]imidazol-1(4H)-yl)-N-(4-p-tolylthiazol-2-yl)acetamide |
| 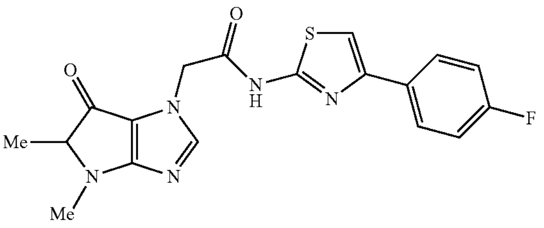 [SMILES: CC1C(=O)c2c(ncn2CC(=O)Nc2nc(-c3ccc(F)cc3)cs2)N1C] | 2-(4,5-dimethyl-6-oxo-5,6-dihydropyrrolo[3,2-d]imidazol-1(4H)-yl)-N-(4-(4-fluorophenyl)thiazol-2-yl)acetamide |
| 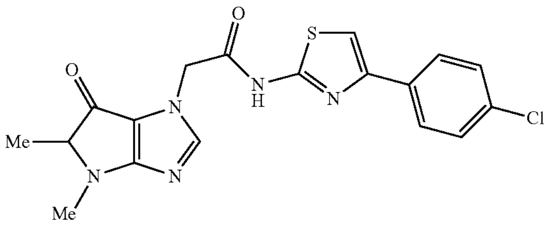 [SMILES: CC1C(=O)c2c(ncn2CC(=O)Nc2nc(-c3ccc(Cl)cc3)cs2)N1C] | N-(4-(4-chlorophenyl)thiazol-2-yl)-2-(4,5-dimethyl-6-oxo-5,6-dihydropyrrolo[3,2-d]imidazol-1(4H)-yl)acetamide |

TABLE 5-continued

| | |
|---|---|
| 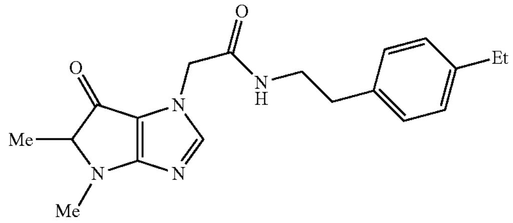 [SMILES: CCc1ccc(CCNC(=O)Cn2cnc3c2C(=O)C(C)N3C)cc1] | 2-(4,5-dimethyl-6-oxo-5,6-dihydropyrrolo[3,2-d]imidazol-1(4H)-yl)-N-(4-ethylphenethyl)acetamide |
| 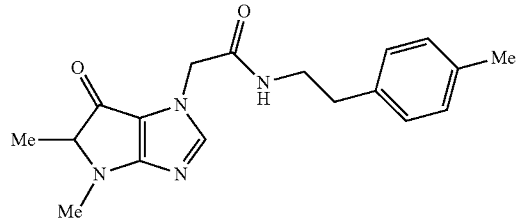 [SMILES: Cc1ccc(CCNC(=O)Cn2cnc3c2C(=O)C(C)N3C)cc1] | 2-(4,5-dimethyl-6-oxo-5,6-dihydropyrrolo[3,2-d]imidazol-1(4H)-yl)-N-(4-methylphenethyl)acetamide |
| 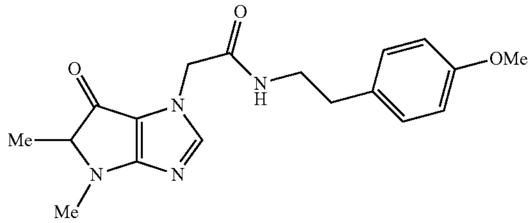 [SMILES: COc1ccc(CCNC(=O)Cn2cnc3c2C(=O)C(C)N3C)cc1] | 2-(4,5-dimethyl-6-oxo-5,6-dihydropyrrolo[3,2-d]imidazol-1(4H)-yl)-N-(4-methoxyphenethyl)acetamide |
| 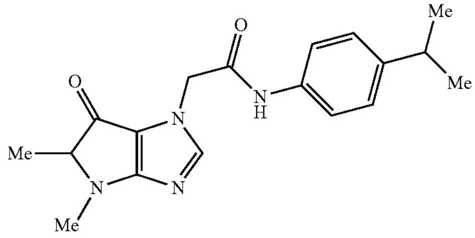 [SMILES: CC(C)c1ccc(NC(=O)Cn2cnc3c2C(=O)C(C)N3C)cc1] | 2-(4,5-dimethyl-6-oxo-5,6-dihydropyrrolo[3,2-d]imidazol-1(4H)-yl)-N-(4-isopropylphenyl)acetamide |
| 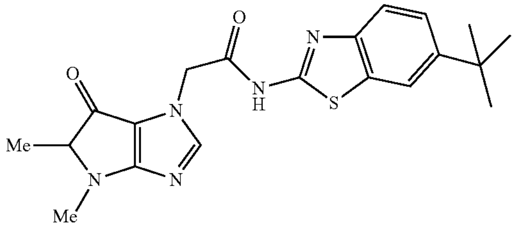 [SMILES: CC1C(=O)c2c(ncn2CC(=O)Nc2nc3ccc(C(C)(C)C)cc3s2)N1C] | N-(6-tert-butylbenzo[d]thiazol-2-yl)-2-(4,5-dimethyl-6-oxo-5,6-dihydropyrrolo[3,2-d]imidazol-1(4H)-yl)acetamide |
| 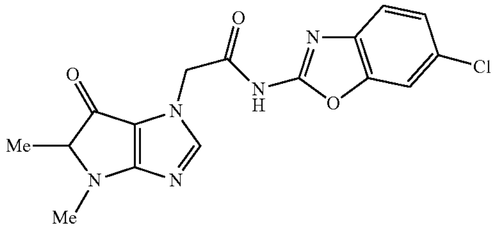 [SMILES: CC1C(=O)c2c(ncn2CC(=O)Nc2nc3ccc(Cl)cc3o2)N1C] | N-(6-chlorobenzo[d]oxazol-2-yl)-2-(4,5-dimethyl-6-oxo-5,6-dihydropyrrolo[3,2-d]imidazol-1(4H)-yl)acetamide |
| 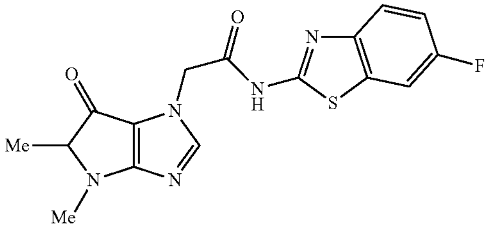 [SMILES: CC1C(=O)c2c(ncn2CC(=O)Nc2nc3ccc(F)cc3s2)N1C] | 2-(4,5-dimethyl-6-oxo-5,6-dihydropyrrolo[3,2-d]imidazol-1(4H)-yl)-N-(6-fluorobenzo[d]thiazol-2-yl)acetamide |

TABLE 5-continued

| | |
|---|---|
| 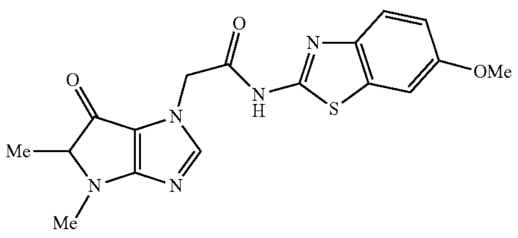 [SMILES: COc1ccc2nc(NC(=O)Cn3cnc4c3C(=O)C(C)N4C)sc2c1] | 2-(4,5-dimethyl-6-oxo-5,6-dihydropyrrolo[3,2-d]imidazol-1(4H)-yl)-N-(6-methoxybenzo[d]thiazol-2-yl)acetamide |
| 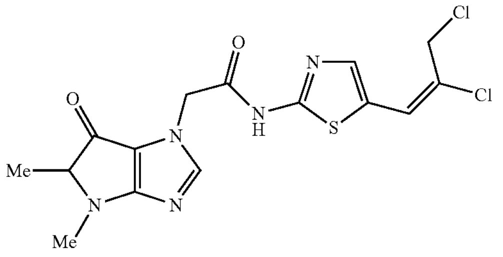 [SMILES: CC1C(=O)c2c(ncn2CC(=O)Nc2ncc(/C=C(/Cl)CCl)s2)N1C] | (E)-N-(5-(2,3-dichloroprop-1-enyl)thiazol-2-yl)-2-(4,5-dimethyl-6-oxo-5,6-dihydropyrrolo[3,2-d]imidazol-1(4H)-yl)acetamide |
| 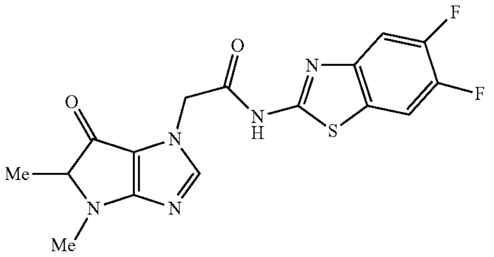 [SMILES: CC1C(=O)c2c(ncn2CC(=O)Nc2nc3cc(F)c(F)cc3s2)N1C] | N-(5,6-difluorobenzo[d]thiazol-2-yl)-2-(4,5-dimethyl-6-oxo-5,6-dihydropyrrolo[3,2-d]imidazol-1(4H)-yl)acetamide |
| 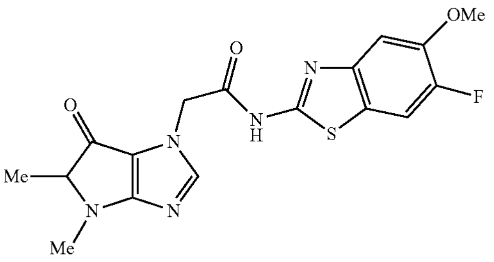 [SMILES: COc1cc2nc(NC(=O)Cn3cnc4c3C(=O)C(C)N4C)sc2cc1F] | 2-(4,5-dimethyl-6-oxo-5,6-dihydropyrrolo[3,2-d]imidazol-1(4H)-yl)-N-(6-fluoro-5-methoxybenzo[d]thiazol-2-yl)acetamide |
| 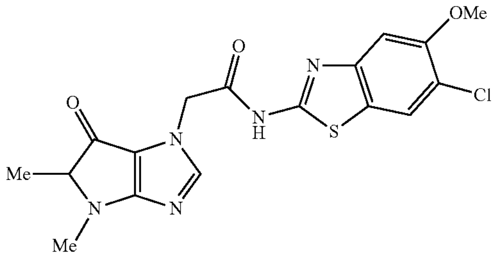 [SMILES: COc1cc2nc(NC(=O)Cn3cnc4c3C(=O)C(C)N4C)sc2cc1Cl] | N-(6-chloro-5-methoxybenzo[d]thiazol-2-yl)-2-(4,5-dimethyl-6-oxo-5,6-dihydropyrrolo[3,2-d]imidazol-1(4H)-yl)acetamide |
| 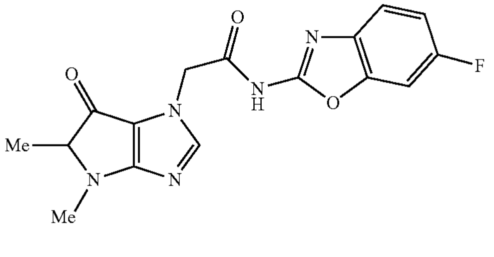 | 2-(4,5-dimethyl-6-oxo-5,6-dihydropyrrolo[3,2-d]imidazol-1(4H)-yl)-N-(6-fluorobenzo[d]oxazol-2-yl)acetamide |

TABLE 5-continued

| | |
|---|---|
| 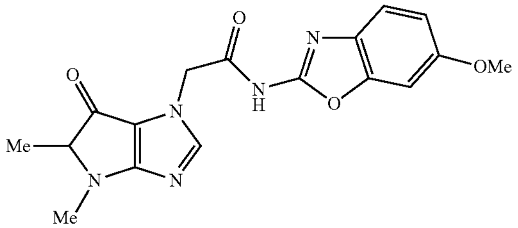 | 2-(4,5-dimethyl-6-oxo-5,6-dihydropyrrolo[3,2-d]imidazol-1(4H)-yl)-N-(6-methoxybenzo[d]oxazol-2-yl)acetamide |
| 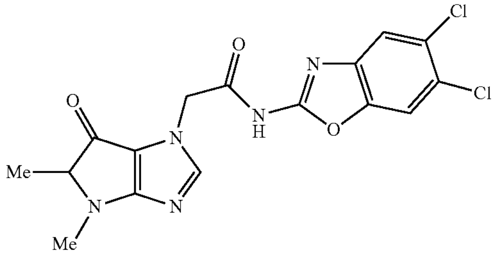 [SMILES: CC1C(=O)c2c(ncn2CC(=O)Nc2nc3cc(Cl)c(Cl)cc3o2)N1C] | N-(5,6-dichlorobenzo[d]oxazol-2-yl)-2-(4,5-dimethyl-6-oxo-5,6-dihydropyrrolo[3,2-d]imidazol-1(4H)-yl)acetamide |
| 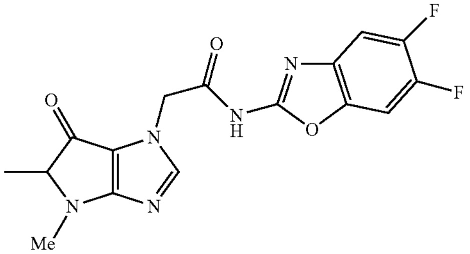 [SMILES: CC1C(=O)c2c(ncn2CC(=O)Nc2nc3cc(F)c(F)cc3o2)N1C] | N-(5,6-difluorobenzo[d]oxazol-2-yl)-2-(4,5-dimethyl-6-oxo-5,6-dihydropyrrolo[3,2-d]imidazol-1(4H)-yl)acetamide |
| 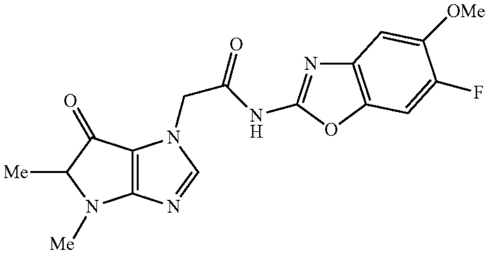 | 2-(4,5-dimethyl-6-oxo-5,6-dihydropyrrolo[3,2-d]imidazol-1(4H)-yl)-N-(6-fluoro-5-methoxybenzo[d]oxazol-2-yl)acetamide |
| 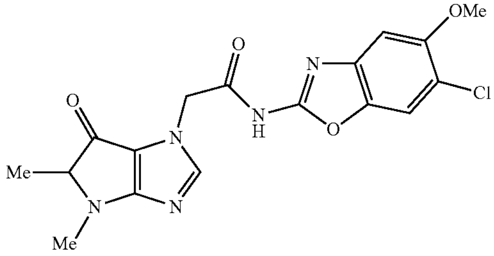 [SMILES: COc1cc2nc(NC(=O)Cn3cnc4c3C(=O)C(C)N4C)oc2cc1Cl] | N-(6-chloro-5-methoxybenzo[d]oxazol-2-yl)-2-(4,5-dimethyl-6-oxo-5,6-dihydropyrrolo[3,2-d]imidazol-1(4H)-yl)acetamide |

Compounds of Formula VII include those shown in Table 6.

TABLE 6

| | |
|---|---|
| 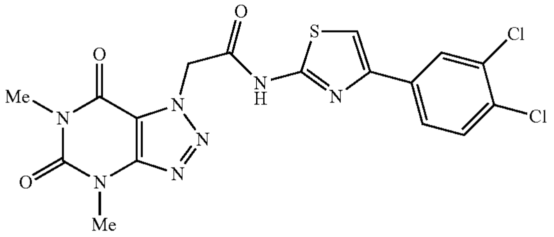 [SMILES: Cn1c(=O)c2c(nnn2CC(=O)Nc2nc(-c3ccc(Cl)c(Cl)c3)cs2)n(C)c1=O] | N-(4-(3,4-dichlorophenyl)thiazol-2-yl)-2-(4,6-dimethyl-5,7-dioxo-4,5,6,7-tetrahydro-1H-[1,2,3]triazolo[4,5-d]pyrimidin-1-yl)acetamide |

TABLE 6-continued

| | |
|---|---|
| 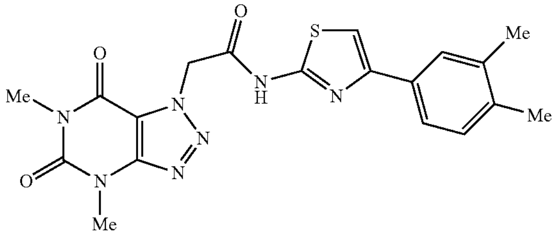 [SMILES: Cc1ccc(-c2csc(NC(=O)Cn3nnc4c3c(=O)n(C)c(=O)n4C)n2)cc1C] | 2-(4,6-dimethyl-5,7-dioxo-4,5,6,7-tetrahydro-1H-[1,2,3]triazolo[4,5-d]pyrimidin-1-yl)-N-(4-(3,4-dimethylphenyl)thiazol-2-yl)acetamide |
| 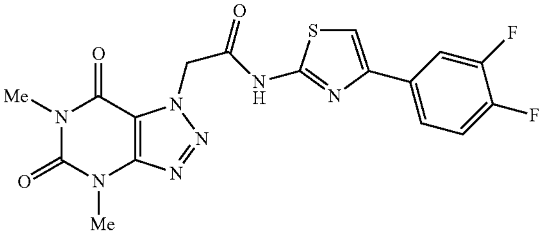 [SMILES: Cn1c(=O)c2c(nnn2CC(=O)Nc2nc(-c3ccc(F)c(F)c3)cs2)n(C)c1=O] | N-(4-(3,4-difluorophenyl)thiazol-2-yl)-2-(4,6-dimethyl-5,7-dioxo-4,5,6,7-tetrahydro-1H-[1,2,3]triazolo[4,5-d]pyrimidin-1-yl)acetamide |
| 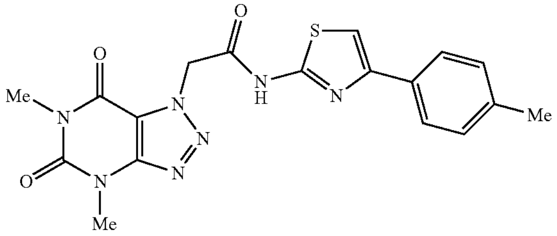 [SMILES: Cc1ccc(-c2csc(NC(=O)Cn3nnc4c3c(=O)n(C)c(=O)n4C)n2)cc1] | 2-(4,6-dimethyl-5,7-dioxo-4,5,6,7-tetrahydro-1H-[1,2,3]triazolo[4,5-d]pyrimidin-1-yl)-N-(4-p-tolylthiazol-2-yl)acetamide |
| 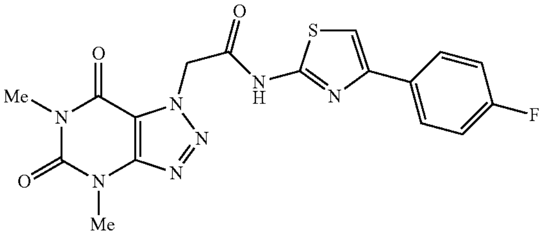 [SMILES: Cn1c(=O)c2c(nnn2CC(=O)Nc2nc(-c3ccc(F)cc3)cs2)n(C)c1=O] | 2-(4,6-dimethyl-5,7-dioxo-4,5,6,7-tetrahydro-1H-[1,2,3]triazolo[4,5-d]pyrimidin-1-yl)-N-(4-(4-fluorophenyl)thiazol-2-yl)acetamide |
| 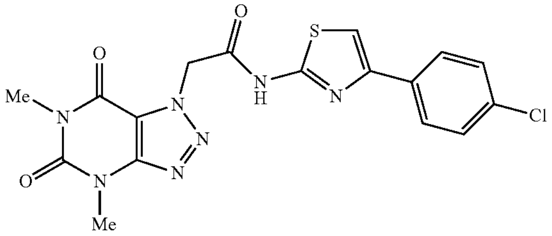 [SMILES: Cn1c(=O)c2c(nnn2CC(=O)Nc2nc(-c3ccc(Cl)cc3)cs2)n(C)c1=O] | N-(4-(4-chlorophenyl)thiazol-2-yl)-2-(4,6-dimethyl-5,7-dioxo-4,5,6,7-tetrahydro-1H-[1,2,3]triazolo[4,5-d]pyrimidin-1-yl)acetamide |
| 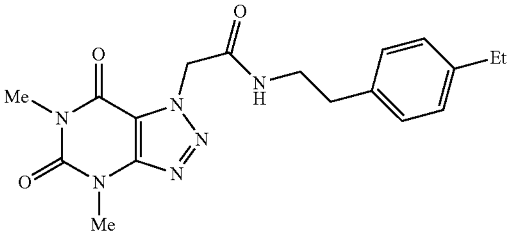 [SMILES: CCc1ccc(CCNC(=O)Cn2nnc3c2c(=O)n(C)c(=O)n3C)cc1] | 2-(4,6-dimethyl-5,7-dioxo-4,5,6,7-tetrahydro-1H-[1,2,3]triazolo[4,5-d]pyrimidin-1-yl)-N-(4-ethylphenethyl)acetamide |

TABLE 6-continued

| | |
|---|---|
| 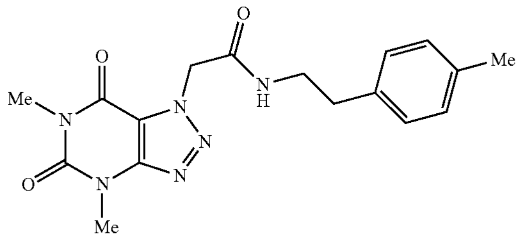 [SMILES: Cc1ccc(CCNC(=O)Cn2nnc3c2c(=O)n(C)c(=O)n3C)cc1] | 2-(4,6-dimethyl-5,7-dioxo-4,5,6,7-tetrahydro-1H-[1,2,3]triazolo[4,5-d]pyrimidin-1-yl)-N-(4-methylphenethyl)acetamide |
| 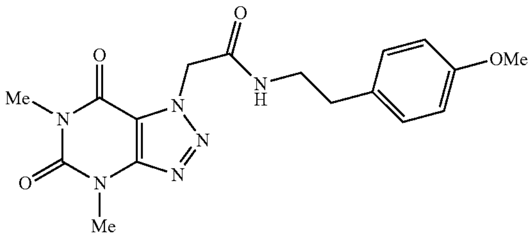 | 2-(4,6-dimethyl-5,7-dioxo-4,5,6,7-tetrahydro-1H-[1,2,3]triazolo[4,5-d]pyrimidin-1-yl)-N-(4-methoxyphenethyl)acetamide |
| 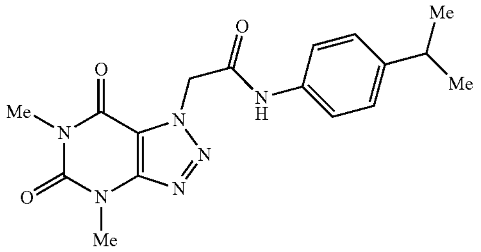 [SMILES: CC(C)c1ccc(NC(=O)Cn2nnc3c2c(=O)n(C)c(=O)n3C)cc1] | 2-(4,6-dimethyl-5,7-dioxo-4,5,6,7-tetrahydro-1H-[1,2,3]triazolo[4,5-d]pyrimidin-1-yl)-N-(4-isopropylphenyl)acetamide |
| 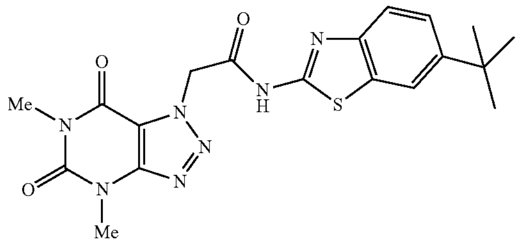 [SMILES: Cn1c(=O)c2c(nnn2CC(=O)Nc2nc3ccc(C(C)(C)C)cc3s2)n(C)c1=O] | N-(6-tert-butylbenzo[d]thiazol-2-yl)-2-(4,6-dimethyl-5,7-dioxo-4,5,6,7-tetrahydro-1H-[1,2,3]triazolo[4,5-d]pyrimidin-1-yl)acetamide |
| 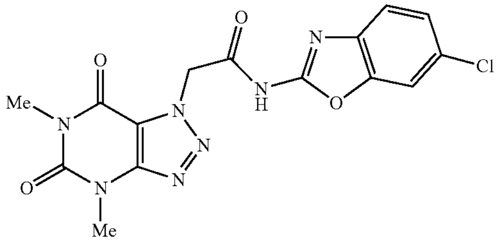 [SMILES: Cn1c(=O)c2c(nnn2CC(=O)Nc2nc3ccc(Cl)cc3o2)n(C)c1=O] | N-(6-chlorobenzo[d]oxazol-2-yl)-2-(4,6-dimethyl-5,7-dioxo-4,5,6,7-tetrahydro-1H-[1,2,3]triazolo[4,5-d]pyrimidin-1-yl)acetamide |
| 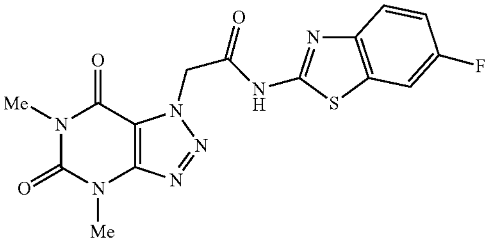 [SMILES: Cn1c(=O)c2c(nnn2CC(=O)Nc2nc3ccc(F)cc3s2)n(C)c1=O] | 2-(4,6-dimethyl-5,7-dioxo-4,5,6,7-tetrahydro-1H-[1,2,3]triazolo[4,5-d]pyrimidin-1-yl)-N-(6-fluorobenzo[d]thiazol-2-yl)acetamide |

TABLE 6-continued

| | |
|---|---|
| 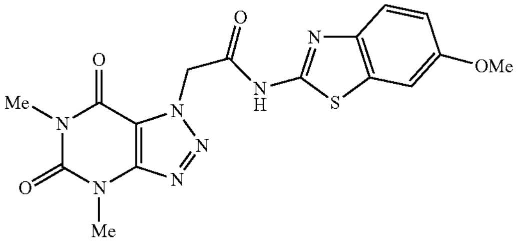 [SMILES: COc1ccc2nc(NC(=O)Cn3nnc4c3c(=O)n(C)c(=O)n4C)sc2c1] | 2-(4,6-dimethyl-5,7-dioxo-4,5,6,7-tetrahydro-1H-[1,2,3]triazolo[4,5-d]pyrimidin-1-yl)-N-(6-methoxybenzo[d]thiazol-2-yl)acetamide |
| 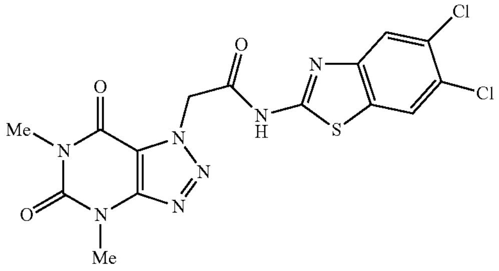 | N-(5,6-dichlorobenzo[d]thiazol-2-yl)-2-(4,6-dimethyl-5,7-dioxo-4,5,6,7-tetrahydro-1H-[1,2,3]triazolo[4,5-d]pyrimidin-1-yl)acetamide |
| 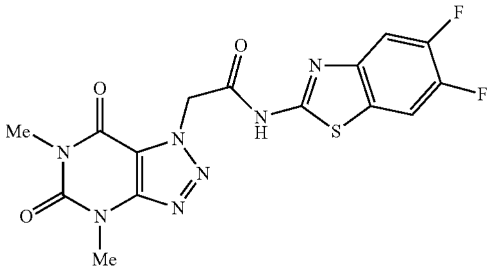 [SMILES: Cn1c(=O)c2c(nnn2CC(=O)Nc2nc3cc(F)c(F)cc3s2)n(C)c1=O] | N-(5,6-difluorobenzo[d]thiazol-2-yl)-2-(4,6-dimethyl-5,7-dioxo-4,5,6,7-tetrahydro-1H-[1,2,3]triazolo[4,5-d]pyrimidin-1-yl)acetamide |
| 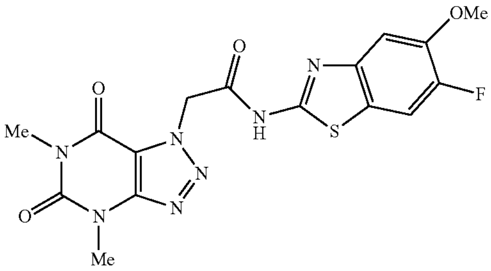 [SMILES: COc1cc2nc(NC(=O)Cn3nnc4c3c(=O)n(C)c(=O)n4C)sc2cc1F] | 2-(4,6-dimethyl-5,7-dioxo-4,5,6,7-tetrahydro-1H-[1,2,3]triazolo[4,5-d]pyrimidin-1-yl)-N-(6-fluoro-5-methoxybenzo[d]thiazol-2-yl)acetamide |
| 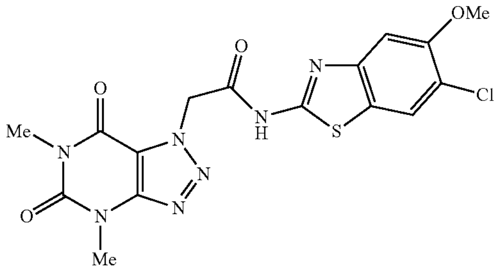 [SMILES: COc1cc2nc(NC(=O)Cn3nnc4c3c(=O)n(C)c(=O)n4C)sc2cc1Cl] | N-(6-chloro-5-methoxybenzo[d]thiazol-2-yl)-2-(4,6-dimethyl-5,7-dioxo-4,5,6,7-tetrahydro-1H-[1,2,3]triazolo[4,5-d]pyrimidin-1-yl)acetamide |
| 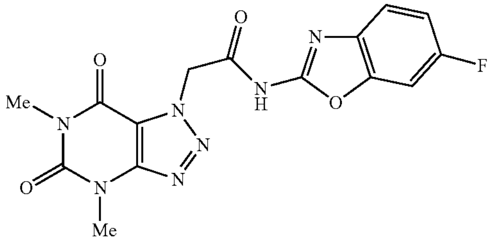 [SMILES: Cn1c(=O)c2c(nnn2CC(=O)Nc2nc3ccc(F)cc3o2)n(C)c1=O] | 2-(4,6-dimethyl-5,7-dioxo-4,5,6,7-tetrahydro-1H-[1,2,3]triazolo[4,5-d]pyrimidin-1-yl)-N-(6-fluorobenzo[d]oxazol-2-yl)acetamide |

TABLE 6-continued

| | |
|---|---|
| 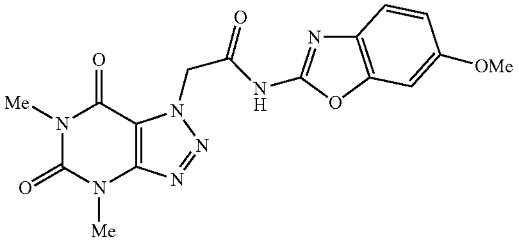 [SMILES: COc1ccc2nc(NC(=O)Cn3nnc4c3c(=O)n(C)c(=O)n4C)oc2c1] | 2-(4,6-dimethyl-5,7-dioxo-4,5,6,7-tetrahydro-1H-[1,2,3]triazolo[4,5-d]pyrimidin-1-yl)-N-(6-methoxybenzo[d]oxazol-2-yl)acetamide |
| 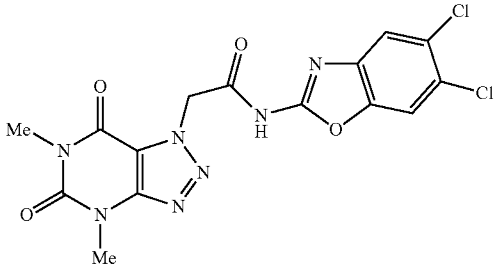 | N-(5,6-dichlorobenzo[d]oxazol-2-yl)-2-(4,6-dimethyl-5,7-dioxo-4,5,6,7-tetrahydro-1H-[1,2,3]triazolo[4,5-d]pyrimidin-1-yl)acetamide |
| 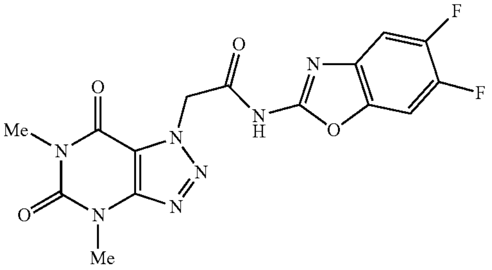 [SMILES: Cn1c(=O)c2c(nnn2CC(=O)Nc2nc3cc(F)c(F)cc3o2)n(C)c1=O] | N-(5,6-difluorobenzo[d]oxazol-2-yl)-2-(4,6-dimethyl-5,7-dioxo-4,5,6,7-tetrahydro-1H-[1,2,3]triazolo[4,5-d]pyrimidin-1-yl)acetamide |
| 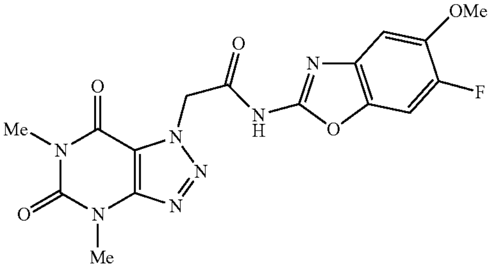 [SMILES: COc1cc2nc(NC(=O)Cn3nnc4c3c(=O)n(C)c(=O)n4C)oc2cc1F] | 2-(4,6-dimethyl-5,7-dioxo-4,5,6,7-tetrahydro-1H-[1,2,3]triazolo[4,5-d]pyrimidin-1-yl)-N-(6-fluoro-5-methoxybenzo[d]oxazol-2-yl)acetamide |
| 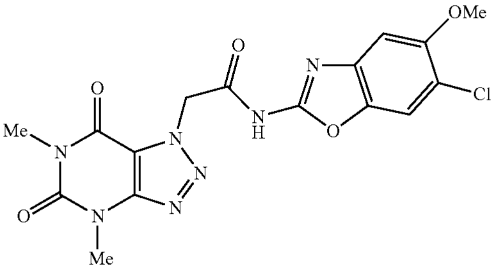 [SMILES: COc1cc2nc(NC(=O)Cn3nnc4c3c(=O)n(C)c(=O)n4C)oc2cc1Cl] | N-(6-chloro-5-methoxybenzo[d]oxazol-2-yl)-2-(4,6-dimethyl-5,7-dioxo-4,5,6,7-tetrahydro-1H-[1,2,3]triazolo[4,5-d]pyrimidin-1-yl)acetamide |

Compounds of Formula IX include those shown in Table 7.

TABLE 7

| | |
|---|---|
| 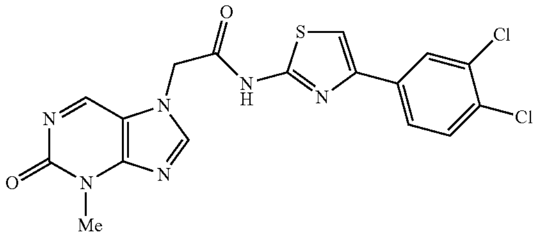 [SMILES: Cn1c(=O)ncc2c1ncn2CC(=O)Nc1nc(-c2ccc(Cl)c(Cl)c2)cs1] | N-(4-(3,4-dichlorophenyl)thiazol-2-yl)-2-(3-methyl-2-oxo-2,3-dihydropurin-7-yl)acetamide |

TABLE 7-continued

| | |
|---|---|
| 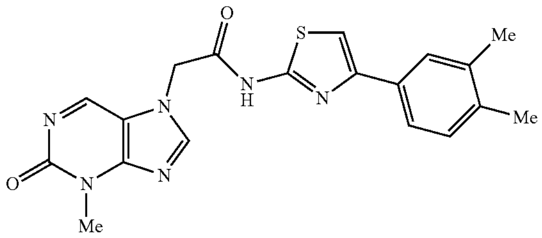 [SMILES: Cc1ccc(-c2csc(NC(=O)Cn3cnc4c3cnc(=O)n4C)n2)cc1C] | N-(4-(3,4-dimethylphenyl)thiazol-2-yl)-2-(3-methyl-2-oxo-2,3-dihydropurin-7-yl)acetamide |
| 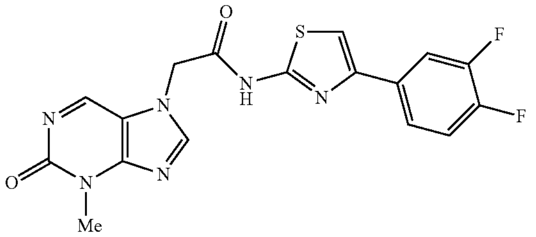 [SMILES: Cn1c(=O)ncc2c1ncn2CC(=O)Nc1nc(-c2ccc(F)c(F)c2)cs1] | N-(4-(3,4-difluorophenyl)thiazol-2-yl)-2-(3-methyl-2-oxo-2,3-dihydropurin-7-yl)acetamide |
| 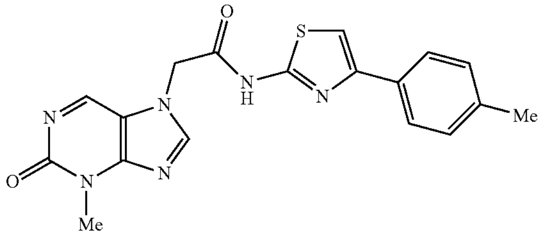 [SMILES: Cc1ccc(-c2csc(NC(=O)Cn3cnc4c3cnc(=O)n4C)n2)cc1] | 2-(3-methyl-2-oxo-2,3-dihydropurin-7-yl)-N-(4-p-tolylthiazol-2-yl)acetamide |
| 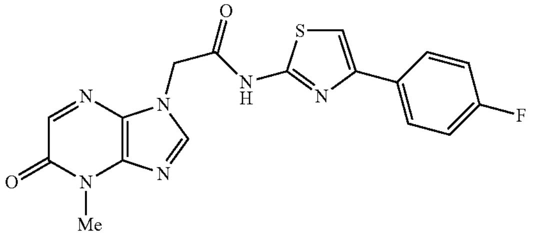 | N-(4-(4-fluorophenyl)thiazol-2-yl)-2-(4-methyl-5-oxo-4,5-dihydroimidazo[4,5-b]pyrazin-1-yl)acetamide |
| 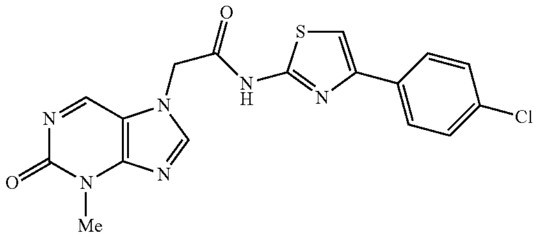 | N-(4-(4-chlorophenyl)thiazol-2-yl)-2-(3-methyl-2-oxo-2,3-dihydropurin-7-yl)acetamide |
| 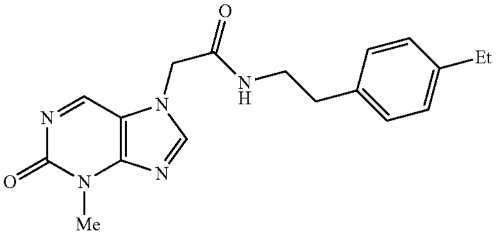 [SMILES: CCc1ccc(CCNC(=O)Cn2cnc3c2cnc(=O)n3C)cc1] | N-(4-ethylphenethyl)-2-(3-methyl-2-oxo-2,3-dihydropurin-7-yl)acetamide |

TABLE 7-continued

| | |
|---|---|
| 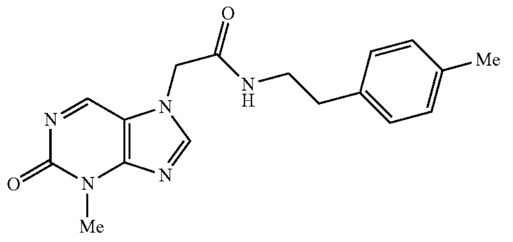 [SMILES: Cc1ccc(CCNC(=O)Cn2cnc3c2cnc(=O)n3C)cc1] | N-(4-methylphenethyl)-2-(3-methyl-2-oxo-2,3-dihydropurin-7-yl)acetamide |
| 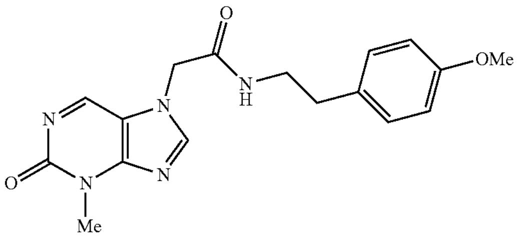 | N-(4-methoxyphenethyl)-2-(3-methyl-2-oxo-2,3-dihydropurin-7-yl)acetamide |
| 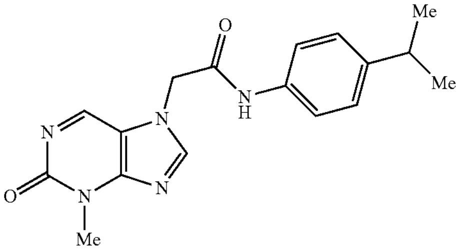 [SMILES: CC(C)c1ccc(NC(=O)Cn2cnc3c2cnc(=O)n3C)cc1] | N-(4-isopropylphenyl)-2-(3-methyl-2-oxo-2,3-dihydropurin-7-yl)acetamide |
| 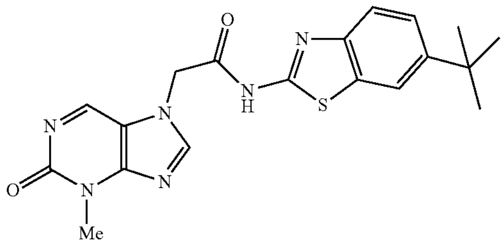 [SMILES: Cn1c(=O)ncc2c1ncn2CC(=O)Nc1nc2ccc(C(C)(C)C)cc2s1] | N-(6-tert-butylbenzo[d]thiazol-2-yl)-2-(3-methyl-2-oxo-2,3-dihydropurin-7-yl)acetamide |
| 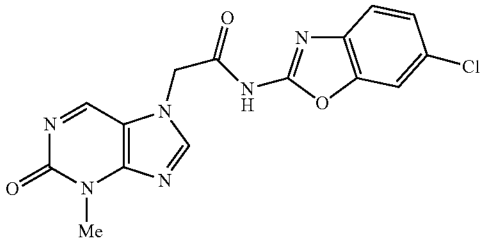 [SMILES: Cn1c(=O)ncc2c1ncn2CC(=O)Nc1nc2ccc(Cl)cc2o1] | N-(6-chlorobenzo[d]oxazol-2-yl)-2-(3-methyl-2-oxo-2,3-dihydropurin-7-yl)acetamide |
| 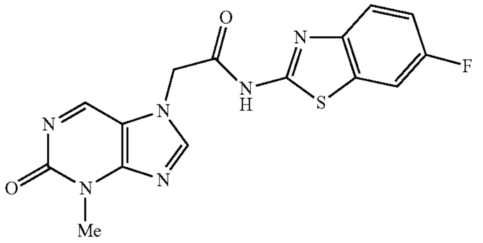 [SMILES: Cn1c(=O)ncc2c1ncn2CC(=O)Nc1nc2ccc(F)cc2s1] | N-(6-fluorobenzo[d]thiazol-2-yl)-2-(3-methyl-2-oxo-2,3-dihydropurin-7-yl)acetamide |

TABLE 7-continued

| | |
|---|---|
| 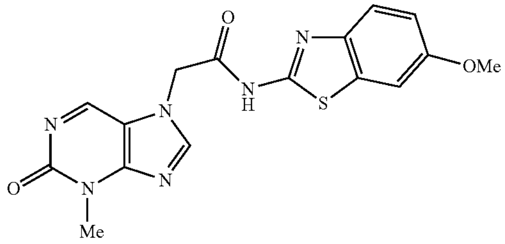 [SMILES: COc1ccc2nc(NC(=O)Cn3cnc4c3cnc(=O)n4C)sc2c1] | N-(6-methoxybenzo[d]thiazol-2-yl)-2-(3-methyl-2-oxo-2,3-dihydropurin-7-yl)acetamide |
| 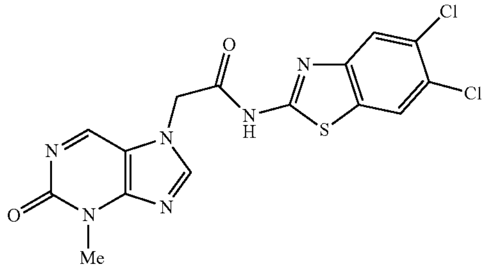 [SMILES: Cn1c(=O)ncc2c1ncn2CC(=O)Nc1nc2cc(Cl)c(Cl)cc2s1] | N-(5,6-dichlorobenzo[d]thiazol-2-yl)-2-(3-methyl-2-oxo-2,3-dihydropurin-7-yl)acetamide |
| 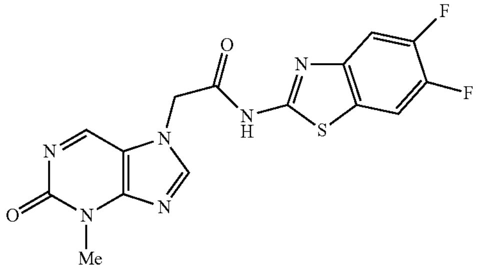 [SMILES: Cn1c(=O)ncc2c1ncn2CC(=O)Nc1nc2cc(F)c(F)cc2s1] | N-(5,6-difluorobenzo[d]thiazol-2-yl)-2-(3-methyl-2-oxo-2,3-dihydropurin-7-yl)acetamide |
| 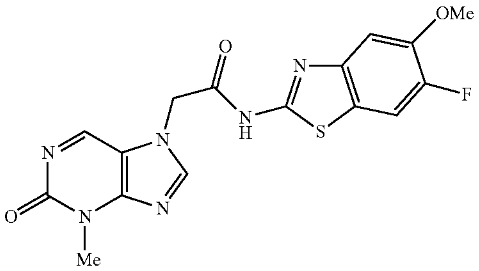 [SMILES: COc1cc2nc(NC(=O)Cn3cnc4c3cnc(=O)n4C)sc2cc1F] | N-(6-fluoro-5-methoxybenzo[d]thiazol-2-yl)-2-(3-methyl-2-oxo-2,3-dihydropurin-7-yl)acetamide |
| 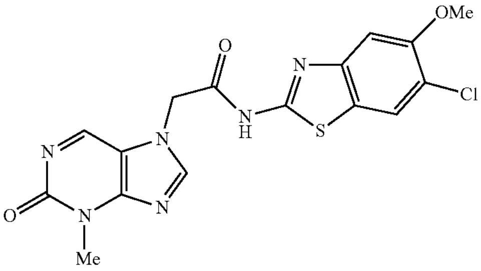 [SMILES: COc1cc2nc(NC(=O)Cn3cnc4c3cnc(=O)n4C)sc2cc1Cl] | N-(6-chloro-5-methoxybenzo[d]thiazol-2-yl)-2-(3-methyl-2-oxo-2,3-dihydropurin-7-yl)acetamide |
| 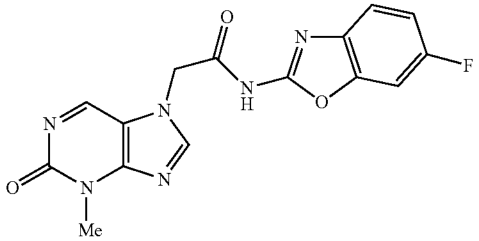 | N-(6-fluorobenzo[d]oxazol-2-yl)-2-(3-methyl-2-oxo-2,3-dihydropurin-7-yl)acetamide |

TABLE 7-continued

| | |
|---|---|
| 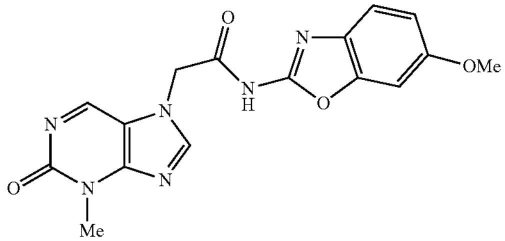 | N-(6-methoxybenzo[d]oxazol-2-yl)-2-(3-methyl-2-oxo-2,3-dihydropurin-7-yl)acetamide |
| 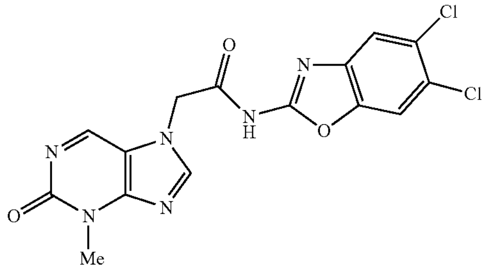 [SMILES: Cn1c(=O)ncc2c1ncn2CC(=O)Nc1nc2cc(Cl)c(Cl)cc2o1] | N-(5,6-dichlorobenzo[d]oxazol-2-yl)-2-(3-methyl-2-oxo-2,3-dihydropurin-7-yl)acetamide |
| 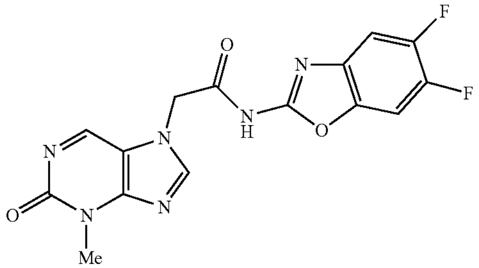 [SMILES: Cn1c(=O)ncc2c1ncn2CC(=O)Nc1nc2cc(F)c(F)cc2o1] | N-(5,6-difluorobenzo[d]oxazol-2-yl)-2-(3-methyl-2-oxo-2,3-dihydropurin-7-yl)acetamide |
| 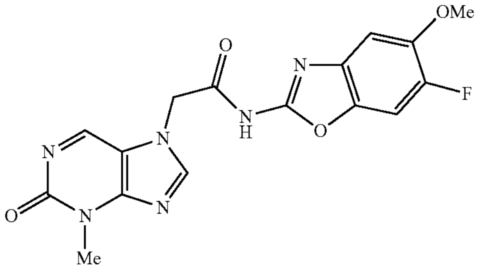 [SMILES: COc1cc2nc(NC(=O)Cn3cnc4c3cnc(=O)n4C)oc2cc1F] | N-(6-fluoro-5-methoxybenzo[d]oxazol-2-yl)-2-(3-methyl-2-oxo-2,3-dihydropurin-7-yl)acetamide |
| 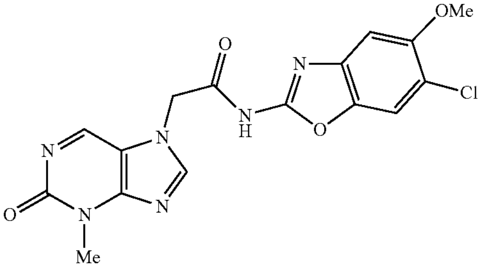 | N-(6-chloro-5-methoxybenzo[d]oxazol-2-yl)-2-(3-methyl-2-oxo-2,3-dihydropurin-7-yl)acetamide |

Certain compounds disclosed herein may exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. For example, if one chiral center is present in a molecule, the invention includes racemic mixtures, enantiomerically enriched mixtures, and substantially enantiomerically pure compounds. The composition can contain, e.g., more than 50%, more than 60%, more than 70%, more than 80%, more than 90%, more than 95%, or more than 99% of a single enantiomer.

The “enantiomeric excess” or “% enantiomeric excess” of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

Methods of preparing substantially isomerically pure compounds are known in the art. If, for instance, a particular enantiomer of a compound disclosed herein is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers. Alternatively, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Techniques for inverting or leaving unchanged a particular stereocenter, and those for resolving mixtures of stereoisomers are well known in the art, and it is well within the ability of one of skill in the art to choose an appropriate method for a particular situation. See, generally, Furniss et al. (eds.), *Vogel's Encyclopedia of Practical Organic Chemistry* 5th Ed., a Longman Scientific and Technical Ltd., Essex, 1991, pp. 809-816; and Heller, *Acc. Chem. Res.* 23: 128 (1990).

The compounds described herein may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds disclosed herein, whether radioactive or not, are intended to be encompassed within the scope of the present invention. For example, deuterated compounds and compounds incorporated $^{13}C$ are intended to be encompassed within the scope of the invention.

Certain compounds disclosed herein can exist in unsolvated forms as well as solvated forms, including hydrated forms. In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds disclosed herein. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19.)

In other cases, the compounds disclosed herein may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds disclosed herein. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

An antagonist of TRPA1 function may inhibit the outward current, the inward current, or both currents. Compounds that inhibit both currents may do so with the same or with differing $IC_{50}$ values. The inhibition of a particular current is measured by the ability to inhibit or reduce such current (e.g., inward and/or outward) in an in vitro or an in vivo assay. Compounds that inhibit any of the foregoing currents in an in vitro or in vivo assay are characterized as compounds that inhibit a function of TRPA1. Additionally or alternatively, a further exemplary function of TRPA1 that may be inhibited by the present compounds is ion flux mediated by TRPA1.

A compound described herein (e.g., a TRPA1 antagonist) can be chosen for a use described herein may be chosen because it inhibits a TRPA1 function with an $IC_{50}$ less than or equal to 10 uM, 5 uM, 1 uM, or less than or equal to 700, 600, 500, 400, 300, 250, 200, or 100 nM. In other embodiments, the compound described herein inhibits a TRPA1 function with an $IC_{50}$ less than or equal to 75 nM, less than or equal to 50 nM, or less than or equal to 25, 10, 5, or 1 nM.

In certain embodiments, inhibition of TRPA1 function means that a function, for example a TRPA1 mediated current, is decreased by greater than 50% in the presence of an effective amount of a compound in comparison to in the absence of the compound or in comparison to an ineffective amount of a compound. In certain other embodiments, the inhibition of a TRPA1 function means that a function, for example a TRPA1 mediated current or TRPA1 mediated ion flux, is decreased by at least 50%, 60%, 70%, 75%, 80%, 85%, or 90% in the presence of an effective amount of a compound in comparison to in the absence of the compound. In still other embodiments, the inhibition of a TRPA1 function means that a function, for example a TRPA1 mediated current, is decreased by at least 92%, 95%, 97%, 98%, 99%, or 100% in the presence of an effective amount of a compound in comparison to in the absence of the compound.

some embodiments, a compound described herein (e.g., a TRPA1 antagonist) can be characterized by some level of activity versus other ion channels (e.g., certain compounds are selective for inhibiting TRPA1 and other compounds exhibit a level of cross reactivity against one or more other ion channel). When a compound described herein is characterized by its activity against another ion channel, inhibition of a function or activity of the other ion channel is defined analogously to the way in which a function of a TRPA1 channel is defined. Thus, inhibiting the function of another ion channel means, for example, inhibiting ion flux mediated by that other ion channel or inhibiting the current mediated by that other ion channel.

In some embodiments, a compound described herein (e.g., a TRPA1 antagonist) is chosen for use because it is more selective for one TRP isoform than others, e.g., 10-fold, and more preferably at least 20, 40, 50, 60, 70, 80, or at least 100- or 1000-fold more selective for TRPA1 over one or more of TRPC6, TRPV5, TRPV6, TRPM8, TRPV1, TRPV2, TRPV4, and/or TRPV3. In other embodiments, the differential is smaller, e.g., it more strongly inhibits TRPA1 than TRPM8, TRPV1, TRPV2, TRPV3, and/or TRPV4, preferably at least twice, three times, five times, or ten times more strongly. Such comparisons may be made, for example, by comparing $IC_{50}$ values.

In other embodiments, a compound described herein (e.g., a TRPA1 antagonist) is chosen for use because it is more selective for TRPA1 than for other non-TRP ion channels, e.g., 10-fold, and more preferably at least 20, 40, 50, 60, 70, 80, or at least 100- or 1000-fold more selective for TRPA1 over one or more of NaV1.2, Cav1.2, Cav3.1, HERG, and/or mitochondrial uniporter. In other embodiments, the differential is smaller, e.g., it more strongly inhibits TRPA1 than NaV1.2, Cav1.2, Cav3.1, HERG, and/or mitochondrial uniporter, preferably at least twice, three times, five times, or ten times more strongly.

In certain embodiments, the compound described herein (e.g., a TRPA1 antagonist) inhibits TRPA1 with an $IC_{50}$ at least one order of magnitude more potent than its Ki for the alpha-amino-3-hydroxy-5-methyl-4-isoxazolepropionic acid (AMPA) receptor. In certain other embodiments, the compound described herein inhibits TRPA1 with an $IC_{50}$ at least two orders of magnitude, three orders of magnitude, or four orders of magnitude more potent than its Ki for the AMPA receptor. In certain embodiments, the compound described herein does not appreciably bind the AMPA receptor. In other words, the compound described herein inhibits TRPA1 with a particular $IC_{50}$ and, when administered at that concentration, the antagonist does not appreciably bind the AMPA receptor.

In certain embodiment, a compound is chosen because it antagonizes the function of TRPA1 and the function of TRPM8, TRPV1 and/or TRPV3. Although such compounds selectively antagonize the function of more than one ion channel, the $IC_{50}$ values for the different ion channels need not be identical.

The $IC_{50}$ values are measured in vitro using, for example, patch clamp analysis or standard measurements of calcium flux. Exemplary in vitro methods for calcium flux-based $IC_{50}$ estimation are described in Example 2. Methods used to obtain more definitive $IC_{50}$ measurements are described in Example 3. Alternatively, estimates of % inhibition of current or ion flux can also be calculated and used to assess efficacy of a compound as an inhibitor.

Indications

Movement of ions across cellular membranes is carried out by specialized proteins. TRP channels are one large family of non-selective cation channels that function to help regulate ion flux and membrane potential. Non-selective cation channels such as TRPA1 modulate the flux of calcium and sodium ions across cellular membranes. Sodium and calcium influx leads to depolarization of the cell. This increases the probability that voltage-gated ion channels will reach the threshold required for activation. As a result, activation of non-selective cation channels can increase electrical excitability and increase the frequency of voltage-dependent events. Voltage-dependent events include, but are not limited to, neuronal action potentials, cardiac action potentials, smooth muscle contraction, cardiac muscle contraction, and skeletal muscle contraction.

Calcium influx caused by the activation of non-selective cation channels such as TRPA1 also alters the intracellular free calcium concentration. Calcium is a ubiquitous second messenger molecule within the cell, so alterations in intracellular calcium levels have profound effects on signal transduction and gene expression. As a result, activation of non-selective cation channels such as TRPA1 can lead to changes in gene expression and cellular phenotype. Gene expression events include, but are not limited to, production of mRNAs encoding cell surface receptors, ion channels, and kinases. These changes in gene expression can lead to hyperexcitability in that cell.

Modulating the function of TRPA1 proteins provides a means of modulating calcium homeostasis, sodium homeostasis, membrane polarization, and/or intracellular calcium levels, and compounds that can modulate TRPA1 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis.

Bautista et al. have reported that TRPA1 mediates the inflammatory actions of agents such as acrolein, which causes the inflammatory and toxic actions of tear gas. (Bautista et al., Cell (2006) 124:1269-82.) Bessac et al. have shown that hypochlorite—the main mediator of chlorine irritancy—activates $Ca^{2+}$ influx and membrane currents in sensory neurons cultured from $Trpa1^{+/+}$ mice, while the influx of $Ca^{2+}$ was absent in neurons cultured from $Trpa1^{-/-}$ mice. In addition, Bessac et al. compared the responses of $Trpa1^{+/+}$ mice and $Trpa1^{+/+}$ mice to NaOCl exposure. The $Trpa1^{+/+}$ mice showed much more respiratory depression than did the $Trpa1^{-/-}$ mice. (Bessac et al., Journal of Clinical Investigation (2008) 18:1899-1910) These data suggest that TRPA1 antagonists could be useful to treat or prevent the effects of chemical warfare agents including tear gas and chlorine.

Chemical Warfare Agents

A subject may be exposed to a chemical warfare agent, e.g., by inhalation or by contact with the skin. If a compound described herein (e.g., a TRPA1 antagonist) is administered, the symptoms or injuries resulting from the exposure to the chemical warfare agents can be reduced, prevented, or both. The compound described herein can be administered to a subject before, during, or following such exposure and is therefore administered within 24 hours, 18 hours, 6 hours, 4 hours, 3 hours, 2 hours, 1 hour, 30 minutes, 20 minutes, 10 minutes, 5 minutes, one minute, or thirty seconds before or after such exposure. The TRPA1 anta compound described herein gonist can be administered prophylactically, when exposure to an agent is anticipated. It can also be administered after exposure to the chemical warfare agent (e.g., before or after symptoms of injury present in a subject).

Injuries resulting from the exposure to chemical warfare agents are known in the art and include any physical injuries, such as injuries to the skin, eyes, respiratory tract, musculoskeletal system, circulatory system, gastrointestinal tract, central nervous system, peripheral nervous system, heart, liver, lungs, and kidneys. Exemplary symptoms or injuries resulting from the exposure to chemical warfare agents include inflammation, burn, itch, pain, rash, blisters, sweating, muscle twitching, nausea, vomiting, diarrhea, weakness, loss of conciousness, convulsions, muscular twitching, paralysis, secretions (from the mouth, nose, or lung for example), difficulty breating, blurred vision, eye pain, lacrimation, red eyes, shortness of breath, coughing, phlegm production and narrowing of the airways, headaches, tremors, dizziness, numbness or tingling, anxiety, insomnia, depression, emotional instability, and even death. The term "chemical warfare agent" includes all of those agents classified as schedule 1, 2, and 3 agents under the Chemical Weapons Convention of 1993 and may be in liquid form, gas form, solid form, or combinations thereof. Exemplary agents are described in further detail below and include, for example, nerve agents, blood agents, blister agents, pulmonary agents, incapacitating agents, and toxins. Other agents include methyl isocyanate, hexamethylene diisocyanate, 2,4-toluene-diisocyanate, and diphenylmethane-4,4-diisocyanate (MDI).

Nerve agents. Nerve agent poisoning typically leads to contraction of pupils, profuse salivation, convulsions, involuntary urination and defecation, and eventual death by asphyxiation as control is lost over respiratory muscles. These symptoms are reduced or prevented by the administration of the TRPA1 antagonists. Exemplary agents include G agents such as tabun (GA), sarin (GB), soman (GD), cyclosarin (GF), and GV; V agents such as VE, VG, VM, VX, and Novichok agents.

Blood agents. A blood agent (or cyanogen agent) is a compound containing a cyanide group that prevents the body from utilizing oxygen. These agents exert their toxic effect at the cellular level by directly interrupting cellular respiration. Exemplary agents include cyanogen chloride, hydrogen cyanide, and hydrogen sulfide.

Blister agents. Blister agents or vesicants typically cause severe skin, eye and mucosal pain and irritation. These agents also have the ability to cause large, painful water blisters. Blister agents include, for example, lewisites, nitrogen mustard, sulfur mustard, ethyldichloroarsine (a lewisite analog; ED), methyldichloroarsine (MD), phenyldichloroarsine (PD), and phosgene oxime (CX). Lewisites include, for example, 2-Chlorovinyldichloroarsine (Lewisite 1), Bis(2-chlorovinyl)chloroarsine (Lewisite 2), and Tris(2-chlorovinyl)arsine (Lewisite 3). Exemplary nitrogen mustards are bis(2-chloroethyl)ethylamine (HN1), bis(2-chloroethyl)methylamine (HN2), and tris(2-chloroethyl)amine (HN3). Sulfur mustards include, for example, 1,2-Bis(2-chloroethylthio) ethane (Sesquimustard; Q), 1,3-Bis(2-chloroethylthio)-n-propane, 1,4-Bis(2-chloroethylthio)-n-butane, 1,5-Bis(2-chloroethylthio)-n-pentane, 2-Chloroethylchloromethylsulfide, bis(2-chloroethyl) sulfide (Mustard gas; HD), bis(2-chloroethylthio) methane, bis (2-chloroethylthiomethyl) ether, and bis(2-chloroethylthioethyl) ether (O Mustard).

Pulmonary agents. A pulmonary agent (or choking agent) is a chemical weapon agent designed to impede a subject's ability to breathe, resulting in suffocation. Exemplary agents include adamsite (DM), acrolein, bis(chloromethyl) ether (BCME), chlorine ($Cl_2$), chloropicrin (PS), diphosgene (DP), methyl chlorosulfonate, phosgene (CG), and stannic chloride.

Incapacitating agents. Incapacitating agents or riot-control agents typically produce temporary physiological or mental effects, or both, such that individuals who are exposed to them are incapable of concerted effort. Upon their exposure, lachrymatory agents (or lachrymators) for example, irritate the eyes to cause tearing, pain, and even temporary blindness. The most common lachrymatory agents are tear gas and pepper spray and include, for example, a-Chlorotoluene, benzyl bromide, bromoacetone (BA), bromobenzylcyanide (CA) bromomethyl ethyl ketone, capsaicin (OC), chloracetophenone (Tear gas; CN), chloromethyl chloroformate, dibenzoxazepine (CR), ethyl iodoacetate, ortho-chlorobenzylidene malononitrile (Super tear gas; CS), trichloromethyl chloroformate, and xylyl bromide. Other incapacitating agents include, for example, 3-Quinuclidinyl benzilate (psychedelic; BZ), hydrocyanic acid (paralytic), diphenylchloroarsine (sternutatory; DA), diphenylcyanoarsine (DC), and KOLOKOL-1 (tranquilizer).

Toxins. Exemplary toxins are abrin, ricin, and saxitoxin.

Pharmaceutical Compositions

While it is possible for a compound disclosed herein to be administered alone, it is preferable to administer the compound as a pharmaceutical formulation, where the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

The tablets, and other solid dosage forms of the pharmaceutical compositions disclosed herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The formulations disclosed herein can be delivered via a device. Exemplary devices include, but are not limited to, a catheter, wire, stent, or other intraluminal device. Further exemplary delivery devices also include a patch, bandage, mouthguard, or dental apparatus. Transdermal patches have the added advantage of providing controlled delivery of a compound disclosed herein to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Another example of a device is a metered dose aerosol dispenser containing an aerosol pharmaceutical composition for pulmonary or nasal delivery comprising an agent that inhibits a TRPA1-mediated current with an $IC_{50}$ of 1 micromolar or less. For instance, it can be a metered dose inhaler, a dry powder inhaler or an air-jet nebulizer.

Ophthalmic formulations, eye ointments, drops, solutions and the like, are also contemplated as being within the scope of this invention.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally or by inhalation.

Particularly useful modes of administration include topical administration, intramuscular injection, inhalation, topical ocular administration (e.g., via eye drops), or oral administration.

Combination Therapy

Another aspect of the invention provides a conjoint therapy wherein one or more other therapeutic agents are administered with a compound described herein (e.g., a TRPA1 modulator such as an antagonist). Such conjoint treatment may be achieved by way of the simultaneous, sequential, or separate dosing of the individual components of the treatment.

In certain embodiments, two or more compounds of the invention are conjointly administered. When two or more compounds of the invention are conjointly administered, the two or more compounds may have a similar selectivity profile and functional activity, or the two or more compounds may have a different selectivity profile and functional activity. By way of example, the two or more compounds may both be approximately 10, 100, or 1000 fold selective for antagonizing a function of TRPA1 over TRPV1, TRPV5, and TRPV6 (e.g., the two or more compounds have a similar selectivity profile), and further may inhibit a function of TRPA1 with a similar IC50 (e.g., a similar functional activity). Alternatively, the one of the two or more compounds may selectively inhibit TRPA1 while the other of the two or more compounds inhibits both TRPA1 and TRPV1 (e.g., the two or more compounds have differing selectivity profiles). Administration of combinations of two or more compounds of the invention having similar or differing properties are contemplated.

In certain embodiments, a compound of the invention is conjointly administered with one or more additional compounds that antagonize the function of a different channel. By way of example, a compound of the invention may be conjointly administered with one or more compounds that antagonize TRPV1, TRPM8, and/or TRPV3. The compound(s) that antagonize TRPV1, TPRM8, or TRPV3 may be selective for TRPV1, TRPM8 or TRPV3 (e.g., inhibit TRPV1 or TRPV3 10, 100, or 1000 fold more strongly than TRPA1). Alternatively, the compound(s) that antagonize TRPV1 or TRPV3 may cross react with other TRP channels.

In certain other embodiments, a compound of the invention is conjointly administered with one or more additional agents or therapeutic regimens appropriate for the particular injury being treated. For example, current treatments for injuries caused by exposure to nerve agents include treatment with atropine and Pralidoxime chloride (2-PAM). Injuries caused by exposure to cyanides are currently treated with. Scavengers such as human plasma-derived butyrylcholinesterase (HuBuChE), anti-epilectic drugs and neutralizing decontamination solutions such as 0.5% hypochloriate are also used to treat such injuries. Treatments for cyanide poisoning include hydroxocobalamin, sodium nitrite, and rhodanase. M291 resin kits are also currently used to treat topical injuries resulting from exposure to chemical warfare agents. Any of these agents can be combined with the TRPA1 antagonists described herein.

Dosages

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. For example, the dose can be 1-50, 1-25, or 5-10 mg/kg.

Disease and Injury Models

Compounds that antagonize TRPA1 function may be useful in the prophylaxis and treatment of any of the foregoing injuries, diseases, disorders, or conditions. In addition to in vitro assays of the activity of these compounds, their efficacy can be readily tested in one or more animal models. Compounds that may reduce pain or other undesirable symptoms in the animals can be readily tested by observing behavioral and/or physical characteristics of challenged animals in the presence versus the absence of the test compound(s) or procedure.

Mouse Ear Edema Model. The mouse ear edema model provides a quantitative edema response as well as histopathological and biochemical endpoints as measurements of inflammation and tissue damage following exposure to the chemical warfare agent half mustard. The model is performed using CD-1 mice. Twenty-four hours following IP administration of test compound or vehicle, a solution of half mustard in organic solvent is applied to the inner surface of the right ear of each mouse. The left ear is not treated with half mustard and instead is maintained as a control. Animals are sacrificed at 24 hours, 72 hours, and 7 days post exposure to half mustard. The ear weights, draize scoring, and pathology are recorded at each time point. Half mustard injury in the mouse ear is measured by both edema response (fluid accumulation) and histopathological damage (necrosis, epidermal-dermal separation).

In an alternate model, the test compound is administered therapeutically, e.g., immediately after, or one hour after exposure to half mustard. The models can also be performed using sulfur mustard or nitrogen mustard instead of half mustard.

Guinea Pig Model for Nerve Agent Challenge. A Guinea pig model can be used to study the protective effects of the compounds against mortality induced by a nerve agent. The animals are pretreated with two IP doses of test compound, one IM dose of atropine, one IM dose of 2-PAM, or two IP doses of vehicle before challenge with 2×LD50 (s.c.) of a nerve agent. The animals are observed at 6 observation times post challenge. The number of animals in each group surviving 24 hours post challenge is then recorded.

In an alternate model, the test compound, atropine, and 2-PAM are administered therapeutically, e.g., immediately after, or one hour after exposure to the nerve agent.

The following examples are meant to be illustrative and are not meant to be limiting in any way.

Example 1

High Throughput Screening Assay

The assay depended on detection of the rise in intracellular $Ca^{2+}$ concentration ($[Ca^{2+}]_i$) following channel activation in cells inducibly expressing the TRPA1 channel. $Ca^{2+}$ rise was quantified with the use of fluorescent $Ca^{2+}$ indicators that were loaded into cells and thereafter indicated the $[Ca^{2+}]_i$. $Ca^{2+}$ influx followed activation of the TRPA1 channel. Compounds inhibiting the $[Ca^{2+}]_i$ rise were considered hits for further investigation.

The commercially available HEK293/TREx line (Invitrogen) was stably transfected with a TRPA1 construct (specifically a construct encoding a TRPA1 protein with an amino acid sequence depicted in SEQ ID NO: 1 of WO 2007/073505) and screened by conventional calcium imaging to find clones with TRPA1 expression following stimulation with 1 μg/ml tetracycline. These cells were maintained in the growth medium recommended by the manufacturer supplemented with 100 μg/ml hygromycin to promote retention of the TRPA1 construct. After growing to near confluency, cells were plated at a density of ~25,000 cells/well in 384 well CellBind plates (Corning) in the presence of 1 μg/ml tetracycline, and allowed to grow for 20-30 hrs. A nearly confluent monolayer resulted. Cells were then loaded with $Ca^{2+}$ dye: Fura-2/AM or Fluo4/AM was added to the wells to a final concentration of 2 μM or 1 μM, respectively, and incubated for ~60 min at room temperature. Supernatant was then removed from the cells by inverting plates with a sharp flick, and Hank's Balanced Salt Solution (HBSS; 0.185 g/l D-glucose, 0.9767 g/l $MgSO_4$ (anhydrous), 0.4 g/l KCl, 0.06 g/l $KH_2PO_4$ (anhydrous), 0.35 g/l $NaHCO_3$, 8.0 g/l NaCl, and 0.04788 g/l $Na_2HPO_4$ (anhydrous); pH 7.4) was then added to each well. Following recovery from loading, cells were assayed using the Hamamatsu FDSS 6000 system, which permitted illumination alternately at 340 nM and 380 nM for Fura-2 experiments, or at 485 nM for Fluo4 experiments. Frames were acquired at a rate of 0.2 Hz. For the screening assay, a diluted stock (at 50 μM) of compounds to be tested was added to each well for 2 minutes following the collection of a short (4 frame) baseline. AITC (allylisothiocyanate) was then added to each well, achieving a final concentration of 10 μM each compound and 7.5 μM AITC. Data were collected for at least 3 minutes following addition of AITC, and evaluated for the $[Ca^{2+}]_i$, which is proportional to the fluorescent intensity (for Fluo4) or the F340/F380 ratio (for Fura-2). Negative controls consisted of HEK293/TREx TRPA1 cells exposed to AITC, but no compound. Positive control cells were usually HEK293/TREx ("parental") cells exposed to AITC but no compound, but sometimes normal HEK/293 TREx TRPA1 cells were also used, but not exposed to AITC or compound. These controls defined a screening window, and "hits" were defined as those compounds inhibiting the fluorescence response by at least 40%. $IC_{50}$ values were determined for compounds defined as "hits." The Fluo4 cell-based fluorescence assay was used to determine the intracellular $Ca^{2+}$ concentration in the presence of varying drug concentration. To determine $IC_{50}$ values, concentrations tested were 40 μM, 20 μM, 10 μM, 5 μM, 2.5 μM, 1.25 μM, and 0.625 μM. Compounds were tested in triplicate at all concentrations. Standard software was used to fit $IC_{50}$ curves.

Additionally or alternatively, potency can be represented as % inhibition of a response in the presence (of a given concentration of compound) versus the absence of compound or in comparison to a control compound. For example, efficacy can be represented as % inhibition of ion flux in the presence versus the absence of compound.

Example 2

Patch Clamp Experiments

Patch clamp experiments permit the detection of currents through the TRPA1 channel in the cell line described above. The whole-cell configuration of the patch clamp technique was used to test the compounds described herein. In normal whole-cell patch clamp recordings, a glass electrode is brought into contact with a single cell and a high-resistance (gigaohm) seal is established with the cell membrane. The membrane is then ruptured to achieve the whole-cell configuration, permitting control of the voltage of the cell membrane and measurement of currents flowing across the membrane using the amplifier attached to the electrode and resulting in the replacement of cytoplasm with the pipette solution.

HEK293/TREx TRPA1 cells were induced in the presence of 1 μg/ml tetracycline for 20-48 hours, removed from growth plates, and replated at low density (to attain good single-cell physical separation) on glass coverslips for measurement. In some cases, cells were grown in low density overnight on glass coverslips. Potential blockers were tested for ability to block current in the continued presence of AITC.

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of treating an injury to the skin or respiratory tract resulting from exposure to a chemical warfare agent in a subject in need thereof, the method comprising administering to the subject a compound of Formula (II) or a salt thereof Formula (II)

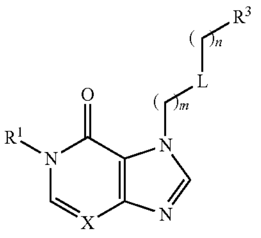

wherein, $R^1$ is $C_1$-$C_6$ alkyl, $C_2$-$C_6$ alkenyl, or $C_2$-$C_6$ alkynyl, each of which is optionally substituted with 1-4 $R^5$;

X is N or $CR^2$;

$R^2$ is H, $C_1$-$C_6$ alkyl, $C_2$-$C_6$ alkenyl, or $C_2$-$C_6$ alkynyl, each of which is optionally substituted with 1-4 $R^5$;

L is $NR^6SO_2$, $SO_2NR^6$, $OC(O)NR^6$, $NR^6C(O)O$, $NR^6C(O)NR^6$, $NR^6C(O)$, $C(O)NR^6$, C(O), O, S, S(O), $S(O)_2$, $NR_6$, $CH_2$, cyclyl, aryl, heterocyclyl, or heteroaryl;

$R^3$ is cyclyl, heterocyclyl, aryl, heteroaryl, each of which is optionally substituted with 1-4 $R^7$;

each $R^5$ is independently halo, hydroxyl, alkoxy, amino, alkylamino, dialkylamino, cyano, nitro, amido, alkylamido, dialkylamido, thioyl, sulfonyl, cyclyl, heterocyclyl, aryl, or heteroaryl;

each $R^6$ is independently H, $C_1$-$C_6$ alkyl, arylalkyl, S(O) alkyl, acetyl, amidyl, or S(O)H;

each $R^7$ is independently $C_1$-$C_6$ alkyl, $C_2$-$C_6$ alkenyl, $C_2$-$C_6$ alkynyl, cyclyl, heterocyclyl, aryl, heteroaryl, halo, hydroxyl, alkoxy, aryloxy, arylalkoxy, amino, alkylamino, dialkylamino, thioyl, alkylthioyl, sulfonyl, sulfonamidyl, amido, urea, sulfonylurea, hydroxyl alkoxyl, alkoxy alkoxyl, acyl, nitro, cyano, each of which is independently substituted with 1-3 $R^8$;

each $R^8$ is independently $C_1$-$C_6$ alkyl, $C_2$-$C_6$ alkenyl, $C_2$-$C_6$ alkynyl, halo, hydroxyl, alkoxy, aryloxy, amino, alkylamino, dialkylamino, thioyl, sulfonyl, sulfonamidyl, amido, urea, sulfonylurea, acyl, nitro, cyano, cyclyl, heterocyclyl, aryl, or heteroaryl;

each m and n are independently 0, 1, 2, 3, 4, 5, or 6, wherein m is at least 2 when L is connected to the methylene carbon via a heteroatom; and each $R^9$ is independently H, $C_1$-$C_6$ alkyl, $C_2$-$C_6$ alkenyl, $C_2$-$C_6$ alkynyl, halo, hydroxyl, alkoxy, aryloxy, arylalkoxy, amino, alkylamino, dialkylamino, thioyl, alkylthioyl, sulfonyl, sulfonamidyl, amido, urea, sulfonylurea, acyl, nitro, cyano, each of which is independently substituted with 1-3 $R^8$.

2. The method of claim 1, wherein the compound is administered orally.

3. The method of claim 1, wherein the compound is administered via intramuscular injection.

4. The method of claim 1, wherein the compound is administered topically.

5. The method of claim 1, wherein the compound is administered via topical ocular administration.

6. The method of claim 1, wherein the chemical warfare agent is tear gas.

7. The method of claim 1, wherein the chemical warfare agent is chlorine.

8. The method of claim 1, wherein the chemical warfare agent is mustard gas.

9. The method of claim 1, wherein the subject is a human.

10. The method of claim 1, wherein $R^1$ is $C_1$-$C_6$ alkyl.

11. The method of claim 1, wherein X is $CR^2$.

12. The method of claim 1, wherein $R^2$ is H or $C_1$-$C_6$ alkyl.

13. The method of claim 1, wherein L is $C(O)R^6$ and m is 0 or 1.

14. The method of claim 1, wherein $R^3$ is heteroaryl, substituted with 1-4 $R^7$.

15. The method of claim 1, wherein $R^3$ is a 6-membered nitrogen-containing heteroaryl, substituted with 1 $R^7$.

16. The method of claim 1, wherein $R^7$ is aryl, heteroaryl, or heterocyclyl, each of which is optionally substituted with 1-3 $R^8$.

17. The method of claim 1, wherein n is 0 or 1.

18. The method of claim 1, wherein the compound is a compound selected from the group consisting of:

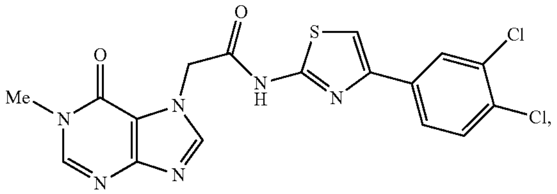

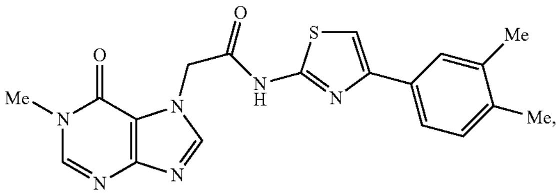

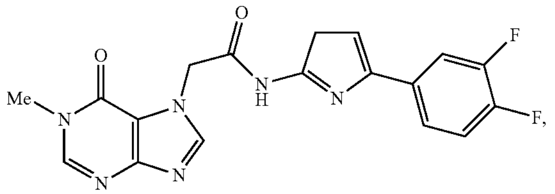

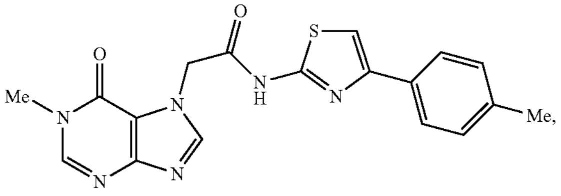

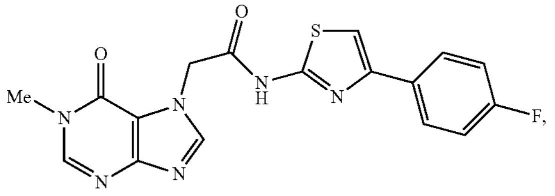

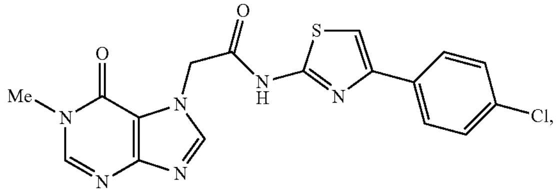

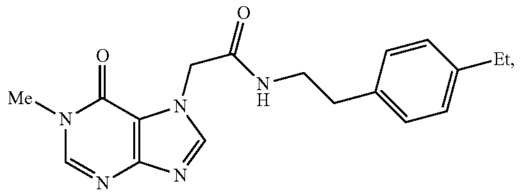

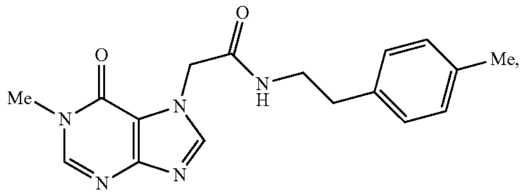

-continued
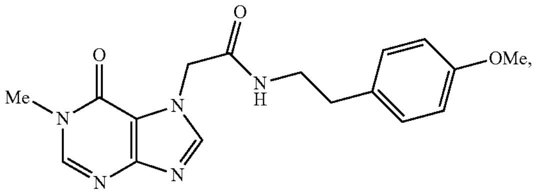
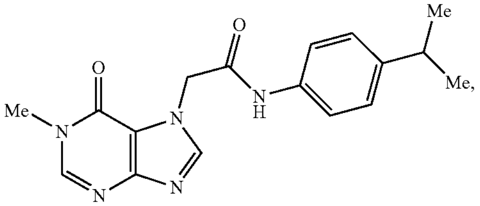
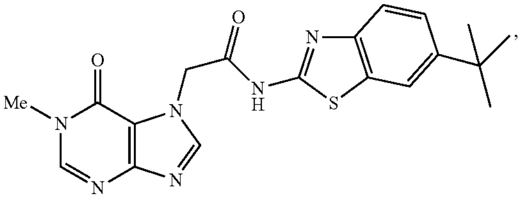
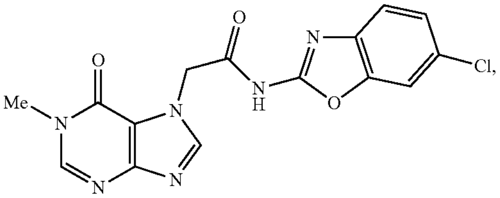
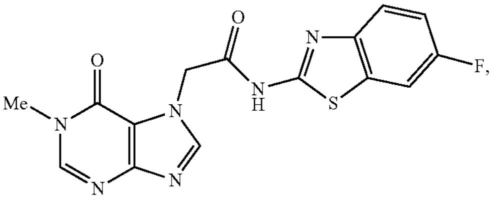
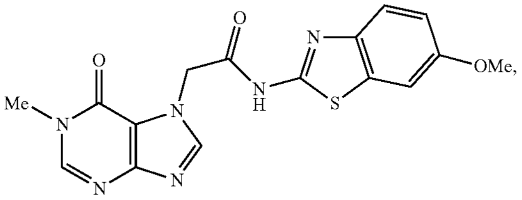
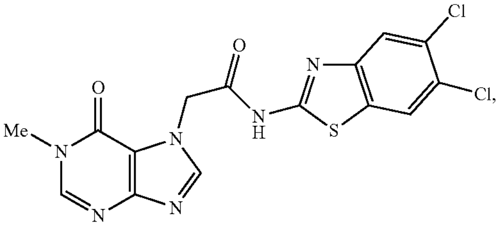
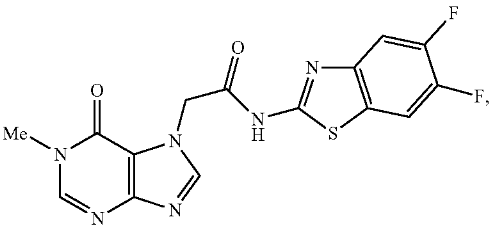
-continued
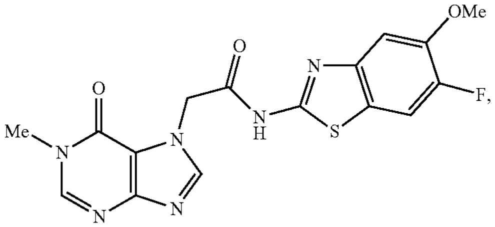
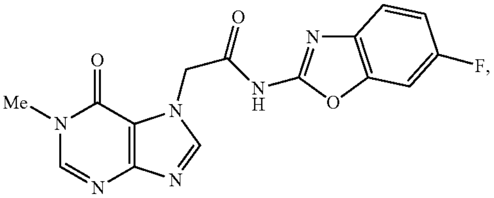
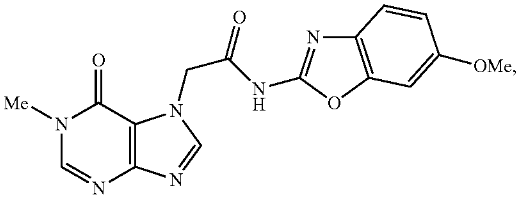
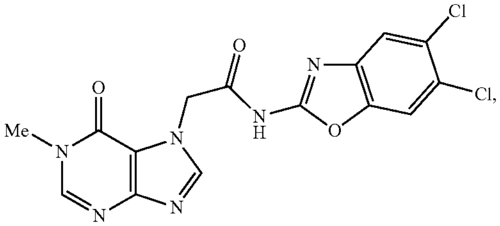
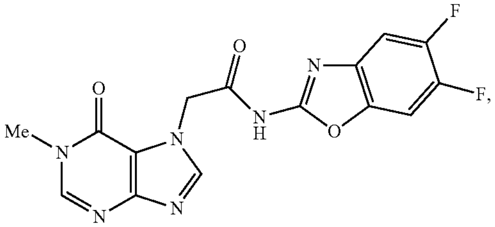
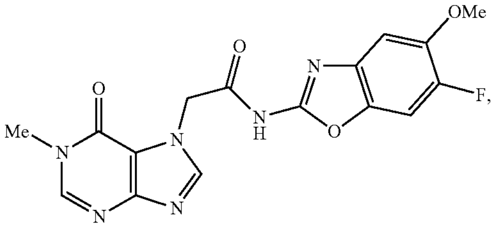
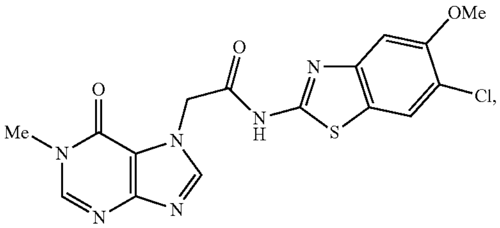

-continued
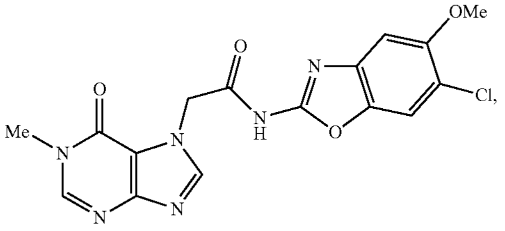
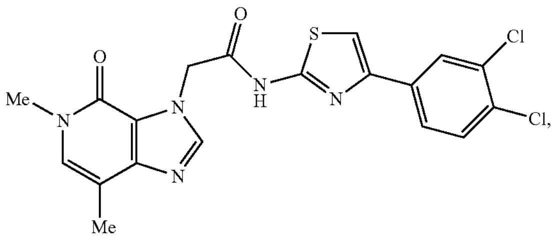
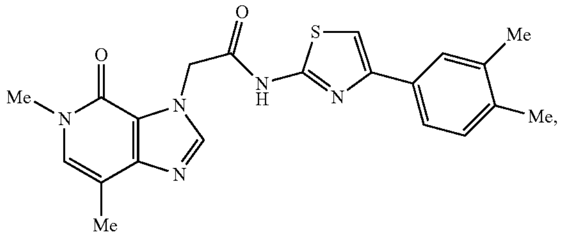
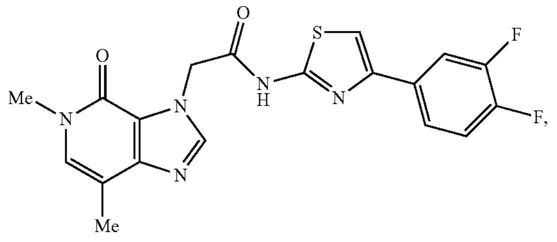
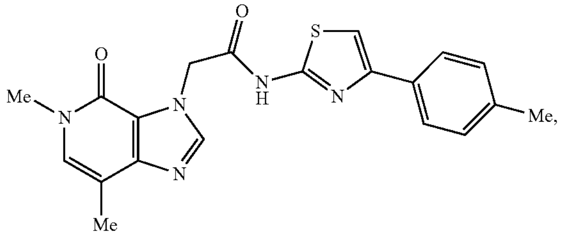
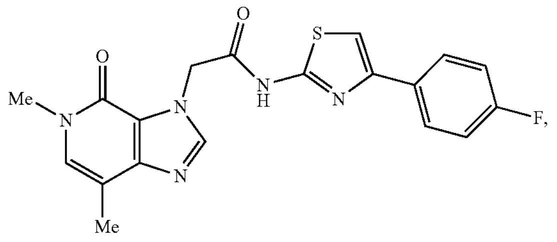
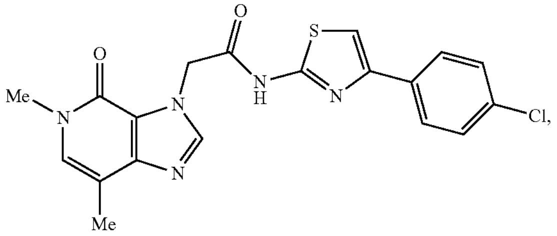
-continued
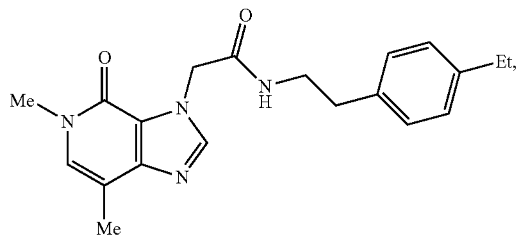
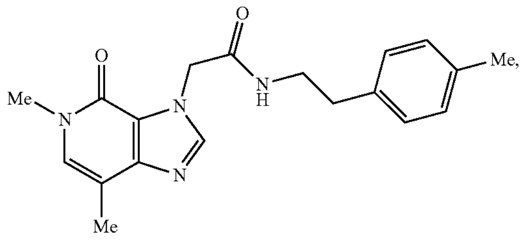
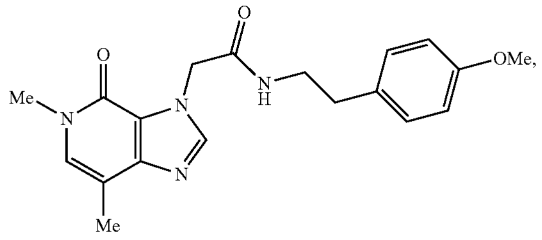
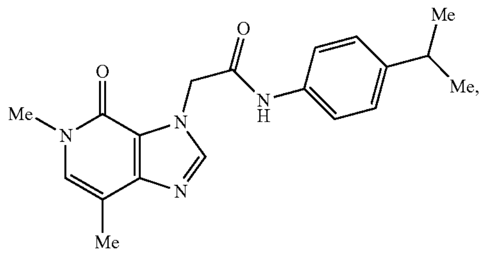
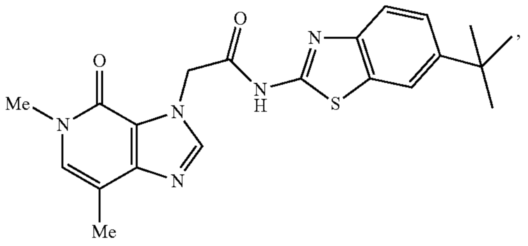
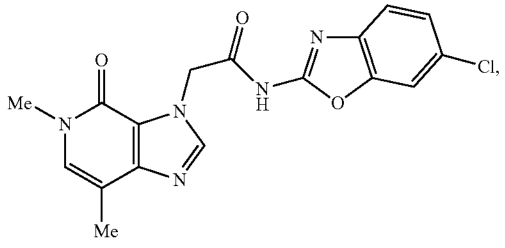
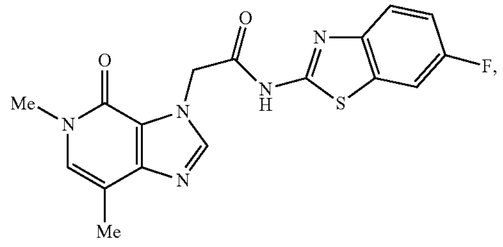

-continued
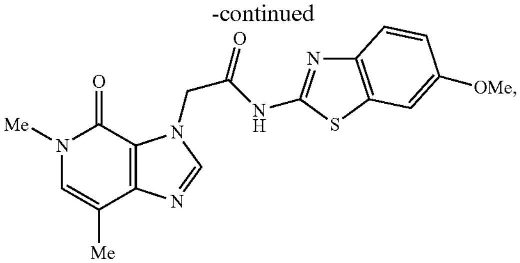,
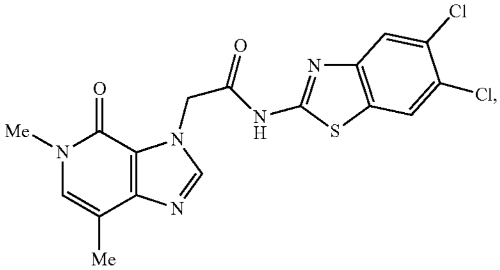,
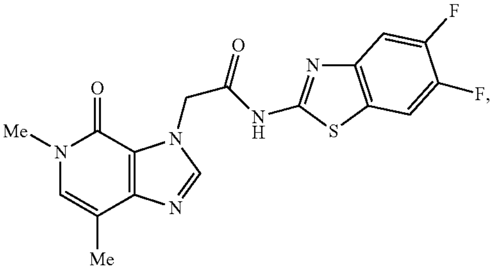,
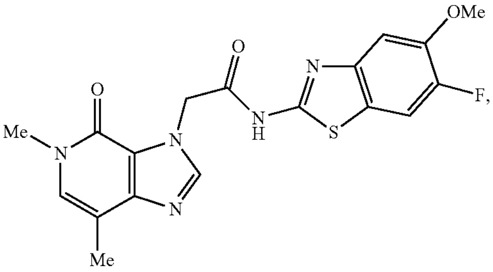,
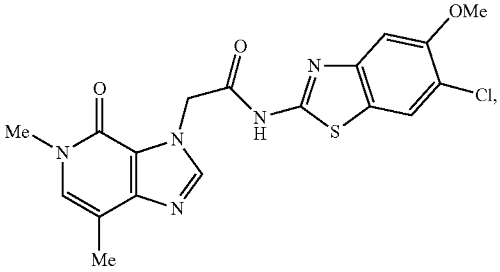,
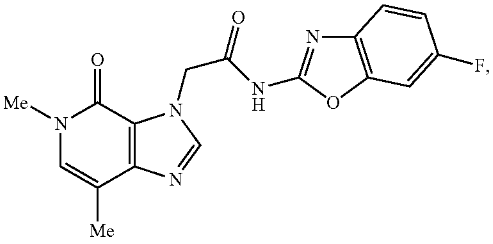,
-continued
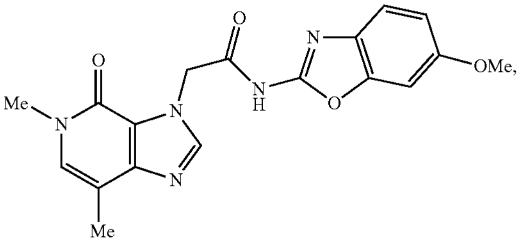,
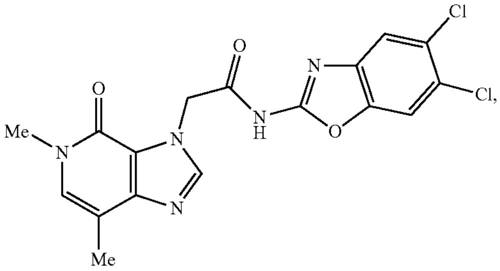,
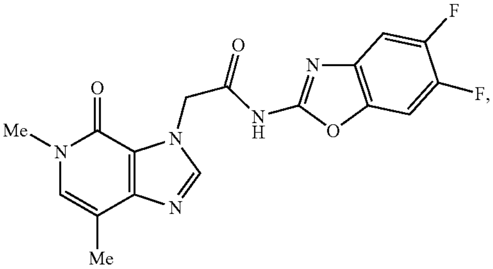,
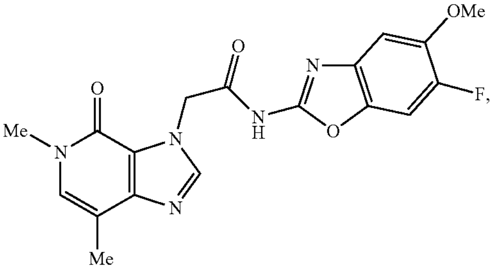,
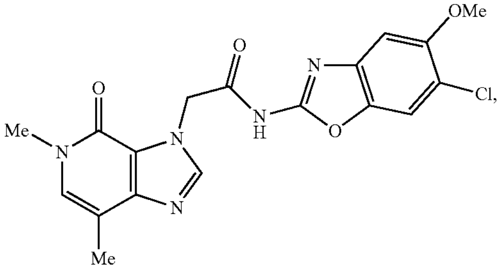,
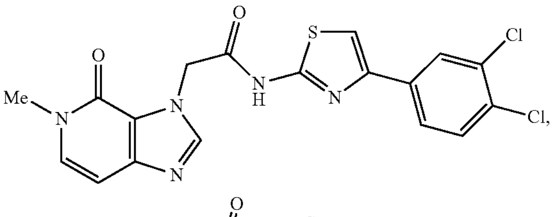,
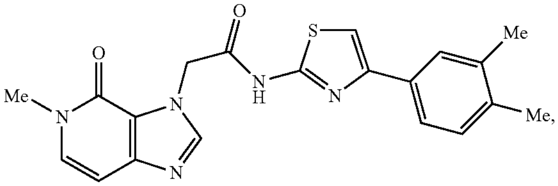, -continued
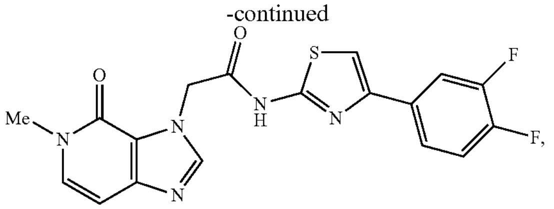
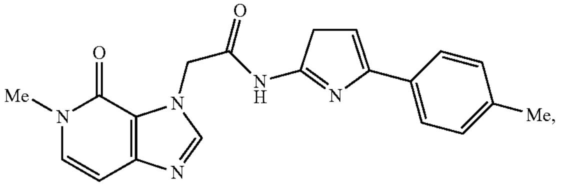
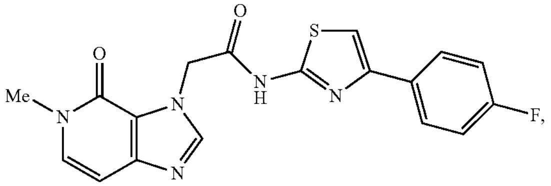
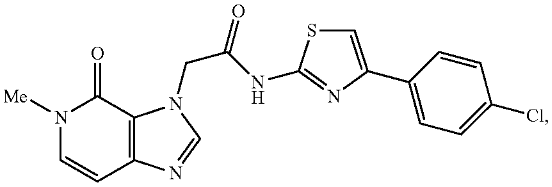
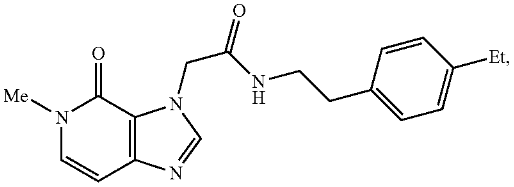
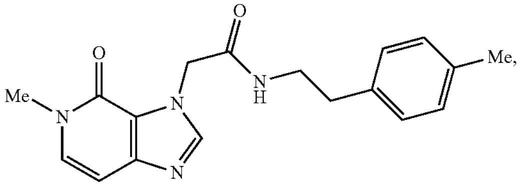
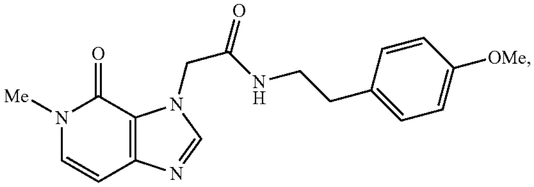
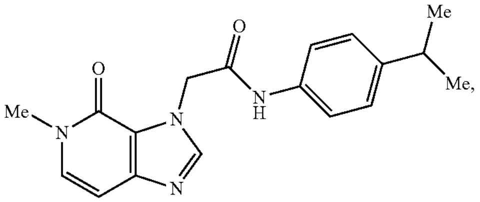
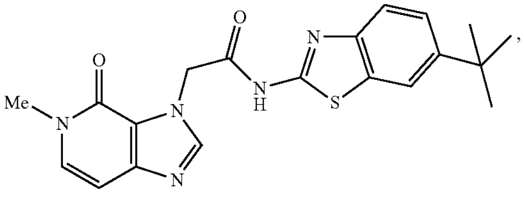
-continued
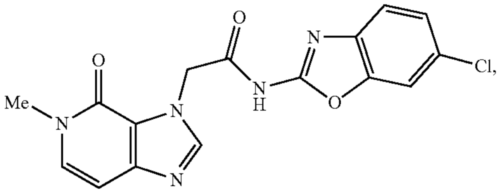
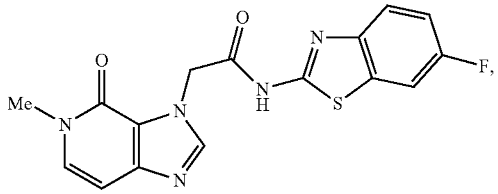
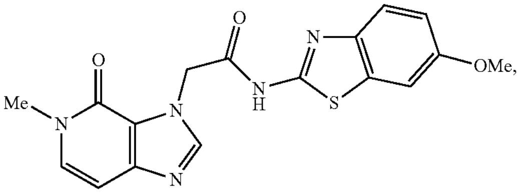
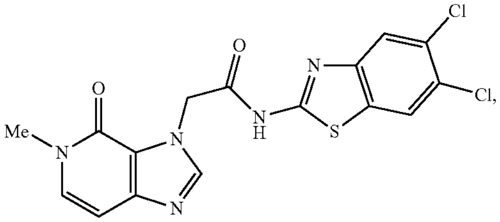
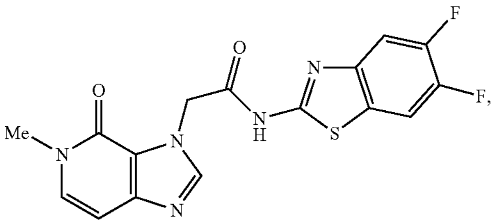
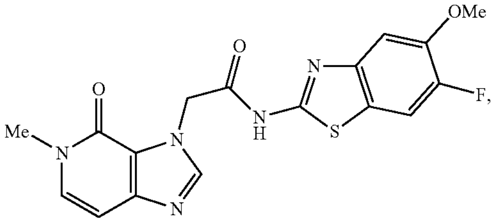
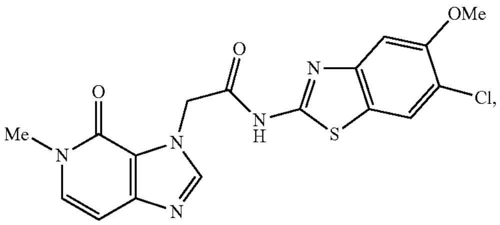
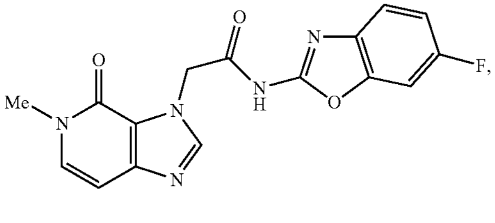

-continued
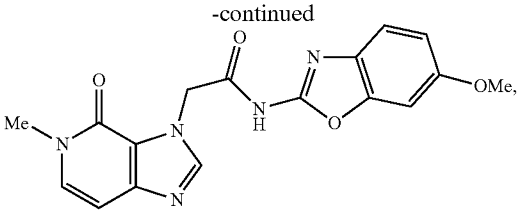
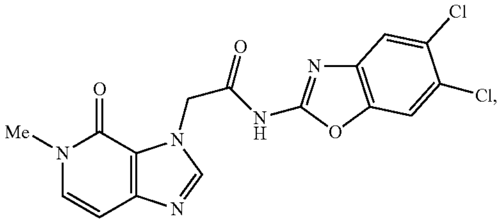
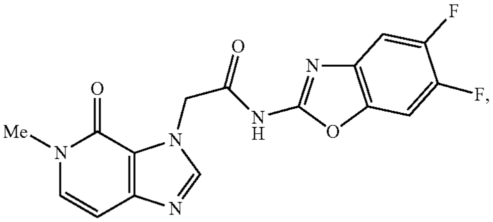
-continued
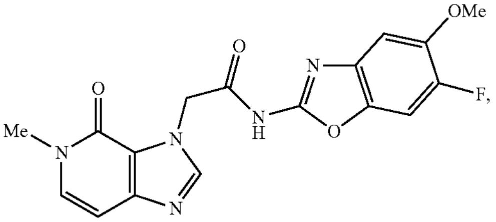
and
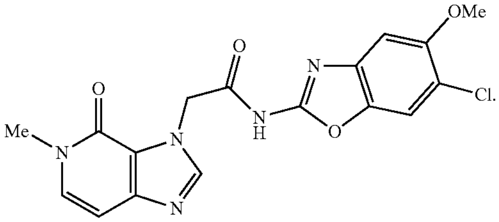
* * * * *